US012624019B2

(12) United States Patent
Feng et al.

(10) Patent No.: US 12,624,019 B2
(45) Date of Patent: May 12, 2026

(54) INDAZOLE DERIVATIVE, AND PREPARATION METHOD THEREFOR AND USE THEREOF

(71) Applicant: Leadingtac Pharmaceutical (Shaoxing) Co., Ltd., Shaoxing (CN)

(72) Inventors: Yan Feng, Shanghai (CN); Shiqiang Li, Shanghai (CN)

(73) Assignee: LEADINGTAC PHARMACEUTICAL (SHAOXING) CO., LTD., Zhejiang (CN)

( * ) Notice: Subject to any disclaimer, the term of this patent is extended or adjusted under 35 U.S.C. 154(b) by 661 days.

(21) Appl. No.: 18/000,205

(22) PCT Filed: Feb. 4, 2021

(86) PCT No.: PCT/CN2021/075341
§ 371 (c)(1),
(2) Date: Nov. 29, 2022

(87) PCT Pub. No.: WO2022/088551
PCT Pub. Date: May 5, 2022

(65) Prior Publication Data

US 2023/0192655 A1 Jun. 22, 2023

(30) Foreign Application Priority Data

Oct. 26, 2020 (CN) ......................... 202011157779.X

(51) Int. Cl.
*C07D 401/14* (2006.01)
*C07D 471/10* (2006.01)

(52) U.S. Cl.
CPC ......... *C07D 401/14* (2013.01); *C07D 471/10* (2013.01)

(58) Field of Classification Search
CPC ............................ C07D 401/14; C07D 471/10
See application file for complete search history.

(56) References Cited

U.S. PATENT DOCUMENTS

| | | | |
|---|---|---|---|
| 2012/0141910 | A1 | 6/2012 | Jia et al. |
| 2019/0015129 | A1 | 1/2019 | Sakamoto et al. |
| 2019/0019268 | A1 | 1/2019 | Viggers et al. |

FOREIGN PATENT DOCUMENTS

| | | | |
|---|---|---|---|
| CN | 102386424 | A | 3/2012 |
| CN | 105601968 | A | 5/2016 |
| CN | 105895943 | A | 8/2016 |
| CN | 114502158 | A | 5/2022 |
| JP | 2000038472 | A | 2/2000 |
| WO | 2019099926 | A1 | 5/2019 |
| WO | 2019160915 | A1 | 8/2019 |
| WO | 2020113233 | A1 | 6/2020 |
| WO | 2020264499 | A1 | 12/2020 |

*Primary Examiner* — Kamal A Saeed
*Assistant Examiner* — Quincy Mckoy
(74) *Attorney, Agent, or Firm* — NKL LAW; Bin Lu; Allen Xue

(57) ABSTRACT

A class of indazole derivatives targeting an IRAK4 kinase protein for degradation, and a preparation method therefor and the use thereof are provided. In particular, the compound of formula I, a preparation method therefor, and a pharmaceutical composition thereof and the use thereof are presented. The compound can significantly degrade the IRAK4 kinase protein in cells and can be used as a drug for the treatment and/or prevention of related diseases or conditions mediated by the IRAK4, such as cancers, immune diseases, and inflammatory diseases.

(I)

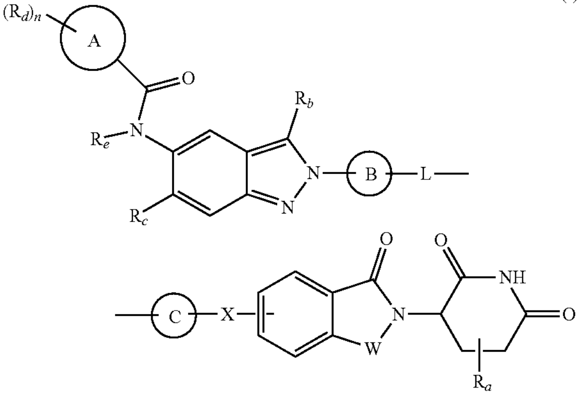

18 Claims, No Drawings

INDAZOLE DERIVATIVE, AND PREPARATION METHOD THEREFOR AND USE THEREOF

FIELD OF THE INVENTION

The present invention belongs to the field of pharmaceuticals. In particular, the present invention relates to indazole derivatives targeting IRAK4 protein for degradation, preparation methods therefor and their use in the preparation of medicaments for the treatment and/or prevention of related diseases or conditions mediated by IRAK4, such as cancer, immune diseases and inflammatory diseases.

BACKGROUND

Interleukin-1 receptor kinase 4 (IRAK4) is a serine/threonine-specific protein kinase with biologically important kinase activity and plays an important role in activating the immune system. Studies have shown that IRAK4 is a key factor downstream of IL-1β family receptors (including IL-1R, IL-18R, IL-33R, IL-36R) and Toll-like receptor (TLR) signaling pathways. Both IRAK4-deficient mice and IRAK4-deficient patients do not respond to TLR (except TLR3) and IL-1β family stimulation (Suzuki, Suzuki et al., Nature, 2002; Davidson, Currie et al., The Journal of Immunology, 2006; Ku, von Bernuth et al., JEM, 2007; Kim, Staschke et al., JEM, 2007).

According to the presence or absence of MyD88, TLR/IL-1β mediated signaling pathways can be divided into MyD88-dependent signaling pathways and MyD88-independent pathways, in which IL-1R and TLR2, TLR4, TLR7/8, TLR9 mediated signal transduction pathways rely on MyD88 as a regulator to activate downstream inflammatory signaling pathways. After TLR/IL-1β binds to the ligand, MyD88 molecules are recruited. MyD88 further recruits IRAK4 into TLR/IL-1β complex through its N-terminal death domain, and interacts with IRAK1 or IRAK2 and activates them (Kollewe, Mackensen et al., Journal of Biological Chemistry, 2004; Precious et al., J. Biol. Chem., 2009), thus transmitting signals to E3 ubiquitin ligase TNF receptor related factor (TRAF6) downstream, activating serine/threonine kinase TAK1, and then activating NF-κB and MAPK signal pathways (Wang, Deng et al., Nature, 2001), which causes the release of a variety of inflammatory cytokines and anti-apoptotic molecules. IRAK4-dependent TLR/IL-1β signaling pathway has been shown to be associated with a variety of diseases, such as multiple sclerosis, atherosclerosis, myocardial infarction, myocarditis (Valaperti, Nishii et al., Circulation, 2013), Vogt-Koyanagi-Harada syndrome, systemic lupus erythematosus (SLE), obesity (Ahmad, R., P. Shihab et al., Diabetology & Metabolic Syndrome, 2015), type 1 diabetes, rheumatoid arthritis, spondyloarthritis (especially psoriatic spondyloarthritis and Bekhterev's disease), lupus erythematosus, psoriasis, vitiligo, giant cell arteritis, chronic inflammatory intestinal diseases and viral diseases, such as HIV (human immunodeficiency virus), hepatitis virus (Staschke et al., The Journal of Immunology, 2009; Marquez et al., Ann Rheum Dis, 2014; Zambrano-Zaragoza et al., International Journal of Inflammation, 2014; Wang et al., Experimental and Therapeutic Medicine, 2015; Ciccia et al., Rheumatology, 2015); skin diseases such as psoriasis, atopic dermatitis, Kindler's syndrome, bullous pemphigoid, allergic contact dermatitis, alopecia areata, acneinversa and acne vulgaris; other inflammatory diseases such as allergy, Behcet's disease, gout, adult-onset Still's disease, pericarditis and chronic inflammatory intestinal diseases such as ulcerative colitis and Crohn's disease, transplant rejection reactions and graftversus-host reactions; Gynecological diseases such as adenomyosis, dysmenorrhea, dyspareunia and endometriosis, in particular, endometriosis-related pain and other endometriosis-related symptoms such as dysmenorrhea, dyspareunia, dysuria and dyschezia (Akoum, Lawson et al., Human Reproduction, 2007; Allhorn, Boing et al., Reproductive Biology and Endocrinology, 2008; Lawson, Bourcier et al., Journal of Reproductive Immunology, 2008; Sikora, Mielczarek-Palacz et al., American Journal of Reproductive Immunology, 2012; Khan, Kitajima et al, Journal of Obstetrics and Gynaecology Research, 2013; Santulli, Borghese et al., Human Reproduction, 2013); eye diseases such as retinal ischemia, keratitis, allergic conjunctivitis sicca, keratoconjunctivitis sicca, macular degeneration and uveitis (Kaarniranta and Salminen, J Mol Med (Berl), 2009; Sun and Pearlman, Investigative Ophthalmology & Visual Science, 2009; Redfern and McDermott, Experimental Eye Research, 2010; Kezic, Taylor et al, J Leukoc Biol, 2011; Chang, McCluskey et al., Clinical & Experimental Ophthalmology, 2012; Guo, Gao et al., Immunol Cell Biol, 2012; Lee, Hattori et al., Investigative Ophthalmology & Visual Science, 2012; Qi, Zhao et al., Investigative Ophthalmology & Visual Science, 2014); fibrosis diseases such as liver fibrosis, myocarditis, primary biliary cirrhosis, cystic fibrosis (Zhao, Zhao et al., Scand J Gastroenterol, 2011; Benias, Gopal et al., Clin Res Hepatol Gastroenterol, 2012; Yang, L. and E. Seki, Front Physiol, 2012; Liu, Hu et al., Biochim Biophys Acta., 2015); chronic liver diseases, such as fatty liver hepatitis, especially non-alcoholic fatty liver disease (NAFLD) and/or non-alcoholic steatohepatitis (NASH), alcoholic steatohepatitis (ASH)(Nozaki, Saibara et al, Alcohol Clin Exp Res, 2004; Csak, T., A. Velayudham et al., Am J Physiol Gastrointest Liver Physiol, 2011; Miura, Kodama et al., Gastroenterology, 2010; Kamari, Shaish et al., J Hepatol, 2011; Ye, Li et al., Gut, 2012; Roh, Seki, J Gastroenterol Hepatol, 2013; Ceccarelli, S., V. Nobili et al., World J Gastroenterol, 2014; Miura, Ohnishi, World J Gastroenterol, 2014; Stojsavljevic, Palcic et al., World J Gastroenterol, 2014); cardiovascular diseases and neurological disorders, such as myocardial reperfusion injury, myocardial infarction, hypertension (Oyama, Blais et al., Circulation, 2004; Timmers, Sluijter et al., Circulation Research, 2008; Fang and Hu, MedSci Monit, 2011; Bijani, International Reviews of Immunology, 2012; Bomfim, DosSantos et al., Clin Sci (Lond), 2012; Christia and Frangogiannis, European Journal of Clinical Investigation, 2013; Thompson and Webb, Clin Sci (Lond), 2013; Hernanz, Martinez-Revelles et al., British Journal of Pharmacology, 2015; Frangogiannis, Curr Opin Cardiol, 2015; Bomfim, Echem et al., Life Sciences, 2015), as well as Alzheimer's disease, stroke, craniocerebral trauma, amyotrophic lateral sclerosis (ALS) and Parkinson's disease (Brough, Tyrrell et al, Trends in Pharmacological Sciences, 2011; Carty and Bowie, Biochemical Pharmacology, 2011; Denes, Kitazawa, Cheng et al., The Journal of Immunology, 2011; Lim, Kou et al., The American Journal of Pathology, 2011; Béraud and Maguire-Zeiss, Parkinsonism & Related Disorders, 2012; Denes, Wilkinson et al., Disease Models & Mechanisms, 2013; Noelker, Morel et al., Sci. Rep., 2013; Wang, Wang et al., Stroke, 2013; Xiang, Chao et al., RevNeurosci, 2015; Lee, Lee et al., J Neuroinflammation, 2015); pruritus and pain (including acute, chronic, inflammatory and neuropathic pain) such as hyperalgesia, allodynia, premenstrual pain, pain related to endometriosis, postoperative pain, interstitial cystitis, CRPS (complex regional pain syndrome), trigeminal neuralgia, prostatitis, pain caused by spinal cord injury, pain caused by inflammation, low back pain, cancer pain, chemotherapy-related pain, HIV treatment-induced neuropathy, burns pain and chronic pain (Wolf, Livshits et al., Brain, Behavior, and Immunity, 2008; Kim, Lee et al., Toll-like Receptors: Roles in Infection and Neuropathology, 2009; del Rey, Apkarian et al., Annals of the New York Academy of Sciences, 2012; Guerrero, Cunha et al., European Journal of Pharmacology, 2012; Kwok, Hutchinson et al., PLoS ONE, 2012; Nicotra, Loram et al., Experimental Neurology, 2012; Chopra and Cooper, J Neuroimmune Pharmacol, 2013; David, Ratnayake et al., Neurobiology of Disease, 2013; Han, Zhao et al., Neuroscience, 2013; Liu and Ji, Pflugers Arch., 2013; Stokes, Cheung et al., Journal of Neuroinflammation, 2013; Zhao, Zhang et al., Neuroscience, 2013; Liu, Zhang et al., Cell Research, 2014; Park, Stokes et al., Cancer Chemother Pharmacol, 2014; van der Watt, Wilkinson et al., BMC Infect Dis, 2014; Won, K. A., M. J. Kim et al., J Pain, 2014; Min, Ahmad et al., Photochem Photobiol., 2015; Schrepf, Bradley et al., Brain Behav Immun, 2015; Wong, L., J. D. Done et al., Prostate, 2015); tumor diseases such as certain lymphomas: ABC-DLBCL (activated B-cell diffuse large cell B-cell lymphoma), mantle cell lymphoma and Waldenstrom disease (disease), as well as chronic lymphocytic leukemia, melanoma, pancreatic tumor and hepatocellular carcinoma (Ngo, Young et al., Nature, 2011; Puente, Pinyol et al., Nature, 2011; Ochi, Nguyen et al., J Exp Med, 2012; Srivastava, Geng et al., Cancer Research, 2012; Treon, Xu et al., New England Journal of Medicine, 2012; Choi, Kim et al., Human Pathology, 2013; Liang, Chen et al., Clinical Cancer Research, 2013), ras-dependent tumors, breast cancer, ovarian cancer, colorectal cancer, head and neck cancer, lung cancer, prostate cancer.

The regulation of IRAK4-mediated signaling pathway is mainly related to its kinase function. However, there are also some reports indicating in some cell types, the signal regulation of downstream processes by IRAK4 is related to the non-kinase function of IRAK4. Cushing et al. indicated that although the phosphorylation level of IRAK4 was reduced in human skin fibroblasts stimulated by IL-1β, the pharmacological inhibition of IRAK4 did not lead to the inhibition of IL-6 and TNF-α. In support of these results, the scaffold function of IRAK4 is important for IL1 signaling in IRAK4-deficient fibroblasts compared with wild-type cells, but its kinase effect is redundant. At the same time, Chiang and his colleagues also said that IRAK4 kinase activity was not necessary in human B cells and T cells, dendritic cells and monocytes, and siRNA gene excision also showed that IRAK4 had a scaffold function in these cells. A variety of potent selective inhibitors against IRAK4 have been reported, such as CA-4948, BAY-1834845, BMS-986126 and PF-06650833. These inhibitors can selectively inhibit the kinase activity of IRAK4 and are mainly used for the prevention and treatment of autoimmune diseases, inflammatory diseases and tumor diseases. However, on the one hand, IRAK4 has the function of scaffold protein and active kinase, and on the other hand, traditional small molecule inhibitors are prone to drug resistance, therefore, only inhibition of IRAK4 kinase activity may not be sufficient to produce therapeutic effect.

Proteolysis Targeting Chimeria (PROTAC) is a technology different from traditional small molecule inhibitors. Traditional small molecule inhibitors usually need to act on the active site of the target protein to inhibit its activity. PROTAC is a heterogeneous bifunctional molecule, with a small molecule inhibitor that can recognize the target protein through a linker at one end and an E3 ubiquitin ligase ligand that can recognize E3 ubiquitin ligase at the other end. This bifunctional molecule recognizes the target protein and E3 ubiquitin ligase in the body, and pulls the target protein and E3 ubiquitin ligase closer to form a ternary complex. After the target protein is ubiquitinated, the target protein is degraded through the ubiquitin-proteasome pathway in the body. Compared with traditional small molecule inhibitors, on the one hand, PROTAC only needs to bring the target protein closer to E3 ubiquitin ligase to degrade the substrate. This mode of action makes this technology applicable to some non-druggable targets; on the other hand, after the target protein is degraded, since PROTAC molecules can be released to continue to participate in the degradation process of the next protein, so this degradation has a catalytic effect, so that less dose of PROTAC drug can achieve efficient degradation; on the other hand, traditional small molecule inhibitors are often prone to drug resistance because of point mutations, which makes small molecule inhibitors lose the inhibitory effect on the target. PROTAC can directly degrade the target protein, which can avoid the drug resistance caused by point mutations to a certain extent. Therefore, compared with traditional small molecule inhibitors, the use of PROTAC technology for new drug small molecule research and development has high advantages and feasibility, and is expected to become the next generation of promising new drugs. PROTAC technology has also been applied to the modification of various target drugs, such as androgen receptor, estrogen protein receptor, BTK, etc. Several types of compounds targeting IRAK4 degradation are disclosed in US2019/0151295, US2019/0192688, WO2019/160915 and WO2020/113233, and more compounds targeting IRAK4 degradation are to be developed.

SUMMARY OF THE INVENTION

Due to the large molecular weight of PROTAC, PK has become one of the main obstacles to prepare a medicament, so compounds with good PK properties are preferred for preparing a medicament. The invention provides a class of compounds with good degradation properties and PK properties.

The invention provides a compound of formula I, and/or its a stereoisomer, an enantiomer, a diastereomer, a deuterate, a hydrate, a solvate, a prodrug and/or a pharmaceutically acceptable salt thereof.

I

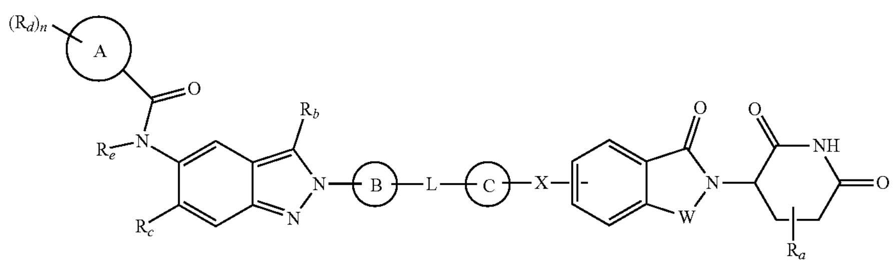

wherein:

$R_a$ is hydrogen, halogen, C1-C6 alkyl or —O—(C1-C6 alkyl), and the alkyl is optionally substituted by halogen or hydroxyl;

ring A is 6-10 membered aryl or 5-10 membered heteroaryl;

$R_d$ is each independently hydrogen, halogen, cyano, C1-C6 alkyl, —O—(C1-C6 alkyl), —O—(C3-C6 cycloalkyl), C3-C6 cycloalkyl, or 5-10-membered heteroaryl, and the alkyl, cycloalkyl, and heteroaryl are optionally substituted by one or more groups selected from halogen, hydroxyl, or amino;

n is 1, 2, 3 or 4;

$R_e$ is hydrogen or C1-C6 alkyl;

$R_e$ is hydrogen, —O—(C1-C6 alkyl), —O—(C3-C8 cycloalkyl), —O-(3-8-membered heterocycloalkyl), —O-aryl, —O-heteroaryl, —N(C1-C6 alkyl)$_{1-2}$, —NH (C3-C8 cycloalkyl), —NH (3-8-membered heterocycloalkyl), —NH-aryl, —NH-heteroaryl, C1-C6 alkyl, C2-C6 alkenyl, C2-C6 alkynyl, C3-C8 cycloalkyl, 3-8 membered heterocycloalkyl, 6-10 membered aryl or 5-10 membered heteroaryl, and the alkyl, cycloalkyl, heterocycloalkyl, aryl and heteroaryl are optionally substituted by one or more groups independently selected from hydroxyl, amino, halogen or cyano;

$R_b$ is hydrogen, —O—(C1-C6 alkyl), —O—(C3-C8 cycloalkyl), —O-(3-8-membered heterocycloalkyl), —O-aryl, —O-heteroaryl, —N(C1-C6 alkyl)$_{1-2}$, —NH (C3-C8 cycloalkyl), —NH (3-8-membered heterocycloalkyl), —NH-aryl, —NH-heteroaryl, C1-C6 alkyl, C2-C6 alkenyl, C2-C6 alkynyl, C3-C8 cycloalkyl, 3-8 membered heterocycloalkyl, 6-10 membered aryl or 5-10 membered heteroaryl, and the alkyl, cycloalkyl, heterocycloalkyl, aryl and heteroaryl are optionally substituted by one or more groups independently selected from hydroxyl, amino, halogen or cyano;

ring B is 6-10-membered aryl, 5-10-membered heteroaryl, C3-C12 cycloalkyl or 3-12-membered heterocycloalkyl containing 1-2 heteroatoms selected from N, O or S, and the aryl, heteroaryl, cycloalkyl and heterocycloalkyl are optionally substituted by a substituent selected from halogen, oxo, cyano, amino, hydroxyl, C1-C6 alkyl, C1-C6 haloalkyl, C1-C6 hydroxyalkyl or —O—(C1-C6 alkyl);

ring C is 6-10-membered aryl, 5-10-membered heteroaryl, C3-C12 cycloalkyl or 3-12-membered heterocycloalkyl containing 1-2 heteroatoms selected from N, O or S, and the aryl, heteroaryl, cycloalkyl and heterocycloalkyl are optionally substituted by a substituent selected from halogen, oxo, cyano, amino, hydroxyl, C1-C6 alkyl, C1-C6 haloalkyl, C1-C6 hydroxyalkyl or —O—(C1-C6 alkyl);

X is bond, —O—, —NH—, —N(C1-C6 alkyl)-, —S—, —C═C—, —C≡C—, —C(O)—, —OC(O)—, —C(O)O—, —NHC(O)— or —C(O)NH—;

W is —$CR_gR_h$ or —C(O);

$R_g$ and $R_h$ are each independently hydrogen, halogen, C1-C4 alkyl, C1-C4 chloroalkyl, C1-C4 hydroxyalkyl or C3-C6 cycloalkyl;

L is —$(CH_2)_j$—, one or more methylene in the —$(CH_2)_j$— are optionally replaced by a group selected from —$NR^{3'}$—, —O—, —S—, —S(O)—, —S(O)$NR^{3'}$—, —$NR^{3'}$S(O)—, —S(O)$_2$—, —S(O)$_2NR^{3'}$—, —$NR^{3'}$S(O)$_2$—, —$NR^{4'}$S(O)$_2NR^{3'}$—, —$CR^{1'}R^{2'}$, —C(O)—, —C(O)O—, —OC(O)—, —$NR^{3'}$C(O)O—, —OC(O)$NR^{3}$, —, —C(O)$NR^{3'}$—, —$NR^{3}$C(O)—, —$NR^{4'}$C(O)$NR^{3'}$—, —P(O)—, —P(O)O—, —OP(O)—, —OP(O)O—, vinylidene, or ethynylene;

$R^{1'}$ and $R^{2'}$ are each independently halogen, —OH, —$NH_2$, C1-C4 alkyl, C1-C4 chloroalkyl, C1-C4 hydroxyalkyl, —O(C1-C4 alkyl), —NH(C1-C4 alkyl), —NH(C1-C4 alkyl), C3-C6 cycloalkyl, —O(C3-C6 cycloalkyl), —NH(C3-C6 cycloalkyl), 3-6-membered heterocycloalkyl, —O(3-6-membered heterocycloalkyl), or —NH(C3-C6 cycloalkyl);

$R^{3'}$ and $R^{4'}$ are each independently hydrogen or C1-C6 alkyl;

j is 1, 2, 3, 4, 5 or 6;

provided that the compound of formula I does not include the following compounds

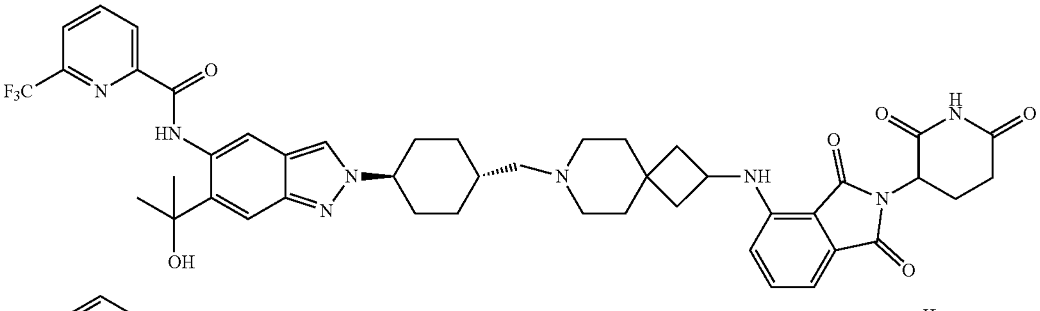

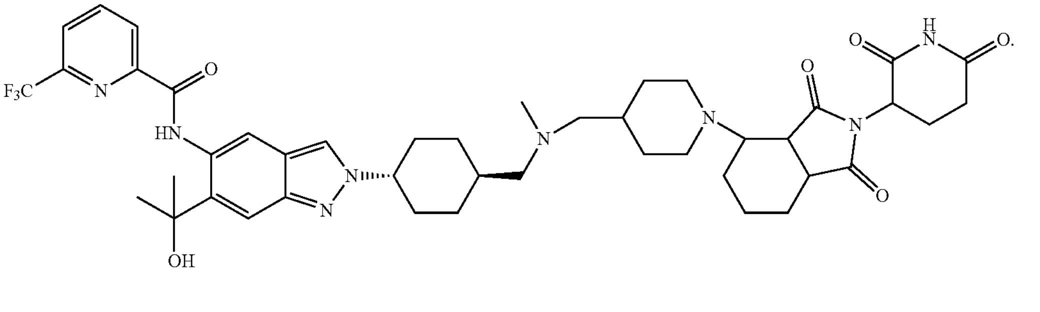

Preferably, in some embodiments of the present invention, the compound of formula I, and/or its stereoisomer, enantiomer, diastereomer, deuterate, hydrate, solvate, prodrug and/or pharmaceutically acceptable salt is a compound of formula II:

II

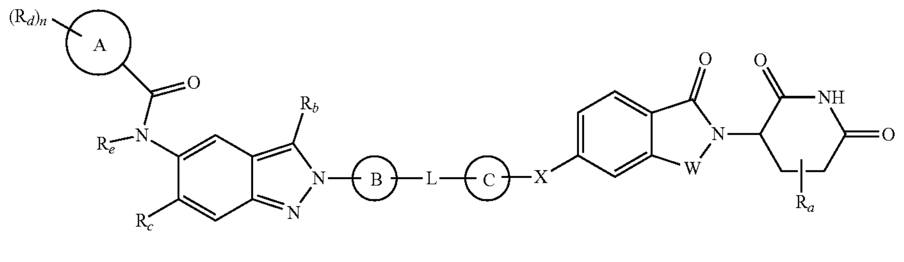

wherein, $R_a$, $R_b$, $R_c$, $R_d$, $R_e$, n, ring A, ring B, L, ring C, X, and W are as defined above.

Preferably, in certain embodiments of the present invention, the compound of formula I, and/or its stereoisomer, enantiomer, diastereomer, deuterate, hydrate, solvate, prodrug and/or pharmaceutically acceptable salt, X is bond.

Preferably, in certain embodiments of the present invention, the compound of formula I, and/or its stereoisomer, enantiomer, diastereomer, deuterate, hydrate, solvate, prodrug and/or pharmaceutically acceptable salt, ring B is 3-8-membered monocycloalkyl, 7-12-membered spiro cycloalkyl, 7-12-membered fused cycloalkyl, 3-8-membered monocyclic heterocycloalkyl containing 1-2 N heteroatoms, 7-12-membered fused heterocycloalkyl containing 1-2 N heteroatoms or 7-12-membered spiro heterocycloalkyl containing 1-2 N heteroatoms.

More preferably, in certain embodiments of the present invention, the compound of Formula I, and/or its stereoisomer, enantiomer, diastereomer, deuterate, hydrate, solvate, prodrug and/or pharmaceutically acceptable salt, ring B is cyclohexyl, piperidinyl or piperazinyl.

More preferably, in certain embodiments of the present invention, the compound of Formula I, and/or its stereoisomer, enantiomer, diastereomer, deuterate, hydrate, solvate, prodrug and/or pharmaceutically acceptable salt, ring B is piperidinyl.

Preferably, in certain embodiments of the present invention, the compound of formula I, and/or its stereoisomer, enantiomer, diastereomer, deuterate, hydrate, solvate, prodrug and/or pharmaceutically acceptable salt, ring B is

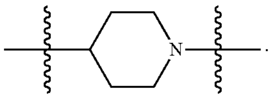 [SMILES: *C1CCN(*)CC1]

Preferably, in certain embodiments of the present invention, the compound of formula I, and/or its stereoisomer, enantiomer, diastereomer, deuterate, hydrate, solvate, prodrug and/or pharmaceutically acceptable salt, ring C is 3-8-membered monocycloalkyl, 7-12-membered spiro cycloalkyl, 7-12-membered fused cycloalkyl, 3-8-membered monocyclic heterocycloalkyl containing 1-2 N heteroatoms, 7-12-membered fused heterocycloalkyl containing 1-2 N heteroatoms or 7-12-membered spiro heterocycloalkyl containing 1-2 N heteroatoms.

More preferably, in certain embodiments of the present invention, the compound of Formula I, and/or its stereoisomer, enantiomer, diastereomer, deuterate, hydrate, solvate, prodrug and/or pharmaceutically acceptable salt, ring C is cyclohexyl, piperidinyl, piperazinyl,

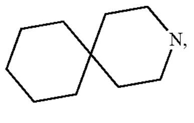

or

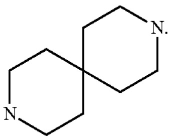

More preferably, in certain embodiments of the present invention, the compound of formula I, and/or its stereoisomer, enantiomer, diastereomer, deuterate, hydrate, solvate, prodrug and/or pharmaceutically acceptable salt, ring C is

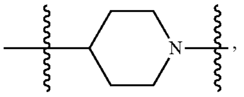

,

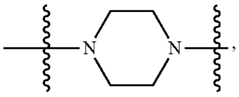

,

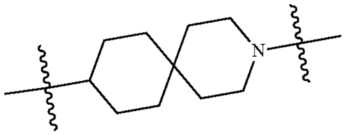

or

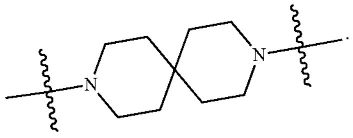

Preferably, in certain embodiments of the present invention, the compound of formula I, and/or its stereoisomer, enantiomer, diastereomer, deuterate, hydrate, solvate, prodrug and/or pharmaceutically acceptable salt, $R_a$ is hydrogen.

Preferably, in certain embodiments of the present invention, the compound of formula I, and/or its stereoisomer, enantiomer, diastereomer, deuterate, hydrate, solvate, prodrug and/or pharmaceutically acceptable salt, W is C(O).

Preferably, in certain embodiments of the present invention, the compound of Formula I, and/or its stereoisomer, enantiomer, diastereomer, deuterate, hydrate, solvate, prodrug and/or pharmaceutically acceptable salt, ring A is phenyl or pyridyl.

Preferably, in certain embodiments of the present invention, the compound of formula I, and/or its stereoisomer, enantiomer, diastereomer, deuterate, hydrate, solvate, prodrug and/or pharmaceutically acceptable salt, $R_d$ is each independently hydrogen, halogen, cyano, C1-C6 alkyl, C3-C6 cycloalkyl, and the alkyl and cycloalkyl are optionally substituted by one or more groups selected from halogen, hydroxyl or amino.

More preferably, in certain embodiments of the present invention, the compound of formula I, and/or its stereoisomer, enantiomer, diastereomer, deuterate, hydrate, solvate, prodrug and/or pharmaceutically acceptable salt, $R_d$ is each independently hydrogen, halogen or C1-C6 alkyl optionally substituted by one or more groups selected from F or hydroxyl.

More preferably, in certain embodiments of the present invention, the compound of formula I, and/or its stereoisomer, enantiomer, diastereomer, deuterate, hydrate, solvate, prodrug and/or pharmaceutically acceptable salt, $R_d$ is hydrogen, F, methyl, difluoromethyl, trifluoromethyl or 2-hydroxypropyl.

Preferably, in certain embodiments of the present invention, the compound of formula I, and/or its stereoisomer, enantiomer, diastereomer, deuterate, hydrate, solvate, prodrug and/or pharmaceutically acceptable salt, n is 1 or 2.

Preferably, in certain embodiments of the present invention, the compound of formula I, and/or its stereoisomer, enantiomer, diastereomer, deuterate, hydrate, solvate, prodrug and/or pharmaceutically acceptable salt, $R_e$ is hydrogen.

Preferably, in certain embodiments of the present invention, the compound of formula I, and/or its stereoisomer, enantiomer, diastereomer, deuterate, hydrate, solvate, prodrug and/or pharmaceutically acceptable salt, $R_c$ is hydrogen, —O(C1-C6 alkyl), —N(C1-C6 alkyl)$_{1-2}$, C1-C6 alkyl, —O(C3-C6 cycloalkyl), —N(C3-C6 cycloalkyl), —O(3-6-membered heterocycloalkyl), or —N(3-6-membered heterocycloalkyl), and the alkyl, cycloalkyl, and heterocycloalkyl are optionally substituted by one or more groups independently selected from hydroxyl, amino, halogen, or cyano.

More preferably, in certain embodiments of the present invention, the compound of formula I, and/or its stereoisomer, enantiomer, diastereomer, deuterate, hydrate, solvate, prodrug and/or pharmaceutically acceptable salt, $R_c$ is C1-C6 alkyl optionally substituted by one or more groups independently selected from hydroxyl or halogen, C3-C6 cycloalkyl containing one or two N heteroatoms, or —O(C1-C6 alkyl) optionally substituted by one or more groups independently selected from hydroxyl or halogen.

More preferably, in certain embodiments of the present invention, the compound of formula I, and/or its stereoisomer, enantiomer, diastereomer, deuterate, hydrate, solvate, prodrug and/or pharmaceutically acceptable salt, $R_c$ is difluoromethyl, hydroxyl-substituted pyrrolidyl, 2-hydroxypropyl, methoxy, ethoxy or isopropoxy.

Preferably, in some embodiments of the present invention, the compound of formula I, and/or its stereoisomer, enantiomer, diastereomer, deuterate, hydrate, solvate, prodrug and/or pharmaceutically acceptable salt, $R_b$ is hydrogen or C1-C6 alkyl, and the alkyl is optionally substituted by one or more groups independently selected from hydroxyl, amino, halogen, or cyano.

Preferably, in certain embodiments of the present invention, the compound of formula I, and/or its stereoisomer, enantiomer, diastereomer, deuterate, hydrate, solvate, prodrug and/or pharmaceutically acceptable salt, $R_b$ is hydrogen or methyl.

Preferably, in some embodiments of the present invention, the compound of formula I, and/or its stereoisomer, enantiomer, diastereomer, deuterate, hydrate, solvate, prodrug and/or pharmaceutically acceptable salt, L is $—(CH_2)_j—$, and one or more methylene in the $—(CH_2)_j—$ are optionally replaced by a group selected from $—NR^{3'}—$, —O—, $—CR^{1'}R^{2'}$, —C(O)—, —C(O)O—, —OC(O)—, $—C(O)NR^{3'}—$, or $—NR^3C(O)—$; $R^{1'}$ and $R^{2'}$ are each independently halogen, —OH, $—NH_2$, C1-C4 alkyl, C1-C4 chloroalkyl, C1-C4 hydroxyalkyl or —O(C1-C4 alkyl); $R^{3'}$ and $R^{4'}$ are each independently hydrogen or methyl; j is 1, 2 or 3.

Preferably, in certain embodiments of the present invention, the compound of formula I, and/or its stereoisomer, enantiomer, diastereomer, deuterate, hydrate, solvate, prodrug and/or pharmaceutically acceptable salt, L is $—(CH_2)_j—$, j is 1, 2 or 3.

More preferably, in certain embodiments of the present invention, the compound of formula I, and/or its stereoisomer, enantiomer, diastereomer, deuterate, hydrate, solvate, prodrug and/or pharmaceutically acceptable salt, L is

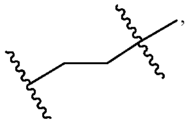, 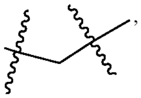, 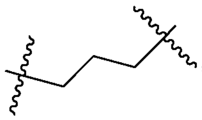, 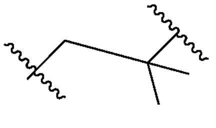 or 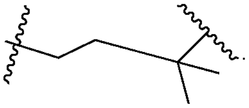.

In another preferred embodiment, $R_a$ is hydrogen, halogen, C1-C6 alkyl or —O—(C1-C6 alkyl), and the alkyl is optionally substituted by halogen or hydroxyl;

ring A is 6-10 membered aryl or 5-10 membered heteroaryl;

$R_d$ is each independently hydrogen, halogen, cyano, C1-C6 alkyl, —O—(C1-C6 alkyl), —O—(C3-C6 cycloalkyl), C3-C6 cycloalkyl, or 5-10-membered heteroaryl, and the alkyl, cycloalkyl, and heteroaryl are optionally substituted by one or more groups selected from halogen, hydroxyl, or amino;

n is 1, 2, 3 or 4;

$R_e$ is hydrogen or C1-C6 alkyl;

$R_c$ is hydrogen, —O—(C1-C6 alkyl), —O—(C3-C8 cycloalkyl), —O-(3-8-membered heterocycloalkyl), —O-aryl, —O-heteroaryl, —N(C1-C6 alkyl)$_{1-2}$, —NH (C3-C8 cycloalkyl), —NH (3-8-membered heterocycloalkyl), —NH-aryl, —NH-heteroaryl, C1-C6 alkyl, C2-C6 alkenyl, C2-C6 alkynyl, C3-C8 cycloalkyl, 3-8 membered heterocycloalkyl, 6-10 membered aryl or 5-10 membered heteroaryl, and the alkyl, cycloalkyl, heterocycloalkyl, aryl and heteroaryl are optionally substituted by one or more groups independently selected from hydroxyl, amino, halogen or cyano;

$R_b$ is hydrogen, —O—(C1-C6 alkyl), —O—(C3-C8 cycloalkyl), —O-(3-8-membered heterocycloalkyl), —O-aryl, —O-heteroaryl, —N(C1-C6 alkyl)$_{1-2}$, —NH (C3-C8 cycloalkyl), —NH (3-8-membered heterocycloalkyl), —NH-aryl, —NH-heteroaryl, C1-C6 alkyl, C2-C6 alkenyl, C2-C6 alkynyl, C3-C8 cycloalkyl, 3-8 membered heterocycloalkyl, 6-10 membered aryl or 5-10 membered heteroaryl, and the alkyl, cycloalkyl, heterocycloalkyl, aryl and heteroaryl are optionally substituted by one or more groups independently selected from hydroxyl, amino, halogen or cyano;

ring B is 6-10 membered aryl, 5-10 membered heteroaryl, C3-C12 cycloalkyl or 3-12 membered heterocycloalkyl containing 1-2 heteroatoms selected from N, O or S, and the aryl, heteroaryl, cycloalkyl and heterocycloalkyl are optionally substituted by a substituent selected from halogen, oxo, cyano, amino, hydroxyl, C1-C6 alkyl, C1-C6 haloalkyl, C1-C6 hydroxyalkyl or —O—(C1-C6 alkyl);

ring C is 6-10 membered aryl, 5-10 membered heteroaryl, C3-C12 cycloalkyl or 3-12 membered heterocycloalkyl containing 1-2 heteroatoms selected from N, O or S, and the aryl, heteroaryl, cycloalkyl and heterocycloalkyl are optionally substituted by a substituent selected from halogen, oxo, cyano, amino, hydroxyl, C1-C6 alkyl, C1-C6 haloalkyl, C1-C6 hydroxyalkyl or —O—(C1-C6 alkyl);

X is bond;

W is —$CR_gR_h$ or —C(O);

$R_g$ and $R_h$ are each independently hydrogen, halogen, C1-C4 alkyl, C1-C4 chloroalkyl, C1-C4 hydroxyalkyl or C3-C6 cycloalkyl;

L is —$(CH_2)_j$—;

j is 1, 2, 3, 4, 5 or 6.

In another preferred embodiment, $R_a$ is hydrogen, halogen, C1-C6 alkyl or —O—(C1-C6 alkyl), and the alkyl is optionally substituted by halogen or hydroxyl;

ring A is 6-10 membered aryl or 5-10 membered heteroaryl;

$R_d$ is each independently hydrogen, halogen, cyano, C1-C6 alkyl, —O—(C1-C6 alkyl), —O—(C3-C6 cycloalkyl), C3-C6 cycloalkyl, or 5-10-membered heteroaryl, and the alkyl, cycloalkyl, and heteroaryl are optionally substituted by one or more groups selected from halogen, hydroxyl, or amino;

n is 1, 2, 3 or 4;

$R_e$ is hydrogen or C1-C6 alkyl;

$R_c$ is hydrogen, —O—(C1-C6 alkyl), —O—(C3-C8 cycloalkyl), —O-(3-8-membered heterocycloalkyl), —O-aryl, —O-heteroaryl, —N(C1-C6 alkyl)$_{1-2}$, —NH (C3-C8 cycloalkyl), —NH (3-8-membered heterocycloalkyl), —NH-aryl, —NH-heteroaryl, C1-C6 alkyl, C2-C6 alkenyl, C2-C6 alkynyl, C3-C8 cycloalkyl, 3-8 membered heterocycloalkyl, 6-10 membered aryl or 5-10 membered heteroaryl, and the alkyl, cycloalkyl, heterocycloalkyl, aryl and heteroaryl are optionally substituted by one or more groups independently selected from hydroxyl, amino, halogen or cyano;

$R_b$ is hydrogen, —O—(C1-C6 alkyl), —O—(C3-C8 cycloalkyl), —O-(3-8-membered heterocycloalkyl), —O-aryl, —O-heteroaryl, —N(C1-C6 alkyl)$_{1-2}$, —NH (C3-C8 cycloalkyl), —NH (3-8-membered heterocycloalkyl), —NH-aryl, —NH-heteroaryl, C1-C6 alkyl, C2-C6 alkenyl, C2-C6 alkynyl, C3-C8 cycloalkyl, 3-8 membered heterocycloalkyl, 6-10 membered aryl or 5-10 membered heteroaryl, and the alkyl, cycloalkyl, heterocycloalkyl, aryl and heteroaryl are optionally substituted by one or more groups independently selected from hydroxyl, amino, halogen or cyano;

ring B is 6-10 membered aryl, 5-10 membered heteroaryl, or 3-12 membered heterocycloalkyl containing 1-2 heteroatoms selected from N, O or S, and the aryl, heteroaryl, and heterocycloalkyl are optionally substituted by a substituent selected from halogen, oxo, cyano, amino, hydroxyl, C1-C6 alkyl, C1-C6 haloalkyl, C1-C6 hydroxyalkyl or —O—(C1-C6 alkyl);

ring C is 6-10 membered aryl, 5-10 membered heteroaryl, C3-C12 cycloalkyl or 3-12 membered heterocycloalkyl containing 1-2 heteroatoms selected from N, O or S, and the aryl, heteroaryl, and heterocycloalkyl are optionally substituted by a substituent selected from halogen, oxo, cyano, amino, hydroxyl, C1-C6 alkyl, C1-C6 haloalkyl, C1-C6 hydroxyalkyl or —O—(C1-C6 alkyl);

X is bond;

W is —$CR_gR_h$ or —C(O);

$R_g$ and $R_h$ are each independently hydrogen, halogen, C1-C4 alkyl, C1-C4 chloroalkyl, C1-C4 hydroxyalkyl or C3-C6 cycloalkyl;

L is —$(CH_2)_j$—, and one or more methylene in the —$(CH_2)_j$— are optionally replaced by a group selected from —$NR^{3'}$—, —O—, —S—, —S(O)—, —S(O)$NR^{3'}$—, —$NR^{3'}$S(O)—, —$S(O)_2$—, —$S(O)_2NR^{3'}$—, —$NR^{3'}S(O)_2$—, —$NR^{4'}S(O)_2NR^{3'}$—, —$CR^{1'}R^{2'}$, —C(O)—, —C(O)O—, —OC(O)—, —$NR^{3'}$C(O)O—, —OC(O)$NR^{3'}$—, —C(O)$NR^{3'}$—, —$NR^{3'}$C(O)—, —$NR^{4'}C(O)NR^{3'}$, —P(O)—, —P(O)O—, —OP(O)—, —OP(O)O—, vinylidene, or ethynylene;

$R^{1'}$ and $R^{2'}$ are each independently halogen, —OH, —$NH_2$, C1-C4 alkyl, C1-C4 chloroalkyl, C1-C4 hydroxyalkyl, —O(C1-C4 alkyl), —NH(C1-C4 alkyl), —NH(C1-C4 alkyl), C3-C6 cycloalkyl, —O(C3-C6 cycloalkyl), —NH(C3-C6 cycloalkyl), 3-6-membered heterocycloalkyl, —O(3-6-membered heterocycloalkyl), or —NH(C3-C6 cycloalkyl);

$R^{3'}$ and $R^{4'}$ are each independently hydrogen or C1-C6 alkyl;

j is 1, 2, 3, 4, 5 or 6.

In another preferred embodiment, $R_a$ is hydrogen, halogen, C1-C6 alkyl or —O—(C1-C6 alkyl), and the alkyl is optionally substituted by halogen or hydroxyl;

ring A is 6-10 membered aryl or 5-10 membered heteroaryl;

$R_d$ is each independently hydrogen, halogen, cyano, C1-C6 alkyl, —O—(C1-C6 alkyl), —O—(C3-C6 cycloalkyl), C3-C6 cycloalkyl, or 5-10-membered heteroaryl, and the alkyl, cycloalkyl, and heteroaryl are optionally substituted by one or more groups selected from halogen, hydroxyl, or amino;

n is 1, 2, 3 or 4;

$R_e$ is hydrogen or C1-C6 alkyl;

$R_c$ is hydrogen, —O—(C1-C6 alkyl), —O—(C3-C8 cycloalkyl), —O-(3-8-membered heterocycloalkyl), —O-aryl, —O-heteroaryl, —N(C1-C6 alkyl)$_{1-2}$, —NH (C3-C8 cycloalkyl), —NH (3-8-membered heterocycloalkyl), —NH-aryl, —NH-heteroaryl, C1-C6 alkyl, C2-C6 alkenyl, C2-C6 alkynyl, C3-C8 cycloalkyl, 3-8 membered heterocycloalkyl, 6-10 membered aryl or 5-10 membered heteroaryl, and the alkyl, cycloalkyl, heterocycloalkyl, aryl and heteroaryl are optionally substituted by one or more groups independently selected from hydroxyl, amino, halogen or cyano;

$R_b$ is hydrogen, —O—(C1-C6 alkyl), —O—(C3-C8 cycloalkyl), —O-(3-8-membered heterocycloalkyl), —O-aryl, —O-heteroaryl, —N(C1-C6 alkyl)$_{1-2}$, —NH (C3-C8 cycloalkyl), —NH (3-8-membered heterocycloalkyl), —NH-aryl, —NH-heteroaryl, C1-C6 alkyl, C2-C6 alkenyl, C2-C6 alkynyl, C3-C8 cycloalkyl, 3-8 membered heterocycloalkyl, 6-10 membered aryl or 5-10 membered heteroaryl, and the alkyl, cycloalkyl, heterocycloalkyl, aryl and heteroaryl are optionally substituted by one or more groups independently selected from hydroxyl, amino, halogen or cyano;

ring B is 6-10 membered aryl, 5-10 membered heteroaryl, or 3-12 membered heterocycloalkyl containing 1-2 heteroatoms selected from N, O or S, and the aryl, heteroaryl, and heterocycloalkyl are optionally substituted by a substituent selected from halogen, oxo, cyano, amino, hydroxyl, C1-C6 alkyl, C1-C6 haloalkyl, C1-C6 hydroxyalkyl or —O—(C1-C6 alkyl);

ring C is 6-10 membered aryl, 5-10 membered heteroaryl, or 3-12 membered heterocycloalkyl containing 1-2 heteroatoms selected from N, O or S, and the aryl, heteroaryl, and heterocycloalkyl are optionally substituted by a substituent selected from halogen, oxo, cyano, amino, hydroxyl, C1-C6 alkyl, C1-C6 haloalkyl, C1-C6 hydroxyalkyl or —O—(C1-C6 alkyl);

X is bond;

W is $—CR_gR_h$ or —C(O);

$R_g$ and $R_h$ are each independently hydrogen, halogen, C1-C4 alkyl, C1-C4 chloroalkyl, C1-C4 hydroxyalkyl or C3-C6 cycloalkyl;

L is $—(CH_2)_j—$;

j is 1, 2, 3, 4, 5 or 6.

In another preferred embodiment, $R_a$ is hydrogen, halogen, C1-C6 alkyl or —O—(C1-C6 alkyl), and the alkyl is optionally substituted by halogen or hydroxyl;

ring A is 6-10 membered aryl or 5-10 membered heteroaryl;

$R_d$ is each independently hydrogen, halogen, cyano, C1-C6 alkyl, —O—(C1-C6 alkyl), —O—(C3-C6 cycloalkyl), C3-C6 cycloalkyl, or 5-10-membered heteroaryl, and the alkyl, cycloalkyl, and heteroaryl are optionally substituted by one or more groups selected from halogen, hydroxyl, or amino;

n is 1, 2, 3 or 4;

$R_e$ is hydrogen or C1-C6 alkyl;

$R_c$ is hydrogen, —O—(C1-C6 alkyl), —O—(C3-C8 cycloalkyl), —O-(3-8-membered heterocycloalkyl), —O-aryl, —O-heteroaryl, —N(C1-C6 alkyl)$_{1-2}$, —NH (C3-C8 cycloalkyl), —NH (3-8-membered heterocycloalkyl), —NH-aryl, —NH-heteroaryl, C1-C6 alkyl, C2-C6 alkenyl, C2-C6 alkynyl, C3-C8 cycloalkyl, 3-8 membered heterocycloalkyl, 6-10 membered aryl or 5-10 membered heteroaryl, and the alkyl, cycloalkyl, heterocycloalkyl, aryl and heteroaryl are optionally substituted by one or more groups independently selected from hydroxyl, amino, halogen or cyano;

$R_b$ is hydrogen, —O—(C1-C6 alkyl), —O—(C3-C8 cycloalkyl), —O-(3-8-membered heterocycloalkyl), —O-aryl, —O-heteroaryl, —N(C1-C6 alkyl)$_{1-2}$, —NH (C3-C8 cycloalkyl), —NH (3-8-membered heterocycloalkyl), —NH-aryl, —NH-heteroaryl, C1-C6 alkyl, C2-C6 alkenyl, C2-C6 alkynyl, C3-C8 cycloalkyl, 3-8 membered heterocycloalkyl, 6-10 membered aryl or 5-10 membered heteroaryl, and the alkyl, cycloalkyl, heterocycloalkyl, aryl and heteroaryl are optionally substituted by one or more groups independently selected from hydroxyl, amino, halogen or cyano;

ring B is 3-12-membered heterocycloalkyl containing 1-2 heteroatoms selected from N, O or S, and the heterocycloalkyl is optionally substituted by a substituent selected from halogen, oxo, cyano, amino, hydroxyl, C1-C6 alkyl, C1-C6 haloalkyl, C1-C6 hydroxyalkyl or —O—(C1-C6 alkyl);

ring C is 3-12-membered heterocycloalkyl containing 1-2 heteroatoms selected from N, O or S, and the heterocycloalkyl is optionally substituted by a substituent selected from halogen, oxo, cyano, amino, hydroxyl, C1-C6 alkyl, C1-C6 haloalkyl, C1-C6 hydroxyalkyl or —O—(C1-C6 alkyl);

X is bond;

W is $—CR_gR_h$ or —C(O);

$R_g$ and $R_h$ are each independently hydrogen, halogen, C1-C4 alkyl, C1-C4 chloroalkyl, C1-C4 hydroxyalkyl or C3-C6 cycloalkyl;

L is $—(CH_2)_j—$;

j is 1, 2, 3, 4, 5 or 6.

More preferably, in some embodiments of the present invention, the compound of formula I is selected from:

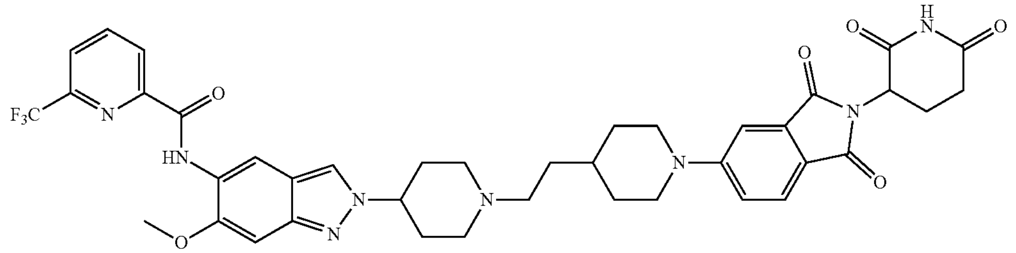

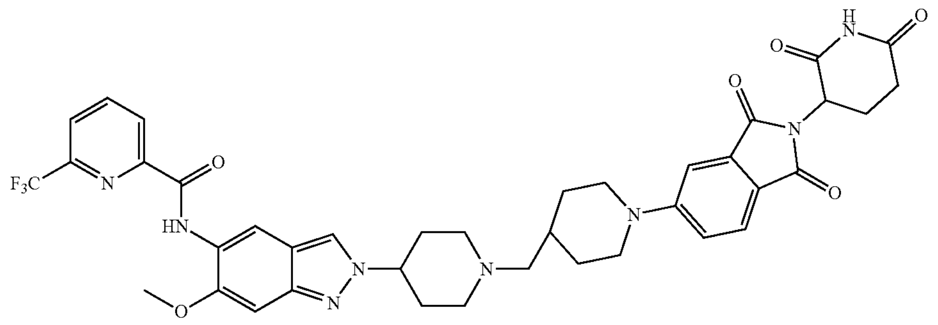

-continued
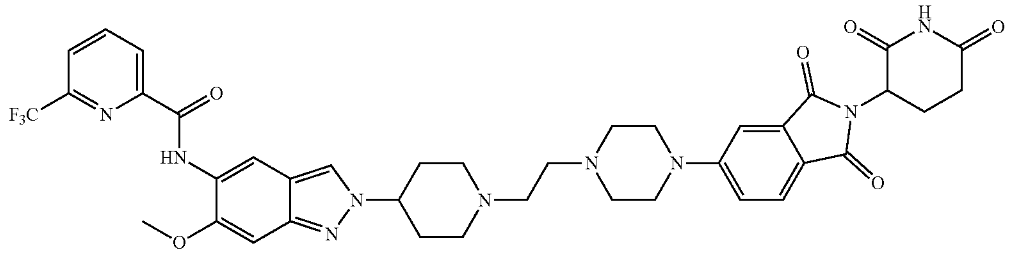
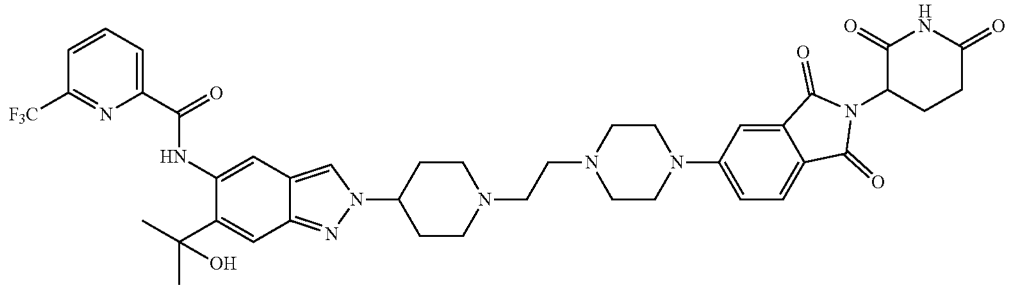
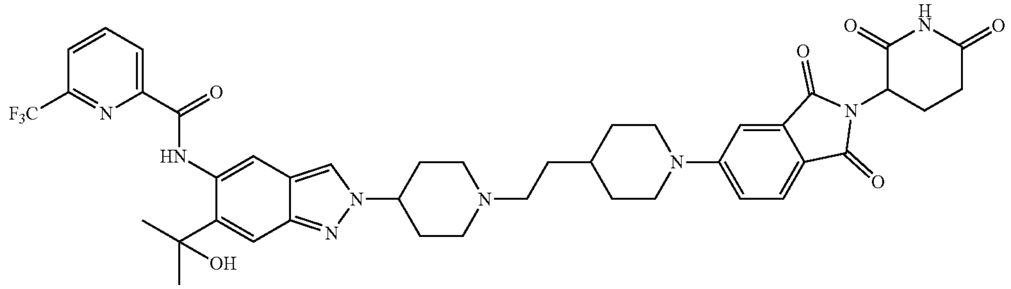
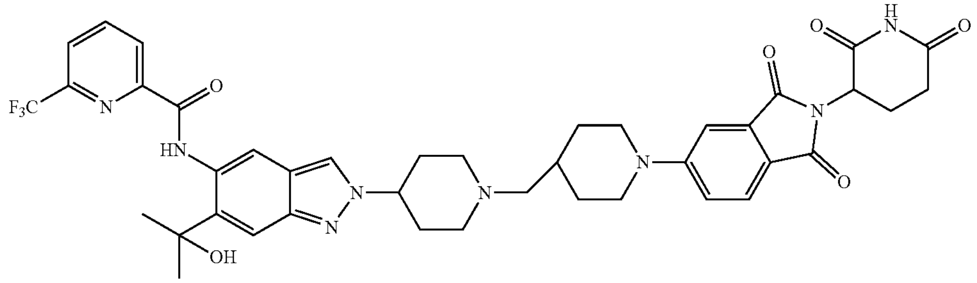
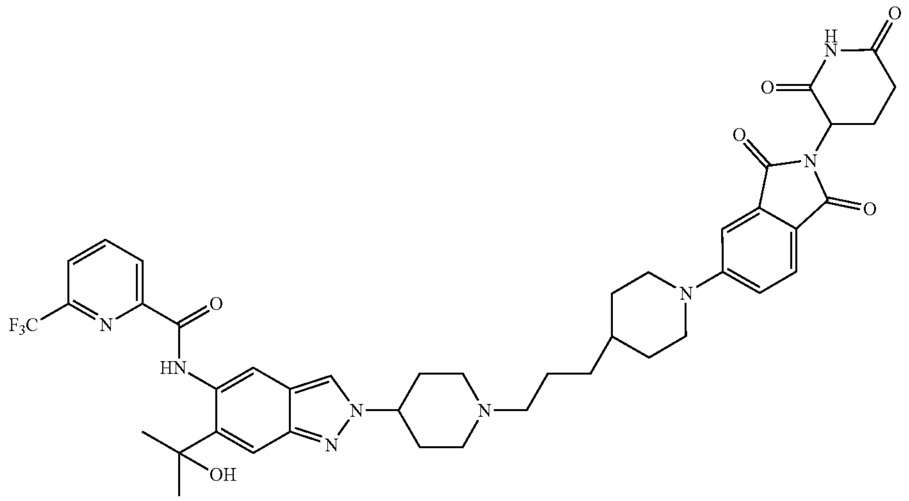

-continued
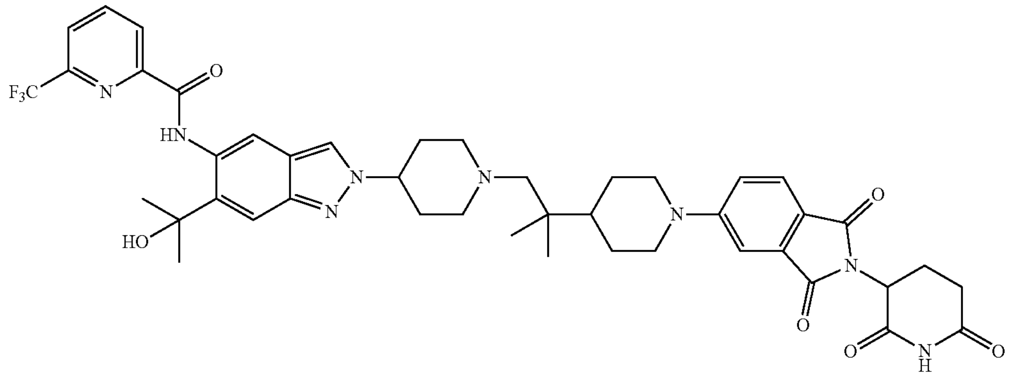
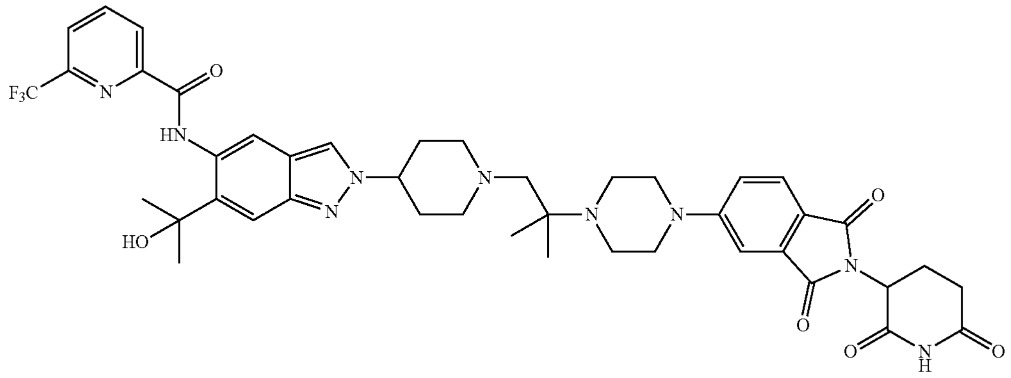
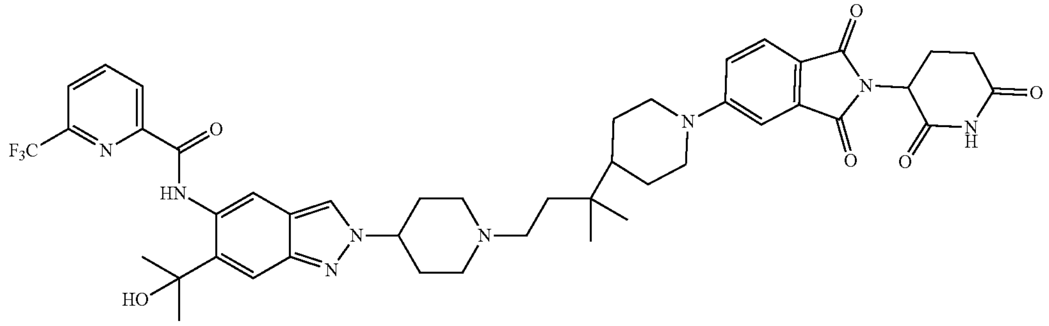
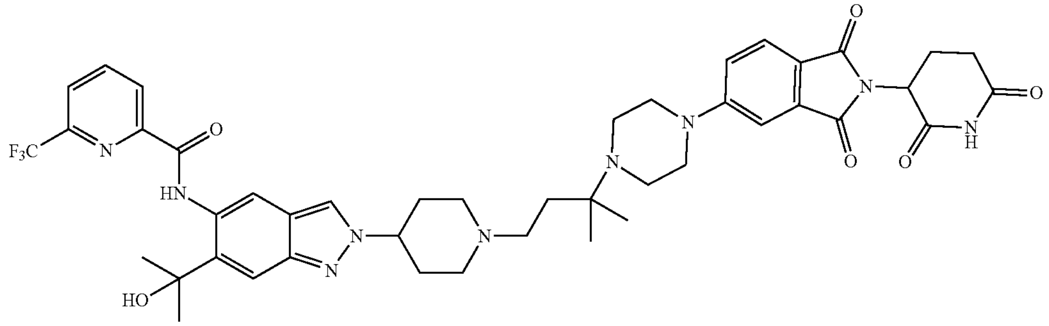
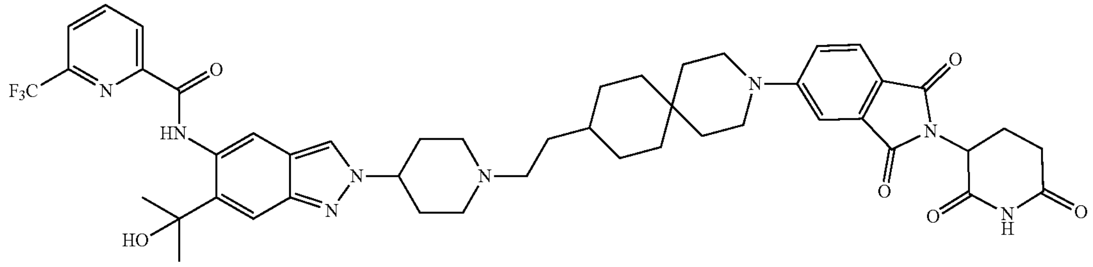

-continued

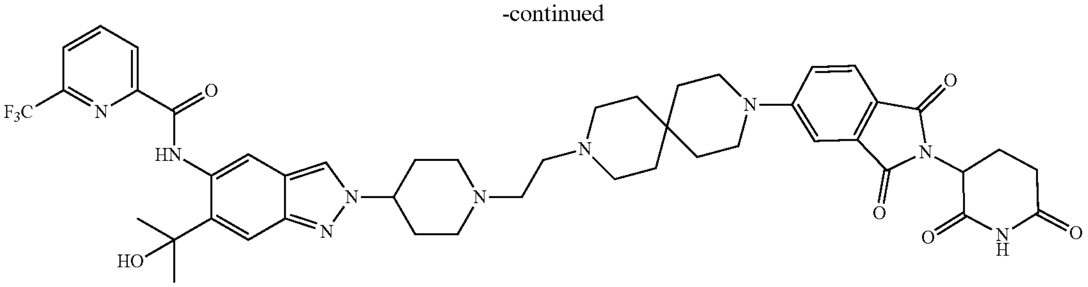

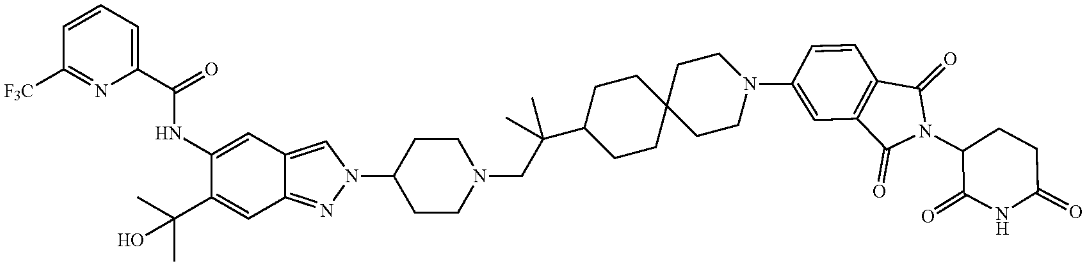

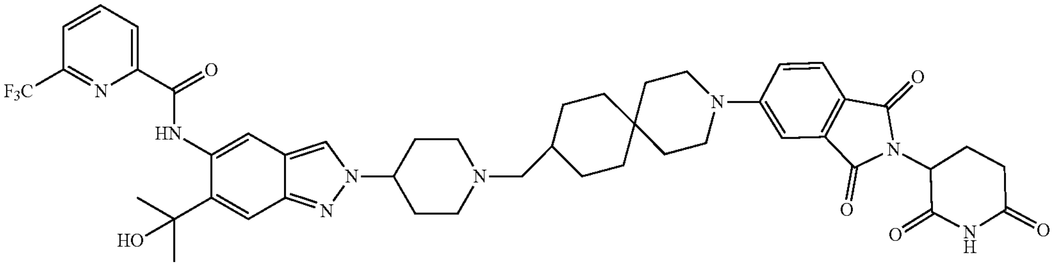

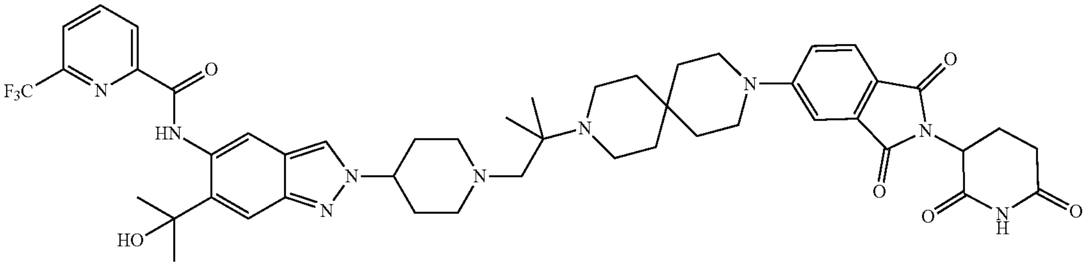

The invention provides a preparation method for the compound of formula I, and/or its stereoisomer, enantiomer, diastereomer, deuterate, hydrate, solvate, metabolite, prodrug and/or pharmaceutically acceptable salt.

The invention provides a pharmaceutical composition, comprising a therapeutically effective amount of the compound of formula I, and/or its stereoisomer, enantiomer, diastereomer, deuterate, hydrate, solvate, metabolite, prodrug and/or pharmaceutically acceptable salt, and a pharmaceutically acceptable carrier, diluent or excipient.

The present invention provides a method for degrading an IRAK4 protein comprising contacting the compound of formula I, and/or its stereoisomer, enantiomer, diastereomer, deuterate, hydrate, solvate, metabolite, prodrug and/or pharmaceutically acceptable salt, or its pharmaceutical composition with an IRAK4 protein.

The compound of formula I of the present invention, and/or its stereoisomer, enantiomer, diastereomer, deuterate, hydrate, solvate, metabolite, prodrug and/or pharmaceutically acceptable salt, or its pharmaceutical composition is used as a drug for the treatment or prevention of IRAK4-mediated diseases or conditions.

The compound of formula I of the present invention, and/or its stereoisomer, enantiomer, diastereomer, deuterate, hydrate, solvate, metabolite, prodrug and/or pharmaceutically acceptable salt, or its pharmaceutical composition is used as a drug for the treatment or prevention of diseases or conditions mediated by TLR (other than TLR3R), or IL-1β receptor family (including IL-1R, IL-18R, IL-33R, IL-36R).

The compound of formula I of the present invention, and/or its stereoisomer, enantiomer, diastereomer, deuterate, hydrate, solvate, metabolite, prodrug and/or pharmaceutically acceptable salt, or its pharmaceutical composition is used as a drug for the treatment or prevention of IRAK4-mediated diseases or conditions, which are diseases or conditions driven by MyD88.

The invention provides a use of the compound of formula I, and/or its stereoisomer, enantiomer, diastereomer, deuterate, hydrate, solvate, metabolite, prodrug and/or pharmaceutically acceptable salt, or its pharmaceutical composition in the preparation of drugs for the treatment or prevention of IRAK4-mediated diseases or conditions.

The invention provides a use of the compound of formula I, and/or its stereoisomer, enantiomer, diastereomer, deuterate, hydrate, solvate, metabolite, prodrug and/or pharmaceutically acceptable salt, or its pharmaceutical composition in the preparation of drugs for the treatment or prevention of diseases or conditions mediated by TLR (other than TLR3R), or IL-1β receptor family (including IL-1R, IL-18R, IL-33R, IL-36R).

The invention provides a use of the compound of formula I, and/or its stereoisomer, enantiomer, diastereomer, deuterate, hydrate, solvate, metabolite, prodrug and/or pharmaceutically acceptable salt, or its pharmaceutical composition in the preparation of drugs for the treatment or prevention of diseases or conditions regulated by IRAK4, and the IRAK4-mediated disease or condition is a disease or condition driven by MyD88.

The invention provides a use of the compound of formula I, and/or its stereoisomer, enantiomer, diastereomer, deuterate, hydrate, solvate, metabolite, prodrug and/or pharmaceutically acceptable salt, or its pharmaceutical composition in the preparation of drugs for the treatment or prevention of cancer, neurodegenerative diseases, viral diseases, autoimmune diseases, inflammatory diseases, hereditary diseases, hormone-related diseases, metabolic diseases, organ transplantation-related diseases, immunodeficiency diseases, destructive bone diseases, proliferative disorders, infectious diseases, conditions related to cell death, thrombin-induced platelet aggregation, liver diseases, pathological immune conditions involving T cell activation, cardiovascular diseases or CNS diseases.

The invention provides a use of the compound of formula I, and/or its stereoisomer, enantiomer, diastereomer, deuterate, hydrate, solvate, metabolite, prodrug and/or pharmaceutically acceptable salt, or its pharmaceutical composition in the preparation of drugs for the treatment or prevention of cancer or proliferative disease, and the cancer or proliferative disease is brain cancer, kidney cancer, liver cancer, adrenal cancer, bladder cancer, breast cancer, gastric cancer, ovarian cancer, colon cancer, rectal cancer, prostate cancer, pancreatic cancer, lung cancer, vaginal cancer, cervical cancer, testicular cancer, urogenital cancer, esophageal cancer, laryngeal cancer, skin cancer, bone cancer, thyroid cancer, sarcoma, neuroglioblastoma, neuroblastoma, multiple myeloma, gastrointestinal cancer, neck or head tumor, epidermal hyperproliferation, psoriasis, prostatic hyperplasia, adenoma, adenocarcinoma, keratoacanthoma, epidermoid cancer, large cell carcinoma, non-small cell lung cancer, lymphoma, Hodgkin's and non-Hodgkin's, breast cancer, follicular cancer, undifferentiated tumor, papillary tumor, seminoma, melanoma, ABC DLBCL, Hodgkin's lymphoma, primary cutaneous T-cell lymphoma, chronic lymphocytic leukemia, smoldering indolent multiple myeloma, leukemia, diffuse large B-cell lymphoma (DLBCL), chronic lymphocytic leukemia (CLL), chronic lymphocytic lymphoma, primary exudative lymphoma, Burkitt lymphoma/leukemia, acute lymphocytic leukemia, B-cell prolymphocytic leukemia, lymphoplasmacytic lymphoma, Waldenstroms's macroglobulinemia (WM), splenic marginal zone lymphoma, multiple myeloma, or plasmacytoma or intravascular large B-cell lymphoma.

The invention provides a use of the compound of formula I, and/or its stereoisomer, enantiomer, diastereomer, deuterate, hydrate, solvate, metabolite, prodrug and/or pharmaceutically acceptable salt, or its pharmaceutical composition in the preparation of drugs for the treatment or prevention of neurodegenerative disease, and the neurodegenerative disease is neurodegenerative disease caused by Alzheimer's disease, Parkinson's disease, amyotrophic lateral sclerosis, Huntington's disease, cerebral ischemia or traumatic injury, glutamate neurotoxicity, hypoxia, epilepsy, diabetes treatment, metabolic syndrome, obesity, organ transplantation or graft-versus-host disease.

The invention provides a use of the compound of formula I, and/or its stereoisomer, enantiomer, diastereomer, deuterate, hydrate, solvate, metabolite, prodrug and/or pharmaceutically acceptable salt, or its pharmaceutical composition in the preparation of drugs for the treatment or prevention of inflammatory disease, and the inflammatory disease is eye disease, such as eye allergy, conjunctivitis, dry eye or spring conjunctivitis, diseases affecting the nose, including allergic rhinitis; autoimmune hematological diseases, such as hemolytic anemia, aplastic anemia, pure red blood cell anemia and idiopathic thrombocytopenia, systemic lupus erythematosus, rheumatoid arthritis, polychondritis, scleroderma, dermatomyositis, chronic active hepatitis, myasthenia gravis, Stephen-Johnson syndrome, idiopathic stomatitis diarrhea, autoimmune inflammatory bowel disease, bowel syndrome, celiac disease, root periostitis, lung hyaline membrane disease, nephropathy, glomerular disease, Alcoholic liver disease, multiple sclerosis, endocrine ophthalmopathy, Grave's disease, Sarcomatosis, dry eye, spring conjunctival keratitis, interstitial pulmonary fibrosis, psoriatic arthritis, systemic juvenile idiopathic arthritis, nephritis, vasculitis, interstitial cystitis, diverticulitis, Glomerulonephritis, chronic granulomatous disease, endometriosis, leptospirosis nephropathy, glaucoma, retinal disease, aging, headache, pain, complex regional pain syndrome, cardiac hypertrophy, muscle atrophy, catabolism, obesity, slow fetal growth, hypercholesterolemia, heart disease, chronic heart failure, mesothelioma, anhidromic ectodermal dysplasia, Behcet's disease, pigment incontinence, Paget's disease, pancreatitis, hereditary periodic fever syndrome, asthma, acute lung injury, acute respiratory distress syndrome, eosinophilia, allergic reaction, systemic allergic reaction, sinusitis, eye allergy, silica-induced diseases, COPD, lung disease, cystic fibrosis, liver fibrosis, renal fibrosis, alcoholic fatty liver, non-alcoholic fatty liver, heart fibrosis, psoriasis, Crohn's disease, inflammatory bowel disease, acid-induced lung injury, pulmonary hypertension, polyneuropathy, Cataract, muscle inflammation combined with systemic sclerosis, inclusion body myositis, myasthenia gravis, thyroiditis, Addison's disease, lichen planus, type 1 diabetes, type 2 diabetes, appendicitis, atopic dermatitis, asthma, allergies, bronchiolitis, bronchitis, bursitis, cervicitis, cholangitis, cholecystitis, chronic transplant rejection, colitis, conjunctivitis, cystitis, lacrimal gland inflammation, dermatitis, dermatomyositis, encephalitis, endocarditis, Endometritis, enteritis, enterocolitis, upper ankle inflammation, epididymitis, fasciitis, fibrous tissue inflammation, gastritis, gastroenteritis, Henoch-Schonlein purpura, hepatitis, suppurative sweat inflammation, immunoglobulin A nephropathy, interstitial lung disease, laryngitis, mastitis, meningitis, myelitis, myocarditis, myositis, nephritis, oophoritis, orchitis, osteitis, otitis, pancreatitis, mumps, pericarditis, peritonitis, pharyngitis, pleurisy, phlebitis, local pneumonia, pneumonia, polymyositis, proctitis, prostatitis, pyelonephritis, rhinitis, salpingitis, sinusitis, stomatitis, articular inflammation, tendinitis, tonsillitis, ulcerative colitis, uveitis, vaginitis, vasculitis, vulvitis, alopecia areata, erythema multiforme, dermatitis herpetiformis, sclerosis, vitiligo, hypersensitivity vasculitis, urticaria, bullous pemphigoid, pemphigus vulgaris, deciduous pemphigus, paraneoplastic pemphigus, acquired bullous epidermal laxity, acute and chronic gout, chronic gouty arthritis, psoriasis, psoriasis arthritis, rheumatoid arthritis, juvenile rheumatoid arthritis, cryopyrin-associated periodic syndrome or osteoarthritis.

The invention provides a method for treating or preventing IRAK4-mediated diseases or conditions, including administrating a therapeutically effective amount of the compound of formula I, and/or its stereoisomer, enantiomer, diastereomer, deuterate, hydrate, solvate, metabolite, prodrug and/or pharmaceutically acceptable salt, or its pharmaceutical composition to a subject in need thereof.

The invention provides a method for treating or preventing IRAK4-mediated diseases or conditions, including administrating a therapeutically effective amount of the compound of formula I, and/or its stereoisomer, enantiomer, diastereomer, deuterate, hydrate, solvate, metabolite, prodrug and/or pharmaceutically acceptable salt, or its pharmaceutical composition to a subject in need thereof, and the IRAK4-mediated disease or condition is a disease or condition driven by MyD88.

The invention provides a method for the treatment or prevention of diseases or conditions mediated by TLR (other than TLR3R) or IL-1 receptor family (including IL-1R, IL-18R, IL-33R, IL-36R), including administrating a therapeutically effective amount of the compound of formula I, and/or its stereoisomer, enantiomer, diastereomer, deuterate, hydrate, solvate, metabolite, prodrug and/or pharmaceutically acceptable salt, or its pharmaceutical composition to a subject in need thereof.

The invention provides a preparation method for the compound of formula I, and/or its stereoisomer, enantiomer, diastereomer, deuterate, hydrate, solvate, metabolite, prodrug and/or pharmaceutically acceptable salt:

method 1

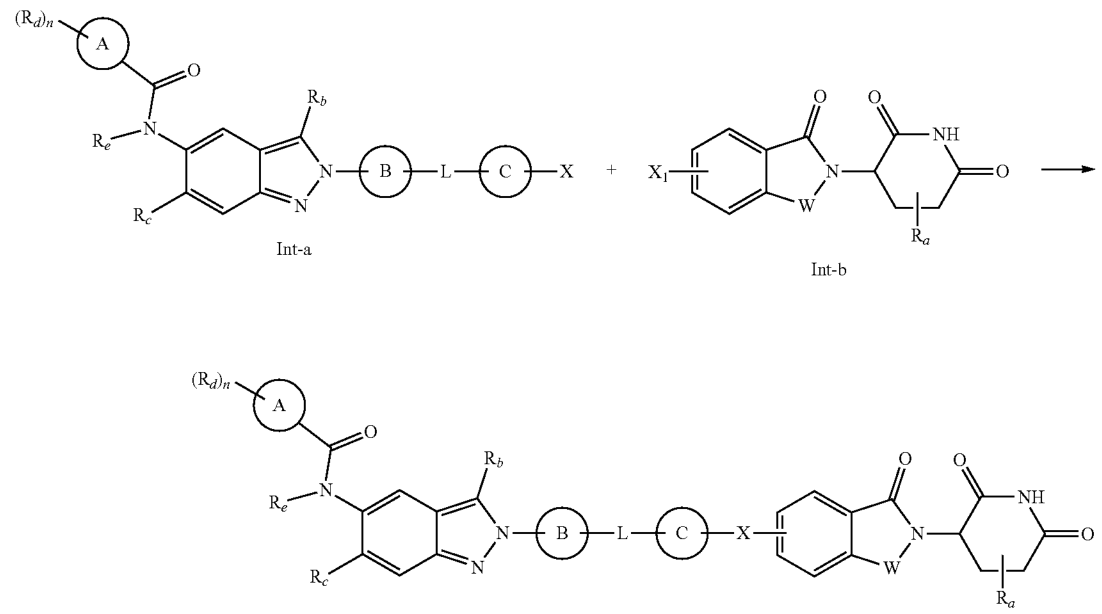

Int-a

Int-b

I

Intermediate Int-a and intermediate Int-b undergo substitution reaction under basic conditions to obtain the compound of formula I. The base is an inorganic base or an organic base, including, but not limited to, triethylamine, N,N-diisopropylethyl amine, potassium carbonate, sodium carbonate, and sodium bicarbonate. $X_1$ is halogen; preferably F. $R_a$, $R_b$, $R_c$, $R_d$, $R_e$, n, ring A, ring B, L, ring C, X, and W are as defined above.

method 2

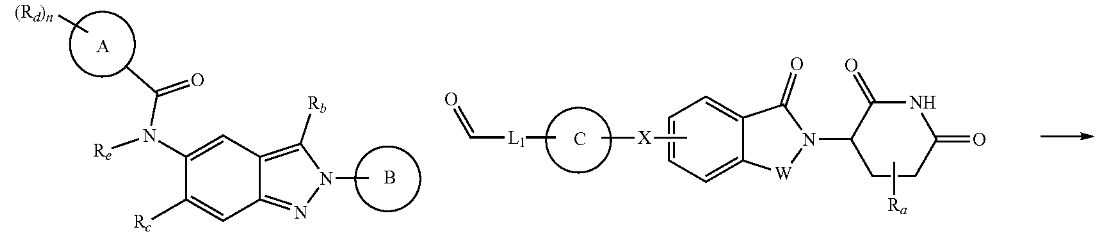

Int-c

Int-d

-continued

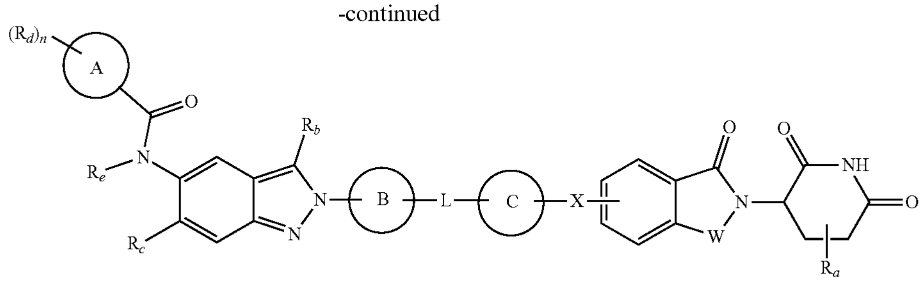

I

Intermediate Int-c and Intermediate Int-d undergo a reductive amination reaction to obtain the compound of formula I. The reducing reagents for reducing amination include, but are not limited to, Pd/C, sodium borohydride, sodium cyanoborohydride, borane, and sodium triacetoxyl borohydride. Wherein, $L_1$ is —$(CH_2)_{j-1}$, and the methylene in —$(CH_2)_{j-1}$ is as defined in above L, optionally replaced by one or more groups. $R_a$, $R_b$, $R_c$, $R_d$, $R_e$, n, ring A, ring B, ring C, X, and W are as defined above.

method 3

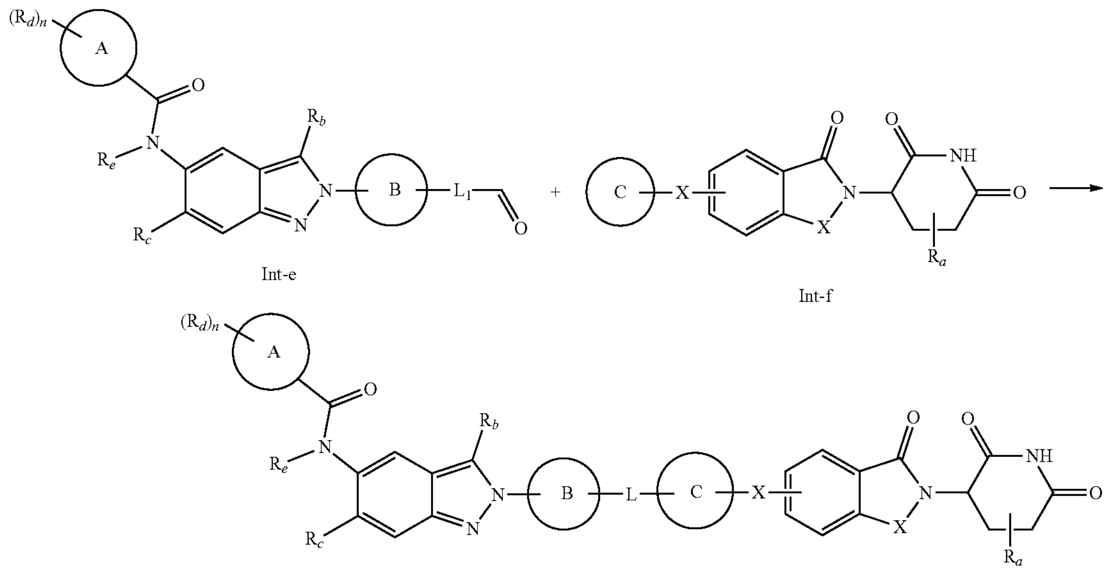

Int-e

Int-f

I

Intermediate Int-e and intermediate Int-f undergo a reductive amination reaction to obtain the compound of formula I. The reducing reagents for reducing amination include, but are not limited to, Pd/C, sodium borohydride, sodium cyanoborohydride, borane, and sodium triacetoxyl borohydride. Wherein, $L_1$ is —$(CH_2)_{j-1}$, and the methylene in —$(CH_2)_{j-1}$ is as defined in above L, optionally replaced by one or more groups. $R_a$, $R_b$, $R_c$, $R_a$, $R_e$, n, ring A, ring B, ring C, X, and W are as defined above.

DETAILED DESCRIPTION

Unless stated to the contrary, the following terms used in the specification and claims have the following meanings.

"Alkyl" refers to saturated aliphatic hydrocarbon groups, including linear or branched alkyls; C1-C8 alkyl refers to alkyl containing 1-8 carbon atoms, for example, methyl, ethyl, n-propyl, isopropyl, n-butyl, isobutyl, tert-butyl, sec-butyl, n-amyl, 1, 1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1, 1, 2-trimethylpropyl, 1,1-dimethylbutyl, 1,2-dimethylbutyl, 2,2-dimethylbutyl, 1, 3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl or its various branched isomers; preferably C1-C6 alkyl; more preferably C1-C4 alkyl. The alkyl may be substituted or unsubstituted.

"Cycloalkyl" refers to saturated or partially unsaturated monocyclic or polycyclic hydrocarbon substituents; "C3-C11 cycloalkyl" refers to cycloalkyl containing 3 to 11 carbon atoms; "C3-C8 cycloalkyl" refers to cycloalkyl containing 3 to 8 carbon atoms; "C5-C10 cycloalkyl" refers to cycloalkyl containing 5 to 10 carbon atoms;

Non-limiting examples of monocycloalkyl comprise cyclopropyl, cyclobutyl, cyclopentyl, cyclopentenyl, cyclohexyl, cyclohexenyl, cyclohexadienyl, cycloheptyl, cycloheptatrienyl, cyclooctyl, etc., preferably cyclopropyl, cyclobutyl, cyclopentyl, cyclohexyl; preferably C3-C8 cycloalkyl; more preferably C3-C6 cycloalkyl.

Polycyclic cycloalkyls include spiro, fused and bridged cycloalkyls. "Spiro cycloalkyl" refers to a polycyclic group that shares a carbon atom (called a spiro atom) between monocyclyls. They can contain one or more double bonds, but none of the rings have a fully conjugated π electronic system. According to the number of spiro atoms shared between the rings, the spiro alkyl is divided into single spiro cycloalkyl, double spiro cycloalkyl or polyspiro cycloalkyl, preferably 7-12 membered double spiro cycloalkyl. Non-limiting examples of spiro cycloalkyl include:

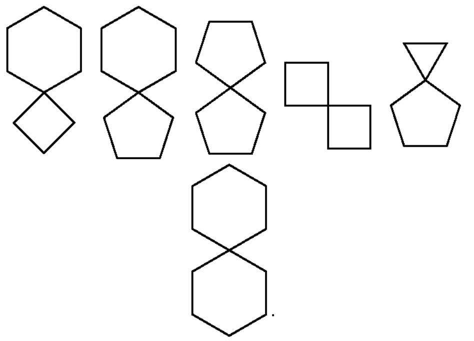

"Fused cycloalkyl" refers to an all-carbon polycyclic group in which each ring in the system shares an adjacent pair of carbon atoms with the other rings in the system, wherein one or more rings may contain one or more double bonds, but none of them has a fully conjugated π-electron system. According to the number of constituent rings, it can be divided into bicyclic, tricyclic, tetracyclic or polycyclic fused cycloalkyl, preferably bicyclic fused cycloalkyl. Non-limiting examples of fused cycloalkyl include:

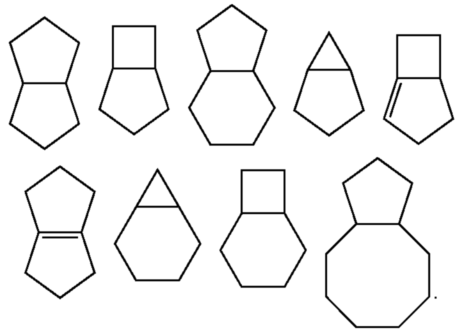

"Bridged cycloalkyl" refers to an all-carbon polycyclic group in which any two rings share two carbon atoms that are not directly connected, they can contain one or more double bonds, but no ring has a fully conjugated π electron system. According to the number of constituent rings, it can be divided into bicyclic, tricyclic, tetracyclic or polycyclic bridged cycloalkyl. Non-limiting embodiments of bridged cycloalkyl include:

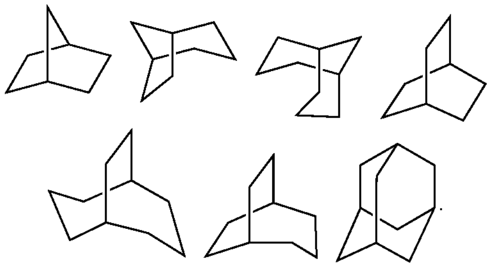

The cycloalkyl ring may be fused to an aryl, heteroaryl or heterocycloalkyl ring, wherein the ring connected to the parent structure is a cycloalkyl, and non-limiting examples include indanyl, tetrahydronaphthyl, benzocycloheptyl, etc. The cycloalkyl may be optionally substituted or unsubstituted.

"Heterocycloalkyl" refers to a saturated or partially unsaturated monocyclic or polycyclic hydrocarbon substituent, wherein one or more ring atoms are selected from nitrogen, oxygen, or S(O)r (wherein r is an integer of 0, 1 or 2), but do not contain the ring moieties of —O—O—, —O—S— or —S—S—, and the remaining ring atoms are carbon. "3-11-membered heterocycloalkyl" refers to a cyclyl containing 3 to 11 ring atoms, "5-10-membered heterocycloalkyl" refers to a cyclyl containing 5 to 10 ring atoms, and "3-8-membered heterocycloalkyl" refers to a cyclyl containing 3 to 8 ring atoms, preferably "3-11-membered heterocycloalkyl" containing 1-2 heteroatoms selected from N, O or S, more preferably a 3-11-membered heterocycloalkyl containing 1 or 2 N atoms.

The monocyclic heterocycloalkyl is preferably a 3-8 membered monocyclic heterocyclyl containing 1-2 N heteroatoms; non-limiting examples of monocyclic heterocycloalkyl include pyrrolidyl, piperidinyl, piperazinyl, morpholinyl, thiomorpholinyl, homopiperazinyl, etc., preferably piperidinyl and piperazinyl.

Polycyclic heterocycloalkyls include spiro, fused and bridged heterocycloalkyls. "Spiro heterocycloalkyl" refers to a polycyclic heterocycloalkyl that shares one atom (called a spiro atom) between single rings, wherein one or more ring atoms are selected from nitrogen, oxygen or S(O)r (wherein r is an integer of 0, 1, 2), and the remaining ring atoms are carbon. They can contain one or more double bonds, but none of the rings have a fully conjugated π-electron system. According to the number of spiro atoms shared between the rings, the spiro cycloalkyl is divided into mono-spiro heterocycloalkyl, bis-spiro heterocycloalkyl or polyspiro heterocycloalkyl, preferably saturated "3-11 membered bis-spiro heterocycloalkyl" containing 1-2 heteroatoms selected from N, O or S; more preferably saturated "7-12 membered bis-spiro heterocycloalkyl" containing 1 or 2 N atoms. Non-limiting examples of spiro heterocycloalkyl include:

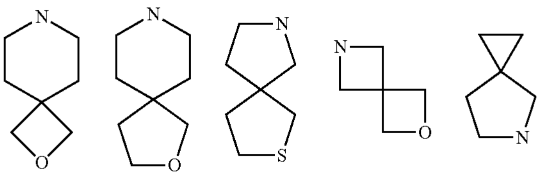

-continued

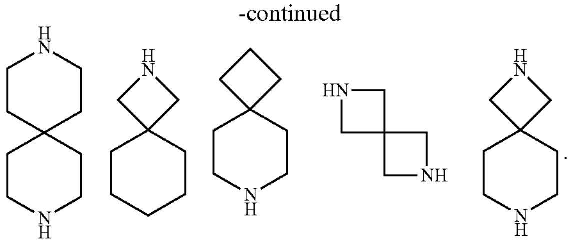

"Fused heterocycloalkyl" refers to a polycyclic heterocycloalkyl in which each ring in the system shares an adjacent pair of atoms with other rings in the system, wherein one or more rings may contain one or more double bonds, but none of them has a fully conjugated π-electron system, wherein one or more ring atoms are selected from nitrogen, oxygen, or S(O)r (wherein r is an integer of 0, 1, 2), the remaining ring atoms are carbon. According to the number of constituent rings, it can be divided into bicyclic, tricyclic, tetracyclic or polycyclic fused heterocycloalkyl, preferably "3-11-membered bicyclic fused heterocycloalkyl" containing 1 to 3 heteroatoms selected from N, O or S; more preferably saturated "3-11-membered bicyclic fused heterocycloalkyl" containing 1 or 2 N atoms. Non-limiting examples of fused heterocycloalkyl include:

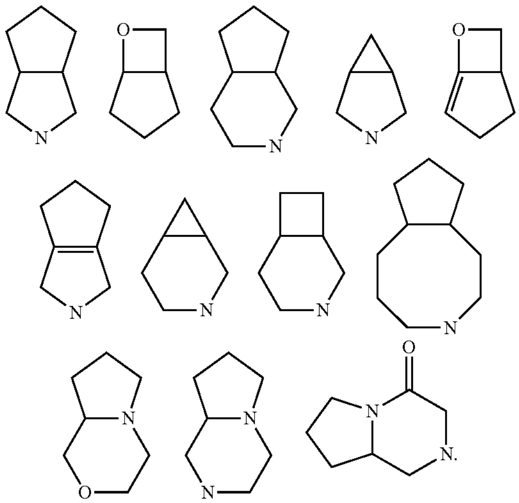

"Bridged heterocycloalkyl" refers to a polycyclic heterocycloalkyl in which any two rings share two atoms that are not directly connected. They can contain one or more double bonds, but no ring has a fully conjugated π electron system, wherein one or more ring atoms are selected from nitrogen, oxygen or S(O)r (wherein r is an integer of 0, 1, 2), and the remaining ring atoms are carbon. According to the number of constituent rings, it can be divided into bicyclic, tricyclic, tetracyclic or polycyclic bridged cycloalkyl. The non-limiting examples of bridged heterocycloalkyl include.

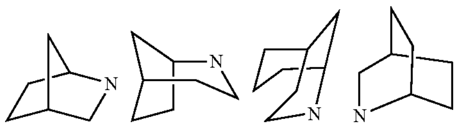

-continued

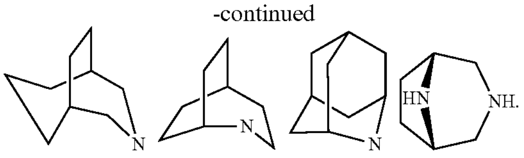

The heterocycloalkyl ring can be fused to an aryl, heteroaryl or cycloalkyl, wherein the ring connected with the parent structure is heterocycloalkyl, non-limiting examples include:

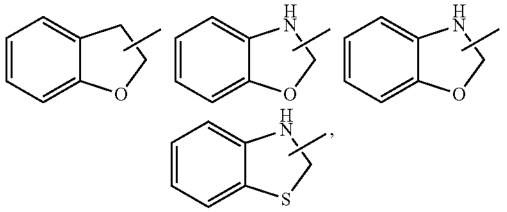

and the heterocycloalkyl may be optionally substituted or unsubstituted.

"Aryl" refers to all-carbon monocyclyls or fused polycyclyls (that is, rings sharing adjacent pairs of carbon atoms) and polycyclyls having conjugated π-electron systems, and "6-10-membered aryl" refers to all-carbon aryls containing 6-10 carbons, such as phenyl and naphthyl; preferably phenyl. The aryl ring may be fused to the heteroaryl, heterocycloalkyl or cycloalkyl, wherein the ring connected with the parent structure is an aryl ring, and the non-limiting examples include:

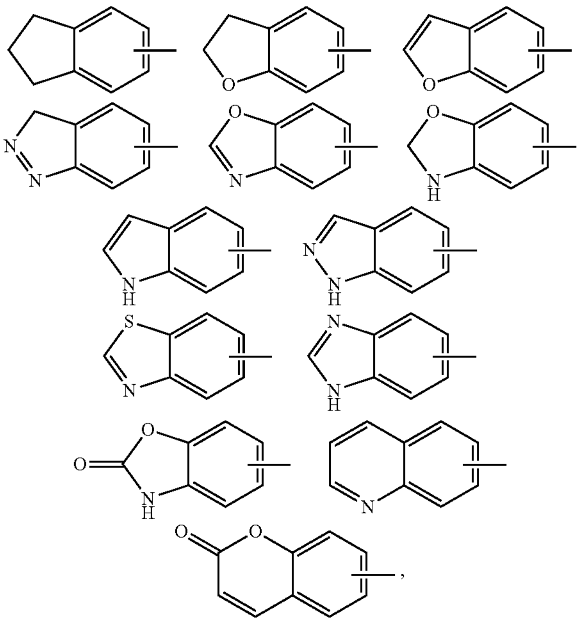

and the aryl may be optionally substituted or unsubstituted.

"Heteroaryl" refers to a heteroaromatic system containing 1 to 4 heteroatoms, the heteroatoms include nitrogen, oxygen or S(O)r (wherein r is an integer of 0, 1, 2), 5-6-membered heteroaryl refers to a heteroaromatic system containing 5 to 6 ring atoms, and 5-10-membered heteroaryl refers to a heteroaromatic system containing 5 to 10 ring atoms, preferably 5-6-membered heteroaryl; more preferably a 5-6-membered heteroaryl containing 1 or 2 N atoms; non-limiting examples include furyl, thienyl, pyridyl, pyrrolyl, N-alkylpyrrolyl, pyrimidyl, pyrazinyl, pyrazolyl, imidazolyl, triazolyl, tetrazolyl, etc.; preferably pyridyl. The heteroaryl ring may be fused to an aryl, heterocycloalkyl or cycloalkyl, wherein the ring connected with the parent structure is a heteroaryl, and the non-limiting examples include:

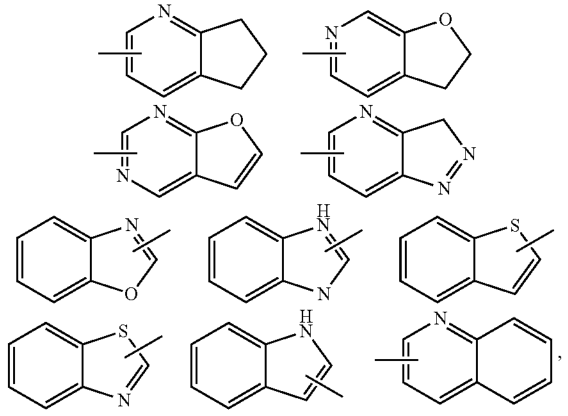

and the heteroaryl may be optionally substituted or unsubstituted.

"Alkenyl" refers to an alkyl as defined above consisting of at least two carbon atoms and at least one carbon-carbon double bond, and "C2-8 alkenyl" refers to a linear or branched alkenyl containing 2-8 carbons, including but not limited to vinyl, 1-propenyl, 2-propenyl, 1-, 2- or 3-butenyl, etc., preferably "C2-6 alkenyl", more preferably "C2-4 alkenyl". The alkenyl may be substituted or unsubstituted.

"Alkynyl" refers to an alkyl as defined above consisting of at least two carbon atoms and at least one carbon-carbon triple bond, and "C2-8 alkynyl" refers to a linear or branched alkynyl containing 2-8 carbons, including but not limited to ethynyl, 1-propynyl, 2-propynyl, 1-, 2- or 3-butynyl, preferably "C2-6 alkynyl", more preferably "C2-4 alkynyl". The alkynyl may be substituted or unsubstituted.

"Subgroup" refers to a divalent, such as alkylene refers to divalent alkyl, alkenylene refers to divalent alkenyl, alkynylene refers to divalent alkynyl, cycloalkylene refers to divalent cycloalkyl, heterocycloalkylene refers to divalent heterocycloalkyl, arylene refers to divalent aryl, heteroarylene refers to divalent heteroaryl, and the alkyl, alkenyl, alkynyl, cycloalkyl, heterocycloalkyl, aryl, heteroaryl are as defined above, the subgroups may be optionally substituted or unsubstituted.

"Haloalkyl" refers to an alkyl substituted by one or more fluorine, chlorine, bromine or iodine atoms, wherein the alkyl is as defined above, and non-limiting examples include difluoromethyl, dichloromethyl, dibromomethyl, trifluoromethyl, trichloromethyl, tribromomethyl, etc.

"Hydroxyalkyl" refers to an alkyl optionally substituted by one or more —OH, wherein the alkyl is as defined above, and non-limiting examples include hydroxymethyl, hydroxyethyl, hydroxypropyl, hydroxyisopropyl.

"Cyano" refers to —CN.

"Amino" refers to $—NH_2$.

"Hydroxyl" refers to —OH.

"Carboxyl" or "carboxylic acid" refers to —COOH.

"Oxo" refers to =O.

"Halogen" refers to fluorine, chlorine, bromine or iodine.

"NMP" refers to N-methylpyrrolidone.

"IBX" refers to 2-iodoacyl benzoic acid.

"DIEA" refers to N,N-diisopropylethylamine.

"STAB" refers to sodium triacetoxylborohydride.

"$T_3P$" refers to 2,4, 6-tripropyl-1, 3,5,2,4, 6-trioxytriphosphate-2,4, 6-trioxide.

"DPBS" refers to Dulbecco's phosphate buffer saline.

"Dess-Martin" refers to Deiss-Martin reagent.

"PBS" refers to phosphate buffer saline.

"SDS-PAGE" refers to sodium dodecyl sulfate-polyacrylamide gel electrophoresis.

"PVDF" refers to polyvinylidene fluoride.

"More" refers to 2, 3, 4, 5, 6, etc., preferably fully substituted. For example, as for methyl, the substitution of more halogens (such as F) may refer to trifluoromethyl (F3C).

"Optionally" refers to that a subsequently described event or environment may, but does not have to, occur, and that description includes the place where the event or environment occurs or does not occur. For example, "a heterocycloalkyl optionally substituted by an alkyl" means that an alkyl may, but does not have to be present, and the description includes the case where the heterocycloalkyl is substituted by an alkyl and the case where the heterocycloalkyl is not substituted by an alkyl.

"Substituted" refers to that one or more hydrogen atoms, preferably at most 5, more preferably 1 to 3 hydrogen atoms are substituted independently of each other by a corresponding number of substituents. It goes without saying that the substituents are only in their possible chemical positions, and those skilled in the art can determine (experimentally or theoretically) possible or impossible substitutions without too much effort. For example, amino or hydroxyls with free hydrogen may be unstable when combined with carbon atoms with unsaturated (e.g. olefinic) bonds.

"Pharmaceutical composition" refers to a mixture comprising one or more compounds described herein or their physiologically/pharmaceutically acceptable salts or prodrugs with other chemical components, as well as other components such as physiologically/pharmaceutically acceptable carriers and excipients. The purpose of the pharmaceutical composition is to promote the administration of organisms, facilitate the absorption of active ingredients and thus exert biological activity.

The present invention also provides pharmaceutically acceptable salts of compounds of formula (I). The term "pharmaceutically acceptable salt" refers to an acid addition salt or a base addition salt of a compound of the present invention that is relatively non-toxic. The acid addition salts are salts of the compounds of formula (I) of the present invention and suitable inorganic or organic acids, these salts can be prepared during the final separation and purification of the compounds, or can be prepared by reacting the purified compounds of formula (I) in their free base form with suitable organic or inorganic acids. Representative acid addition salts include hydrobromate, hydrochloride, sulfate, bisulfate, sulfite, acetate, oxalate, valerate, oleate, palmitate, stearate, lauroleate, borate, benzoate, lactate, phosphate, hydrophosphate, carbonate, bicarbonate, toluate, citrate, maleate, fumarate, succinate, tartrate, benzoate, mesylate, p-toluene sulfonate, gluconate, lactobionate and lauryl sulfonate, etc. The base addition salt is a salt formed by a compound of formula (I) and a suitable inorganic or organic base, including, for example, a salt formed with alkali metals, alkaline earth metals, and quaternary ammonium cations, such as sodium salt, lithium salt, potassium salt, calcium salt, magnesium salt, tetramethylquaternary ammonium salt, tetraethyl quaternary ammonium salt, etc.; amine salt includes salts formed with ammonia ($NH_3$), primary amine, secondary amine or tertiary amine, such as methylamine salt, dimethylamine salt, trimethylamine salt, triethylamine salt, ethylamine salt, etc.

The compounds of the invention, or pharmaceutically acceptable salts thereof, can be administered to mammals, including humans, orally, rectally, parenterally (intravenously, intramuscularly or subcutaneously), topically (powder, ointment or drops), or intratumorally.

The dosage of the compound of the present invention may be about 0.05-300 mg/kg body weight/day, preferably 10-300 mg/kg body weight/day, more preferably 10-200 mg/kg body weight/day.

The compounds of the present invention, or pharmaceutically acceptable salts thereof, may be formulated as solid dosage forms for oral administration, including, but not limited to, capsules, tablets, pills, powders, granules, and the like. In these solid dosage forms, the active ingredient, i.e. the compound of formula (I) of the present invention, is mixed with at least one conventional inert excipient (or carrier), such as sodium citrate or dicalcium phosphate, or mixed with any of the following components: (1) fillers or compatibilizer, for example, starch, lactose, sucrose, glucose, mannitol and silicic acid, etc.; (2) binders, for example, hydroxymethyl cellulose, alginate, gelatin, polyvinylpyrrolidone, sucrose and arabic gum, etc.; (3) humectants, for example, glycerol, etc.; (4) disintegrating agents, for example, agar, calcium carbonate, potato starch or tapioca starch, alginic acid, certain composite silicates, and sodium carbonate, etc.; (5) dissolution-retarding agents, such as paraffin, etc.; (6) absorption accelerators, for example, quaternary ammonium compounds, etc.; (7) wetting agents, for example, cetyl alcohol and glyceryl monostearate, etc.; (8) adsorbents, for example, kaolin, etc.; and (9) lubricants, for example, talc, calcium stearate, magnesium stearate, solid polyethylene glycol, sodium lauryl sulfate, or the mixture thereof. Buffering agents may also be included in capsules, tablets and pills.

The solid dosage forms such as tablets, sugar pills, capsules, pills and granules can be coated or microencapsulated with coating and shell materials such as enteric coatings and other materials known in the art. They may contain opaque agents, and the release of the active ingredient in such a composition may be released in a delayed manner in a part of the digestive tract. Examples of embedding components that can be employed are polymeric materials and waxy materials. If necessary, the active ingredient may also form a microcapsule form with one or more of the excipients described above.

The compounds of the present invention, or pharmaceutically acceptable salts thereof, may be formulated as liquid dosage forms for oral administration, including, but not limited to, pharmaceutically acceptable emulsions, solutions, suspensions, syrups, tinctures, and the like. In addition to the compounds of formula (I) or pharmaceutically acceptable salts thereof as active ingredients, liquid dosage forms may contain inert diluents such as water and other solvents, solubilizers and emulsifiers, such as ethanol, isopropanol, ethyl carbonate, ethyl acetate, propylene glycol, 1,3-butanediol, dimethylformamide, and oils, especially cottonseed oil, peanut oil, corn germ oil, olive oil, castor oil and sesame oil or a mixture of these substances as conventionally used in the art. In addition to these inert diluents, the liquid dosage forms of the present invention may also contain conventional auxiliaries such as wetting agents, emulsifiers and suspending agents, sweeteners, flavoring agents and spices.

The suspending agent includes, for example, ethoxylated isooctadecanol, polyoxyethylene sorbitol and dehydrated sorbitol esters, microcrystalline cellulose, aluminum methanol and agar, or a mixture of these substances.

The compounds of the present invention, or pharmaceutically acceptable salts thereof, may be formulated as dosage forms for parenteral injection including, but not limited to, physiologically acceptable sterile aqueous or anhydrous solutions, dispersions, suspensions or emulsions, and sterile powders for re-dissolution into sterile injectable solutions or dispersions. Suitable carriers, diluents, solvents or excipients include water, ethanol, polyols and suitable mixtures thereof.

The compounds of the present invention, or pharmaceutically acceptable salts thereof, may also be formulated as dosage forms for topical administration, including, for example, ointments, powders, suppositories, drops, propellants, inhalants, and the like. The compounds of formula (I) of the invention, or pharmaceutically acceptable salts thereof, as active ingredient, are mixed with a physiologically acceptable carrier and an optional preservative, a buffer, or, if necessary, a propellant as may be required under sterile conditions.

The present invention also provides a pharmaceutical composition comprising a compound of formula (I) of the present invention or a pharmaceutically acceptable salt thereof as active ingredient, and a pharmaceutically acceptable carrier, excipient or diluent. In the preparation of pharmaceutical compositions, a compound of formula (I) or a pharmaceutically acceptable salt thereof is usually mixed with a pharmaceutically acceptable carrier, excipient or diluent.

The composition of the present invention can be formulated as a conventional pharmaceutical preparation according to the conventional preparation method. For example, tablets, pills, capsules, powders, granules, emulsions, suspensions, dispersions, solutions, syrups, elixirs, ointments, drops, suppositories, inhalants, propellants, etc.

The compound of the present invention or its pharmaceutically acceptable salt may be administered alone, or (if necessary) in combination with other pharmaceutically acceptable therapeutic agents, such as in combination with other anti-tumor drugs, anti-inflammatory drugs or autoimmune drugs. The ingredients to be combined may be administered simultaneously or sequentially, in the form of a single formulation or in the form of a different formulation. The combination may include not only a combination of a compound of the present invention and one other active agent, but also a combination of a compound of the present invention and two or more other active agents.

The present invention proves that the compound of formula I of the present invention can effectively bind to the IRAK4 target protein or produce an inhibitory effect through the IRAK4 kinase activity test experiment, and the compound of formula I of the present invention can effectively and specifically degrade the IRAK4 protein in THP-1 cells by Western-Blot; through the study of mouse pharmacokinetic properties, it is proved that the compound of the present invention has low clearance rate, high plasma exposure, and good oral bioavailability, and good pharmacokinetic properties; and the degradation experiment of IKZF1 and IKZF3 in L363 cells proves that the compound of the present invention has good selectivity. The compound of formula I of the present invention, and/or its stereoisomer, enantiomer, diastereomer, deuterate, hydrate, solvate, metabolite, prodrug and/or pharmaceutically acceptable salt can effectively degrade IRAK4 protein, so as to achieve the effect of preventing or treating IRAK4-related diseases or conditions.

EXAMPLES

Hereinafter, the present invention will be described in further detail and completely with reference to the examples, but the present invention is not in any way limited to the contents of the examples. The starting materials in the examples of the present invention are known and can be commercially available or can be synthesized using or in accordance with methods known in the art. In the absence of special instructions, in the present examples, the experimental method that does not specify the specific conditions, usually in accordance with the conventional conditions, or in accordance with the conditions suggested by raw material or commodity manufacturer.

I Examples for Compounds Preparation

Intermediate 1: 2-(2, 6-dioxopiperidin-3-yl)-5-fluoroisoindoline-1, 3-dione

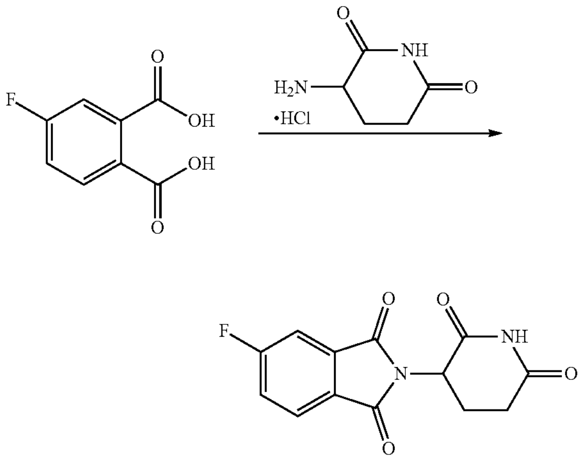

3-aminopiperidin-2, 6-dione hydrochloride (5.0 g, 0.03 mol) and potassium acetate (8.8 g, 0.09) were added to a solution of 4-fluorophthalic acid (5.52 g, 0.03 mol) in acetic acid (50 mL), and the reaction mixture was stirred at 120° C. for reaction overnight. The reaction mixture was concentrated under reduced pressure, the concentrate was diluted with water (100 mL), stirred at room temperature for 30 minutes, filtered, and the solid was washed with water (50 mL×2). The product (6.0 g) was obtained by drying under reduced pressure.

LC-MS: (ESI, m/z): $[M-H]^+=277.1$ $^1H$ NMR (400 MHz, DMSO) δ 11.14 (s, 1H), 8.01 (dd, J=8.2, 4.5 Hz, 1H), 7.85 (dd, J=7.4, 2.1 Hz, 1H), 7.79-7.66 (m, 1H), 5.17 (dd, J=12.8, 5.4 Hz, 1H), 2.90 (ddd, J=17.0, 13.8, 5.4 Hz, 1H), 2.58 (dd, J=24.5, 11.8 Hz, 2H), 2.20-2.01 (m, 1H).

Intermediate 2: N-(6-methoxy-2-(1-(2-(piperidin-4-yl) ethyl) piperidin-4-yl)-2H-indazol-5-yl)-6-(trifluoromethyl) pyridinecarboxamide

Step 1: Preparation of 2-fluoro-4-methoxy-5-nitrobenzaldehyde

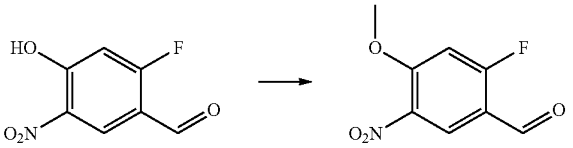

Cesium carbonate (3.5 g, 10.8 mmol) and potassium iodide (1.85 g, 13.0 mmol) were added to a solution of 2-fluoro-4-hydroxy-5-nitrobenzaldehyde (2 g, 10.8 mmol) in N,N-dimethylformamide (20 ml). The reaction solution was stirred for 10 hours at room temperature, water (30 ml) was added, extracted with ethyl acetate for three times, the organic phase was collected, washed with saturated saline, dried over anhydrous sodium sulfate, filtered, concentrated under reduced pressure, and the concentrate was purified by column to obtain 1.6 g of the target product 2-fluoro-4 methoxy-5-nitrobenzaldehyde.

LC-MS: (ES, m/z): $[M+H]^+=200.1$

Step 2: Preparation of 2-azido-4-methoxy-5-nitrobenzaldehyde

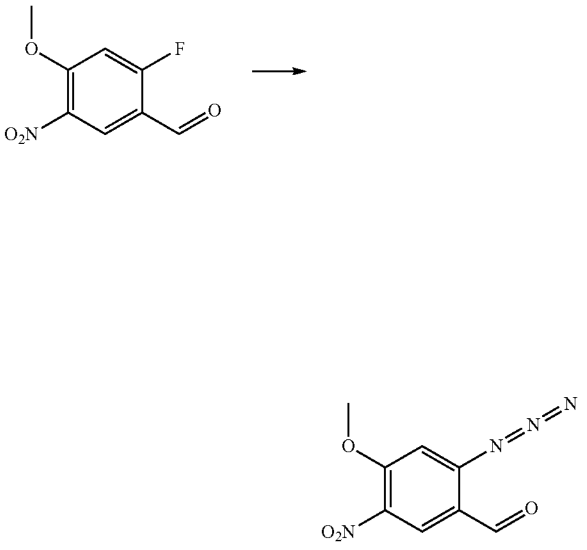

Sodium azide (1.06 g, 16.1 mmol) was added to a solution of 2-fluoro-4-methoxy-5-nitrobenzaldehyde (1.6 g, 8.04 mmol) in dimethyl sulfoxide (20 ml), stirred at room temperature for 2 hours, then the reaction solution was poured into ice water, extracted with ethyl acetate, and the organic phase was collected, washed with saturated saline, dried over anhydrous sodium sulfate, and concentrated to obtain 1.7 g of crude product, which was directly used in the next reaction without purification.

Step 3: Preparation of tert-butyl 4-(6-methoxy-5-nitro-2H-indazol-2-yl) piperidine-1-carboxylate

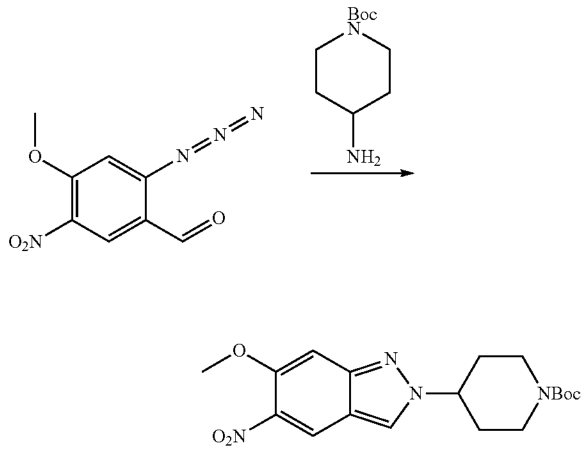

The solution of 2-azido-4-methoxy-5-nitrobenzaldehyde (1.7 g, 7.65 mmol) and tert-butyl 4-aminopiperidine-1-carboxylate (1.53 g, 7.65 mmol) in toluene (20 ml) was stirred and reacted at 100° C. for 2 hours, cooled to room temperature, the reaction solution was concentrated, 50 ml of water was added, extracted with ethyl acetate, organic phase was collected, washed with saturated saline, dried over anhydrous sodium sulfate, concentrated, and the concentrate was purified by column to obtain 1.72 g of tert-butyl 4-(6-methoxy-5-nitro-2H-indazol-2-yl) piperidine-1-carboxylate.

LC-MS: (ES, m/z): $[M+H]^+$=377.2

Step 4: Preparation of tert-butyl 4-(5-amino-6-methoxy-2H-indazol-2-yl) piperidine-1-carboxylate

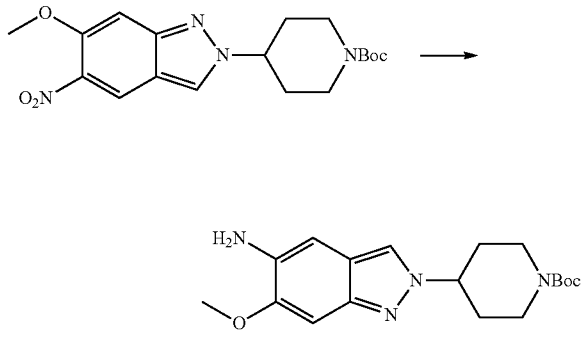

Iron powder (2.85 g, 50.9 mmol) and ammonium chloride (0.13 g, 2.3 mmol) were added to a solution of tert-butyl 4-(6-methoxy-5-nitro-2H-indazol-2-yl) piperidine-1-carboxylate (1.7 g, 4.5 mmol) in ethanol (20 ml), and the reaction solution was reacted at 90° C. for 2 hours. After the reaction solution was cooled to room temperature, it was filtered and concentrated to obtain 2.01 g of crude target product, which was directly used for the next reaction.

LC-MS: (ES, m/z): $[M+H]^+$=347.3

Step 5: Preparation of tert-butyl 4-(6-methoxy-5-(6-(trifluoromethyl) pyridine-2-amido)-2H-indazol-2-yl) piperidine-1-carboxylate

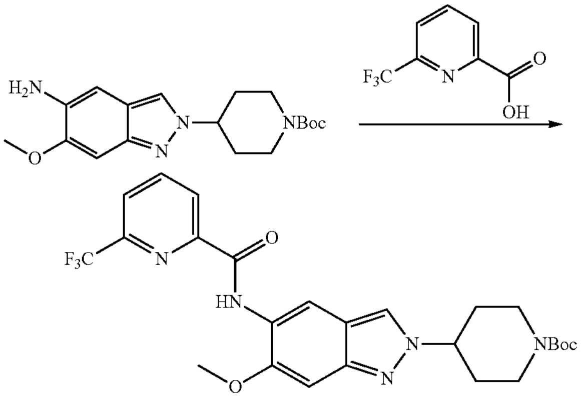

6-(trifluoromethyl) pyridine-2-carboxylic acid (940 mg, 4.9 mmol) and N,N-diisopropylethylamine (1.9 g, 14.7 mmol) were added to a solution of tert-butyl 4-(5-amino-6-methoxy-2H-indazol-2-yl) piperidine-1-carboxylate (1.7 g, 4.9 mmol) in tetrahydrofuran, then $T_3P$ (1.5 g) was added, and the reaction solution was stirred for 2 hours at room temperature. After concentrating the reaction solution, water was added, extracted with ethyl acetate for three times, and the organic phase was collected, washed with saturated saline, dried over anhydrous sodium sulfate and concentrated. The concentrate was purified by column to obtain 1.78 g of the target product tert-butyl 4-(6-methoxy-5-(6-(trifluoromethyl) pyridine-2-amido)-2H-indazol-2-yl) piperidine-1-carboxylate.

LC-MS: (ES, m/z): $[M+H]^+$=520.2

Step 6: Preparation of N-(6-methoxy-2-(piperidin-4-yl)-2H-indazol-5-yl)-6-(trifluoromethyl) pyridinecarboxamide

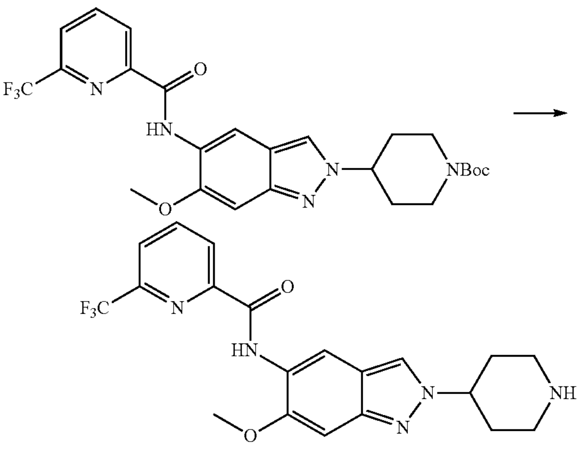

Trifluoroacetic acid (1 ml) was added to a solution of tert-butyl 4-(6-methoxy-5-(6-(trifluoromethyl) pyridine-2-amido)-2H-indazol-2-yl) piperidine-1-carboxylate (435 mg, 0.795 mmol) in dichloromethane. The reaction solution was stirred at room temperature for 1 h. The solvent was removed by concentration under reduced pressure to obtain the crude product (500 mg). The crude product was used directly for the next step.

LC-MS: (ES, m/z): $[M+H]^+$=420.2

Step 7: Preparation of tert-butyl 4-(2-(4-(6-methoxy-5-(6-(trifluoromethyl) pyridinecarboxamido)-2H-indazol-2-yl) piperidin-1-yl) ethyl) piperidine-1-formate

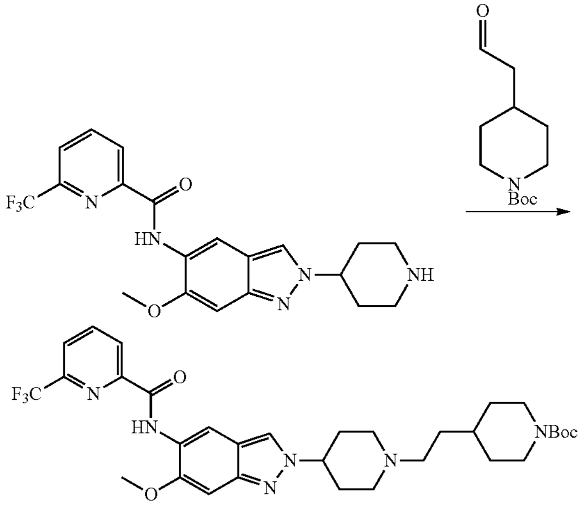

N-(6-methoxy-2-(piperidin-4-yl)-2H-indazol-5-yl)-6-(trifluoromethyl) pyridinecarboxamide (1.0 g, 2.386 mmol) and tert-butyl 4-(2-oxoethyl) piperidine-1-carboxylate (0.813 g, 3.581 mmol) in tetrahydrofuran (20 mL). The reaction solution was stirred for reaction overnight at room temperature. The reaction solution was diluted with ethyl acetate (50 mL), washed with water (2×50 mL) and saturated saline (50 mL), and the organic phase was collected, dried over anhydrous sodium sulfate, and concentrated under reduced pressure. The concentrate was purified by silica gel column to obtain 700 mg of target product as a yellow solid.

LC-MS: (ESI, m/z): $[M+H]^+$=631.3

Step 8: Preparation of N-(6-methoxy-2-(1-(2-(piperidin-4-yl) ethyl) piperidin-4-yl)-2H-indazol-5-yl)-6-(trifluoromethyl) pyridinecarboxamide

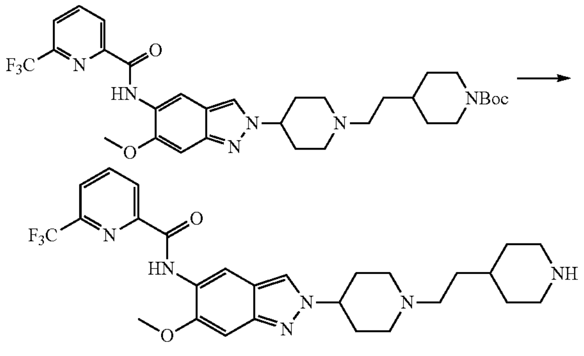

A mixture of tert-butyl 4-(2-(4-(6-methoxy-5-(6-(trifluoromethyl) pyridinecarboxamido)-2H-indazol-2-yl) piperidin-1-yl) ethyl) piperidine-1-formate (700 mg, 1.11 mmol) in hydrochloric acid/ethyl acetate (1M, 20 mL) was stirred and reacted overnight at room temperature. Reactants were concentrated under reduced pressure to obtain 650 mg of crude target product as a yellow oil. The crude product was used directly for the next step.

LC-MS: (ESI, m/z): $[M+H]^+$=531.3

Intermediate 3: N-(6-methoxy-2-(1-(piperidin-4-ylmethyl) piperidin-4-yl)-2H-indazol-5-yl)-6-(trifluoromethyl) pyridinecarboxamide

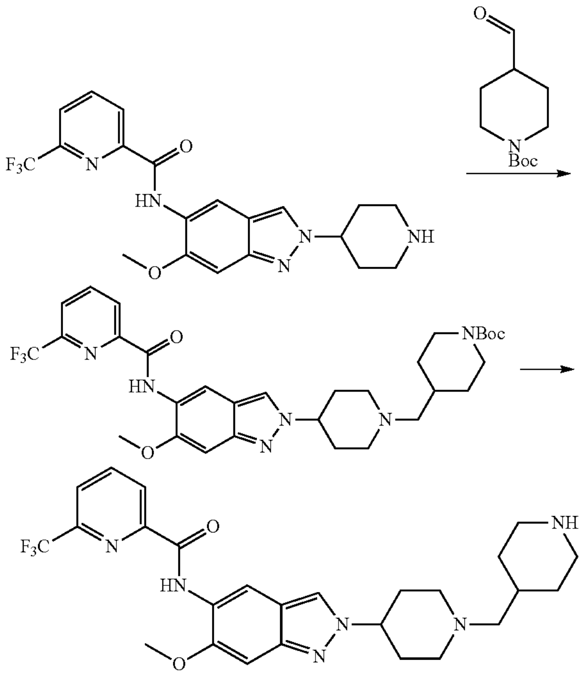

Intermediate 3 was synthesized with reference to the method of intermediate 2.

LC-MS: (ESI, m/z): $[M+H]^+$=517.2.

Intermediate 4: N-(6-methoxy-2-(1-(2-oxoethyl) piperidin-4-yl)-2H-indazol-5-yl)-6-(trifluoromethyl) pyridinecarboxamide Step 1: Preparation of N-(2-(1-(2, 2-dimethoxyethyl) piperidin-4-yl)-6-methoxy-2H-indazol-5-yl)-6-(trifluoromethyl) pyridinecarboxamide

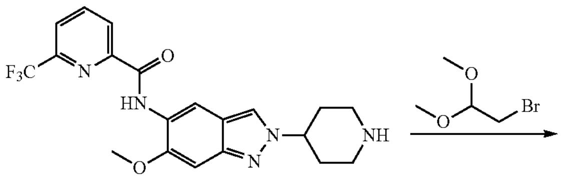

-continued

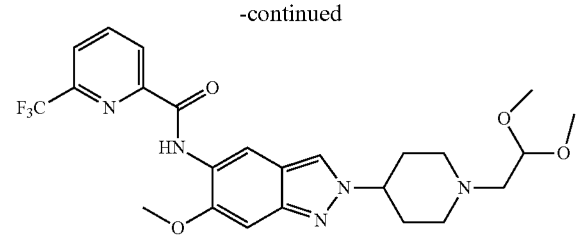

Potassium carbonate (1.235 g, 8.95 mmol) and potassium iodide (149 mg, 0.89 mmol) were added to a mixture of N-(6-methoxy-2-(piperidin-4-yl)-2H-indazol-5-yl)-6-(trifluoromethyl) pyridinecarboxamide (750 mg, 1.79 mmol) and 2-bromo-1,1-dimethoxyethane (46 mg, 0.3 mmol) in acetonitrile (20 mL). The reaction solution was stirred at 80° C. for reaction overnight. The reaction solution was concentrated under reduced pressure to remove the solvent, water (20 mL) was added, extracted with ethyl acetate (20 mL×3), and the organic layers were combined, washed with saturated saline (50 mL), dried over anhydrous sodium sulfate, filtered and concentrated under reduced pressure. The concentrate was purified by column to obtain 500 mg of target product as an oil.

LC-MS: (ESI, m/z): $[M+H]^+$=508.1

Step 2: Preparation of N-(6-methoxy-2-(1-(2-oxoethyl) piperidin-4-yl)-2H-indazol-5-yl)-6-(trifluoromethyl) pyridinecarboxamide

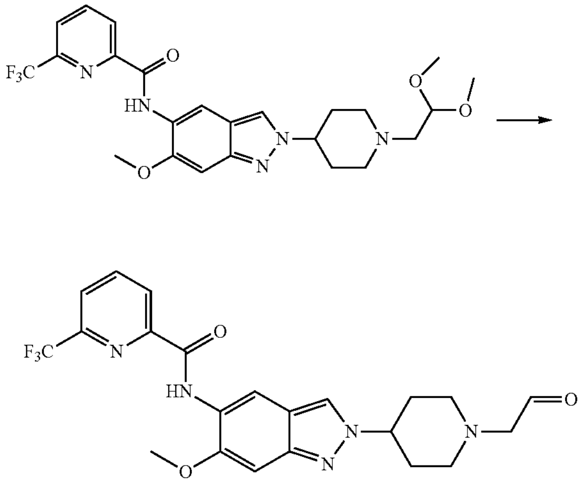

A mixture of N-(2-(1-(2, 2-dimethoxyethyl) piperidin-4-yl)-6-methoxy-2H-indazol-5-yl)-6-(trifluoromethyl) pyridinecarboxamide (500 mg, 0.99 mmol) in hydrochloric acid (4 mL)/dioxane (5 mL) was stirred overnight at 50° C. The reaction solution was concentrated under reduced pressure to remove the solvent, water (20 mL) was added, extracted with ethyl acetate (20 mL×3), and the organic layers were combined, washed with saturated saline (50 mL), dried over anhydrous sodium sulfate, filtered and concentrated under reduced pressure. The concentrate was purified by column to obtain 300 mg of target product as an oil.

LC-MS: (ESI, m/z): $[M+H]^+$=462.1

Intermediate 5: N-(6-(2-hydroxyprop-2-yl)-2-(piperidin-4-yl)-2H-indazol-5-yl)-6-(trifluoromethyl) pyridinecarboxamide Step 1: Preparation of methyl 5-nitro-1H-indazol-6-carboxylate

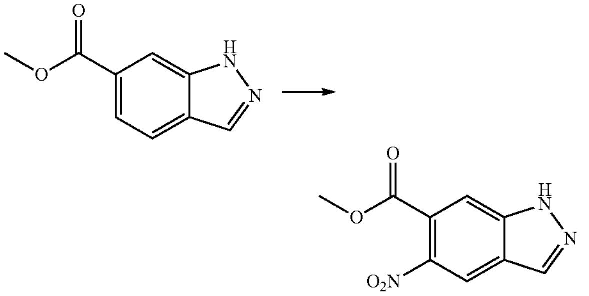

At −10° C., concentrated nitric acid (15 mL) was slowly added to a solution of methyl 1H-indazole-6-carboxylate (9.2 g. 0.052 mol) in concentrated sulfuric acid (20 mL). The reaction solution was stirred at −10° C. for 2 h. The reaction solution was poured into ice water, and the solid was filtered to obtain 10.8 g of the crude target product as a white solid. The crude product was used directly for the next step.

LC-MS: (ES, m/z): $[M+H]^+$=222.1

Step 2: Preparation of methyl 2-(1-(tert-butoxycarbonyl) piperidin-4-yl)-5-nitro-2H-indazole-6-carboxylate

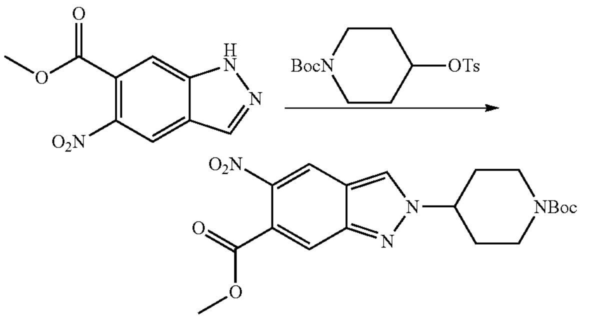

Potassium carbonate (11.1 g, 81.3 mmol) was added to a solution of methyl 5-nitro-1H-indazol-6-carboxylate (6 g, 27.12 mmol) and tert-butyl 4-(p-toluenesuloyloxy) piperidine-1-carboxylate (15.3 g, 43.5 mmol) in N,N-dimethylformamide (100 mL). The reaction solution was stirred at 100° C. for 10 h. The reaction solution was cooled to room temperature, water (50 ml) and ethyl acetate (100 ml) were added, and the water layer was separated and extracted with ethyl acetate (100 ml×2). The organic layers were combined, washed with saline (100 mL×2), dried over anhydrous sodium sulfate, filtered and concentrated under reduced pressure. The concentrate was purified by silica gel column to obtain 2.01 g of target product as a yellow solid.

LC-MS: (ES, m/z): $[M+H]^+$=405.2

Step 3: Preparation of methyl 5-amino-2-(1-(tert-butoxycarbonyl) piperidin-4-yl)-2H-indazole-6-carboxylate

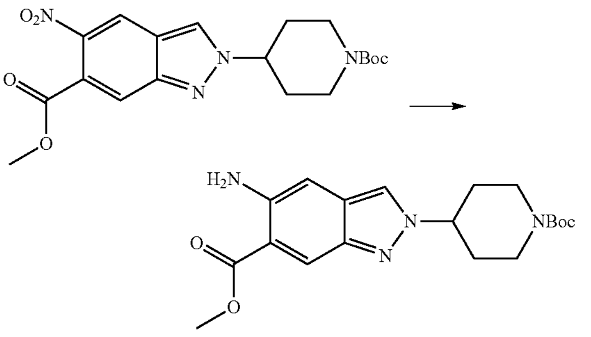

Iron powder (2.85 g, 50.9 mmol) and ammonium chloride (0.13 g, 2.3 mmol) were added to a solution of methyl 2-(1-(tert-butoxycarbonyl) piperidin-4-yl)-5-nitro-2H-indazol-6-carboxylate (1.7 g, 4.5 mmol) in ethanol (20 ml). The reaction solution was stirred at 90° C. for 2 h. The reaction solution was cooled to room temperature, filtered, and the filtrate was concentrated under reduced pressure to obtain 2.01 g of the crude target product as an oil. The crude product was used directly for the next step.

LC-MS: (ES, m/z): $[M+H]^+$=375.3

Step 4: methyl 2-(1-(tert-butoxycarbonyl) piperidin-4-yl)-5-(6-(trifluoromethyl) pyridinecarboxamido)-2H-indazole-6-carboxylate

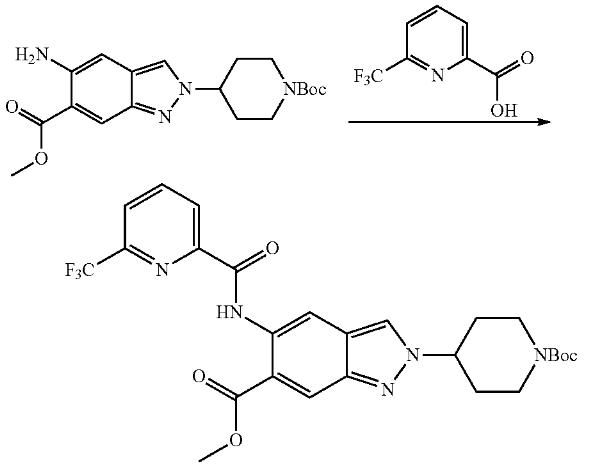

$T_3P$ (650 mg) was added to a mixture of methyl 5-amino-2-(1-(tert-butoxycarbonyl) piperidin-4-yl)-2H-indazol-6-carboxylate (170 mg, 0.45 mmol), 6-(trifluoromethyl) pyridine-2-carboxylic acid (86.8 mg, 0.45 mmol) and DIEA (88 mg, 0.68 mmol) in THF. The reaction solution was stirred at room temperature for 2 hours. The solvent was removed by concentration under reduced pressure. Water (20 mL) and ethyl acetate (20 mL) were added. The water layer was separated and extracted with ethyl acetate (20 ml×2). The organic layers were combined, washed with saline (20 mL×2), dried over anhydrous sodium sulfate, filtered and concentrated under reduced pressure. The concentrate was purified by silica gel column to obtain 150 mg of target product as a yellow solid.

LC-MS: (ES, m/z): $[M+H]^+$=548.3

Step 5: Preparation of tert-butyl 4-(6-(2-hydroxyprop-2-yl)-5-(6-(trifluoromethyl) pyridinecarboxamid)-2H-indazol-2-yl) piperidine-1-carboxylate

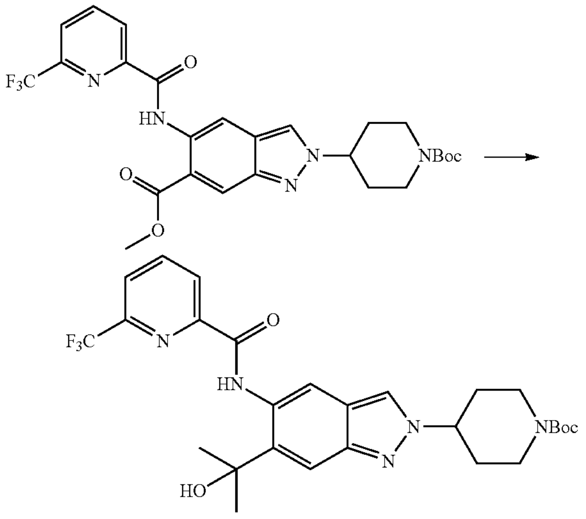

Lithium chloride (192 mg, 4.57 mmol) was added to a solution of methyl 2-(1-(tert-butoxycarbonyl) piperidin-4-yl)-5-(6-(trifluoromethyl) pyridinecarboxamido)-2H-indazole-6-carboxylate (500 mg, 0.91 mmol) in tetrahydrofuran. The reaction solution was cooled to 0° C., and then tetrahydrofuran methylmagnesium bromide (3.04 ml, 1M) was added. The reaction solution was stirred at room temperature for 12 h, quenched with ammonium chloride aqueous solution, and water (30 mL) and ethyl acetate (50 mL) were added. The water layers were separated and extracted with ethyl acetate (50 ml×2), the organic layers were combined, washed with saline (50 ml×2), dried over anhydrous sodium sulfate, filtered and concentrated under reduced pressure, and the concentrate was purified by silica gel column to obtain 435 mg of target product as a white solid.

LC-MS: (ES, m/z): $[M+H]^+$=548.3

Step 6: Preparation of N-(6-(2-hydroxyprop-2-yl)-2-(piperidin-4-yl)-2H-indazol-5-yl)-6-(trifluoromethyl) pyridinecarboxamide

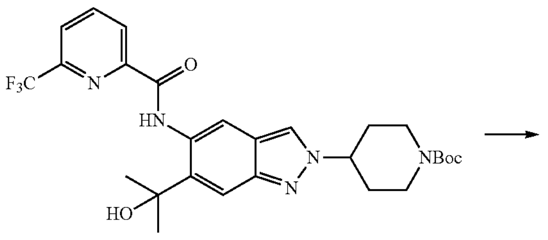

-continued

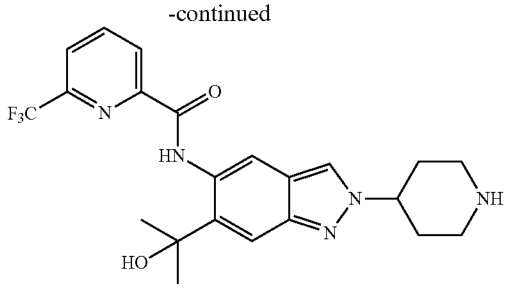

A mixture of tert-butyl 4-(6-(2-hydroxyprop-2-yl)-5-(6-(trifluoromethyl) pyridineformamido)-2H-indazol-2-yl) piperidine-1-carboxylate (435 mg, 0.79) in dichloromethane (3 mL) and trifluoroacetic acid (1 mL) was stirred and reacted at room temperature for 1 h. The solvent was removed by concentration under reduced pressure, and 500 mg of crude target product was obtained as a yellow oil. The crude product was used directly for the next step.

LC-MS: (ES, m/z): $[M+H]^+$=448.2

Intermediate 6:2-(4-(2-(2, 6-dioxopiperidin-3-yl)-1, 3-dioxoisoindolin-5-yl) piperazin-1-yl) acetaldehyde Step 1: Preparation of tert-butyl 4-(2, 2-dimethoxyethyl) piperazine-1-carboxylate

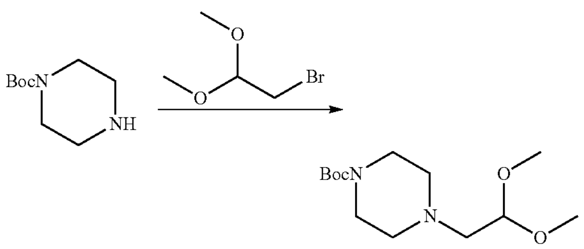

2-Bromo-1, 1-dimethoxyethane (3.63 g, 21.51 mmol) was added to a mixture of tert-butyl piperazine-1-carboxylate (2.0 g, 10.75 mmol), potassium carbonate (4.45 g, 32.26 mmol) and potassium iodide (892 mg, 5.38 mmol) in acetone (20 mL). The reaction was stirred at 80° C. overnight. The reaction mixture was concentrated under reduced pressure. The concentrate was dissolved in ethyl acetate (50 mL) and washed with water (50 mL*2) and saturated saline (50 mL). The organic phase was collected, dried over anhydrous sodium sulfate, filtered and concentrated. The concentrate was purified by silica gel column to obtain the desired product (2.2 g).

LC-MS: (ES, m/z): $[M+H]^+$=275.0.

Step 2: Preparation of 1-(2, 2-dimethoxyethyl) piperazine

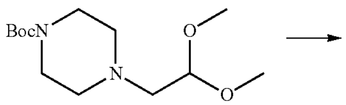

-continued

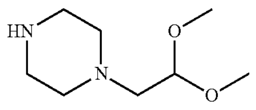

A mixture of tert-butyl 4-(2, 2-dimethoxyethyl) piperazine-1-carboxylate (2.2 g, 8.03 mmol) in hydrochloric acid/dioxane (4M, 10 mL) was stirred overnight at room temperature. The reaction mixture was concentrated under reduced pressure to obtain light yellow oily product (1.5 g, crude). The crude product was used directly for the next step.

Step 3: Preparation of 5-(4-(2, 2-dimethoxyethyl) piperazin-1-yl)-2-(2, 6-dioxo piperidin-3-yl) isoindoline-1, 3-dione

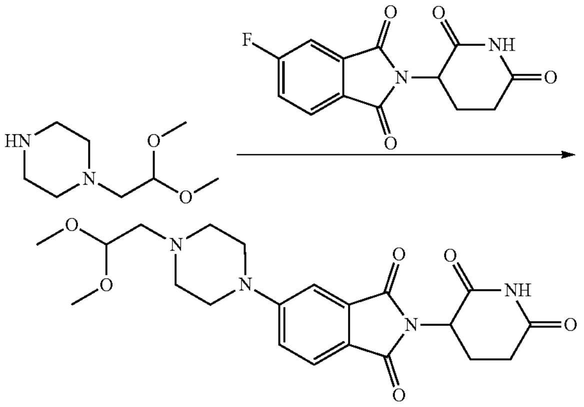

A mixture of 2-(2, 6-dioxopiperidin-3-yl)-5-fluoroisoindoline-1, 3-dione (1.48 g, 5.36 mmol), 1-(2, 2-dimethoxyethyl) piperazine (1.4 g, 8.05 mmol) and DIEA (4.15 g, 36.16 mmol) in NMP (10 mL) was reacted at 140° C. for 5 h in a microwave reactor. The mixture was diluted with water (50 mL) and extracted with ethyl acetate (50 mL*2). The organic phase was collected and washed with water (100 mL*2) and saturated saline (50 mL), dried over anhydrous sodium sulfate, filtered and concentrated. The concentrate was purified by silica gel column to obtain the desired product (1.8 g).

LC-MS: (ESI, m/z): $[M+H]^+$=431.1.

Step 4: Preparation of 2-(4-(2-(2,6-dioxopiperidin-3-yl)-1, 3-dioxoisoindolin-5-yl) piperazin-1-yl) acetaldehyde

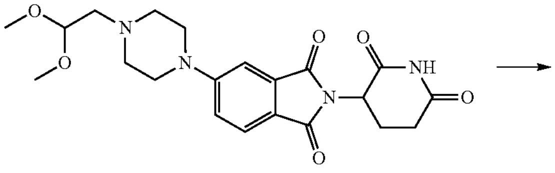

-continued

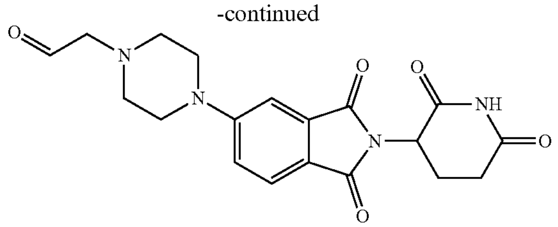

A mixture of 5-(4-(2, 2-dimethoxyethyl) piperazin-1-yl)-2-(2, 6-dioxo piperidin-3-yl) isoindoline-1, 3-dione (1.8 g, 4.19 mmol) in trifluoroacetic acid/dichloromethane (5 mL/5 mL) was stirred for 60 h at room temperature. The mixture was concentrated under reduced pressure, water was added, and the pH was adjusted to 8 with sodium bicarbonate (aqueous solution). The mixture was extracted with ethyl acetate (100 mL*2). The organic phase was collected and washed with water (100 mL*2) and saturated saline (100 mL), dried over anhydrous sodium sulfate, filtered and concentrated. The concentrate was purified by silica gel column to obtain the desired product (700 mg).

LC-MS: (ESI, m/z): $[M+H]^+$=285.0.

Intermediate 7:2-(4-(2-(2, 6-dioxopiperidin-3-yl)-1, 3-dioxoisoindolin-5-yl) piperazin-1-yl)-2-methylpropanal

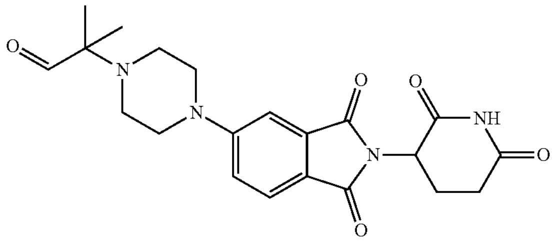 [SMILES: CC(C)(C=O)N1CCN(c2ccc3c(c2)C(=O)N(C2CCC(=O)NC2=O)C3=O)CC1]

Synthesized with reference to the method of intermediate 6.

LC-MS: (ESI, m/z): $[M+H]^+$=413.2.

Intermediate 8:2-(1-(2-(2,6-dioxopiperidin-3-yl)-1, 3-dioxoisoindolin-5-yl) piperidin-4-yl) acetaldehyde Step 1: Preparation of 2-(2,6-dioxopiperidin-3-yl)-5-(4-(2-hydroxyethyl) piperidin-1-yl) isoindoline-1, 3-dione

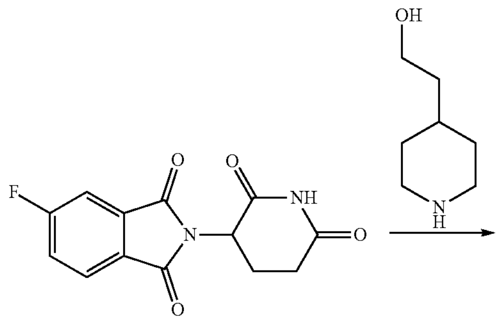

-continued

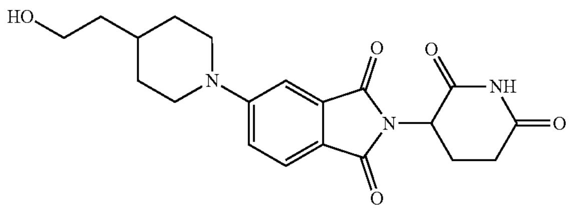

A mixture of 2-(2, 6-dioxopiperidin-3-yl)-5-fluoroisoindoline-1, 3-dione (500 mg, 1.81 mmol), 2-(piperidin-4-yl) ethan-1-ol (280, 2.17 mmol) and DIEA (701 mg, 5.43 mmol) in NMP (5 mL) was reacted in a microwave reactor at 140° C. for 5 hours. The reaction mixture was diluted with water (50 mL) and extracted with ethyl acetate (50 mL*2). The organic phase was collected and washed with water (100 mL*2) and saturated saline (50 mL), dried over anhydrous sodium sulfate, filtered and concentrated. The concentrate was purified by silica gel column to obtain the product (650 mg).

LC-MS: (ES, m/z): $[M+H]^+$=386.1.

Step 2: Preparation of 2-(1-(2-(2, 6-dioxopiperidin-3-yl)-1, 3-dioxoisoindolin-5-yl) piperidin-4-yl) acetaldehyde

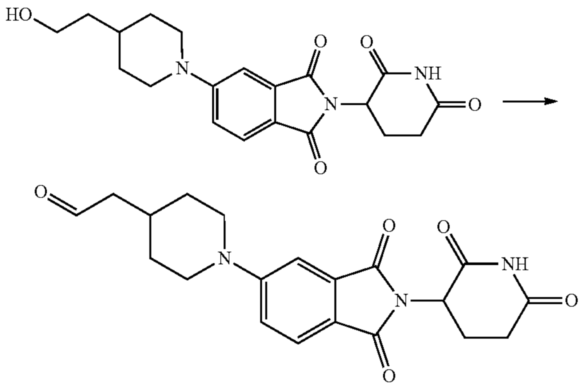

A mixture of 2-(2, 6-dioxopiperidin-3-yl)-5-(4-(2-hydroxyethyl) piperidin-1-yl) isoindoline-1, 3-dione (300 mg, 0.78 mmol) and IBX (436 mg, 1.56 mmol) in acetonitrile (6 mL) was stirred for 2 h at 80° C. The reaction mixture was diluted with water (30 mL) and extracted with ethyl acetate (30 mL*2). The organic phase was collected and washed with water (50 mL×2) and saturated saline (30 mL), dried over anhydrous sodium sulfate, filtered and concentrated. The concentrate was purified by silica gel column to obtain the product (22 mg).

LC-MS: (ES, m/z): $[M+H]^+$=384.1.

1H NMR (400 MHz, DMSO-$d_6$) δ 11.07 (s, 1H), 9.69 (t, J=1.6 Hz, 1H), 7.65 (d, J=8.6 Hz, 1H), 7.31 (d, J=2.0 Hz, 1H), 7.23 (dd, J=8.6, 2.2 Hz, 1H), 5.06 (dd, J=12.9, 5.4 Hz, 1H), 4.03 (dd, J=10.3, 2.9 Hz, 2H), 3.04-2.82 (m, 3H), 2.65-2.52 (m, 2H), 2.41 (dd, J=6.7, 1.6 Hz, 2H), 2.17-1.97 (m, 2H), 1.73 (d, J=11.1 Hz, 2H), 1.2-1.18 (m, 2H).

Intermediate 9: 3-(1-(2-(2, 6-dioxopiperidin-3-yl)-1, 3-dioxoisoindolin-5-yl) piperidin-4-yl) propanal

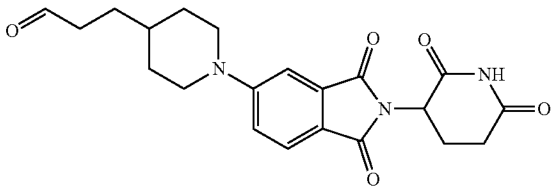 [SMILES: O=CCCC1CCN(c2ccc3c(c2)C(=O)N(C2CCC(=O)NC2=O)C3=O)CC1]

Synthesized with reference to the method of intermediate 8.

LC-MS: (ES, m/z): $[M+H]^+$=398.2.

Intermediate 10:1-(2-(2, 6-dioxopiperidin-3-yl)-1, 3-dioxoisoindolin-5-yl) piperidine-4-formaldehyde

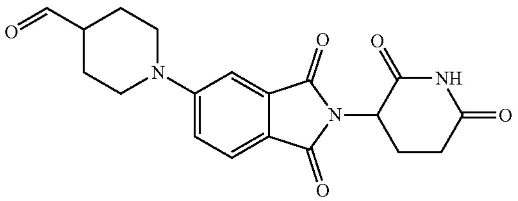 [SMILES: O=CC1CCN(c2ccc3c(c2)C(=O)N(C2CCC(=O)NC2=O)C3=O)CC1]

Synthesized with reference to the method of intermediate 8.

LC-MS: (ES, m/z): $[M+H]^+$=370.1.

Intermediate 11:2-(1-(2-(2, 6-dioxopiperidin-3-yl)-1, 3-dioxoisoindolin-5-yl) piperidin-4-yl)-2-methylpropanal

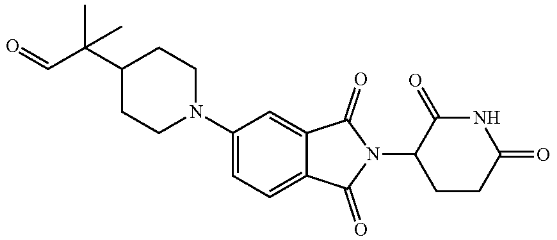

Synthesized with reference to the method of intermediate 8.

LC-MS: (ES, m/z): $[M+H]^+$=412.2.

Intermediate 12:2-(2, 6-dioxopiperidin-3-yl)-5-(piperazin-1-yl) isoindoline-1, 3-dione Step 1: Preparation of tert-butyl 4-(2-(2, 6-dioxopiperidin-3-yl)-1, 3-dioxoisoindolin-5-yl) piperazine-1-carboxylate

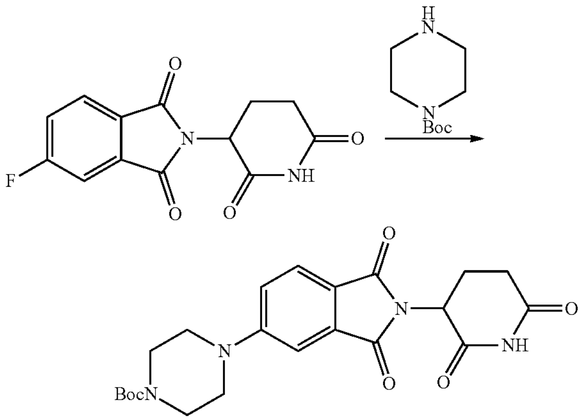

A mixture of 2-(2, 6-dioxopiperidin-3-yl)-5-fluoroisoindoline-1, 3-dione (300 mg, 1.09 mmol), tert-butyl piperazine-1-carboxylate (203 mg, 1.09 mmol) and DIEA (422 mg, 3.27 mmol) in NMP (1 mL) was reacted at 140° C. for 5 h in a microwave reactor. The mixture was cooled to room temperature, diluted with water (20 mL) and extracted with dichloromethane (10 mL×3). The organic phase was combined, concentrated under reduced pressure, and the concentrate was purified by silica gel column to obtain the product (90 mg).

LC-MS: (ESI, m/z): $[M+H]^+$=788.2.

Step 2: Preparation of 2-(2,6-dioxopiperidin-3-yl)-5-(piperazin-1-yl) isoindoline-1, 3-dione

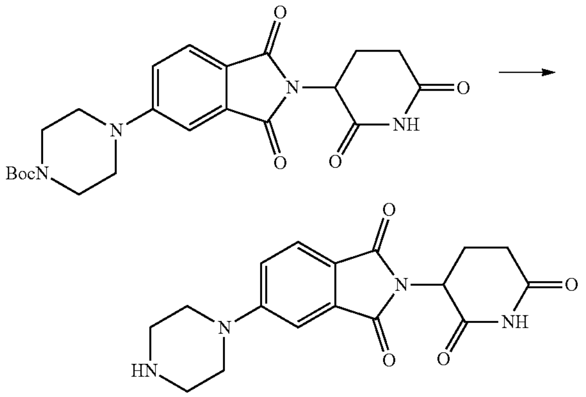

Trifluoroacetic acid (1 mL) was added to tert-butyl 4-(2-(2, 6-dioxopiperidin-3-yl)-1, 3-dioxoisoindolin-5-yl) piperazine-1-carboxylate (65 mg, 0.147 mmol) in dichloromethane (5 mL), and the mixture was stirred at room temperature for 2 h. The mixture was concentrated under reduced pressure, the concentrate was diluted with saturated sodium bicarbonate aqueous solution (5 mL) and extracted with dichloromethane (5 mL×3). The organic phase was combined and concentrated under reduced pressure to obtain the crude product (59 mg). The crude product can be used directly for the next step without further purification.

LC-MS: (ESI, m/z): $[M+H]^+$=343.3.

Intermediate 13: 3-(1-(2-(2, 6-dioxopiperidin-3-yl)-1, 3-dioxoisoindolin-5-yl) piperidin-4-yl)-3-methyl-butyraldehyde

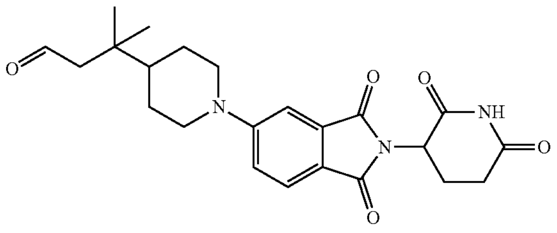

Synthesized with reference to the method of intermediate 8.

LC-MS: (ES, m/z): $[M+H]^+$=426.2.

Intermediate 14:3-(4-(2-(2, 6-dioxopiperidin-3-yl)-1, 3-dioxoisoindolin-5-yl) piperazin-1-yl)-3-methylbu-tyraldehyde

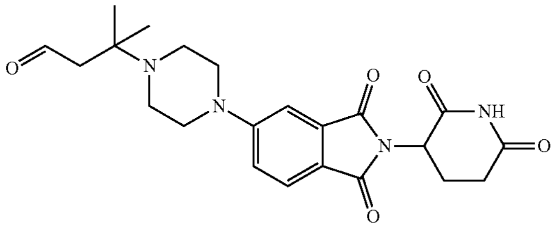 [SMILES: CC(C)(CC=O)C1CCN(c2ccc3c(c2)C(=O)N(C2CCC(=O)NC2=O)C3=O)CC1]

Synthesized with reference to the method of intermediate 6.

LC-MS: (ESI, m/z): $[M+H]^+$=427.2.

Intermediate 15:2-(9-(2-(2, 6-dioxopiperidin-3-yl)-1, 3-dioxoisoindolin-5-yl)-3, 9-diazaspiro[5.5]undec-3-yl) acetaldehyde

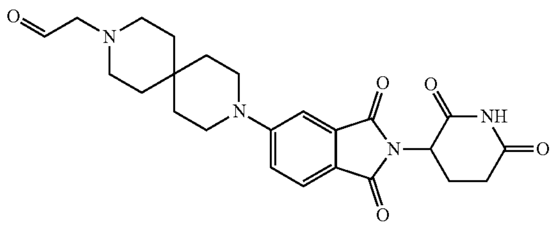 [SMILES: O=CCN1CCC2(CC1)CCN(c1ccc3c(c1)C(=O)N(C1CCC(=O)NC1=O)C3=O)CC2]

Synthesized with reference to the method of intermediate 6.

LC-MS: (ESI, m/z): $[M+H]^+$=453.2.

Intermediate 16:2-(9-(2-(2, 6-dioxopiperidin-3-yl)-1, 3-dioxoisoindolin-5-yl)-3, 9-diazaspiro [5.5]undec-3-yl)-2-methylpropanal

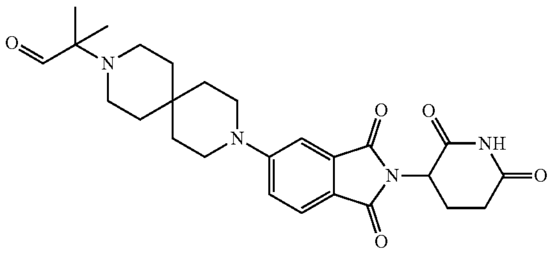 [SMILES: CC(C)(C=O)C1CCC2(CC1)CCN(c1ccc3c(c1)C(=O)N(C1CCC(=O)NC1=O)C3=O)CC2]

Synthesized with reference to the method of intermediate 6.

LC-MS: (ESI, m/z): $[M+H]^+$=481.2.

Intermediate 17:2-(3-(2-(2, 6-dioxopiperidin-3-yl)-1, 3-dioxoisoindolin-5-yl)-3-azaspiro[5.5]undec-9-yl)-2-methyl propanal

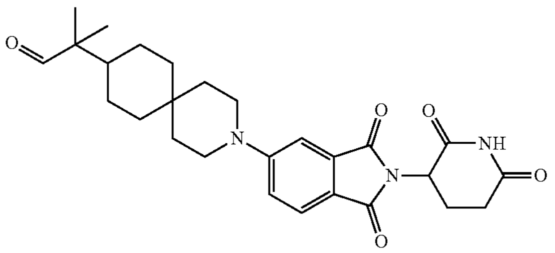

Synthesized with reference to the method of intermediate 8.

LC-MS: (ESI, m/z): $[M+H]^+$=480.2.

Intermediate 18:2-(3-(2-(2, 6-dioxopiperidin-3-yl)-1, 3-dioxoisoindolin-5-yl)-3-azaspiro[5.5] undec-9-yl) acetaldehyde

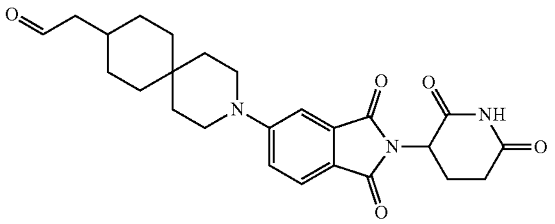 [SMILES: O=CCC1CCC2(CC1)CCN(c1ccc3c(c1)C(=O)N(C1CCC(=O)NC1=O)C3=O)CC2]

Synthesized with reference to the method of intermediate 8.

LC-MS: (ESI, m/z): $[M+H]^+$=452.2.

Intermediate 19:3-(2-(2, 6-dioxopiperidin-3-yl)-1, 3-dioxoisoindolin-5-yl)-3-azaspiro[5.5]undecane-9-formaldehyde

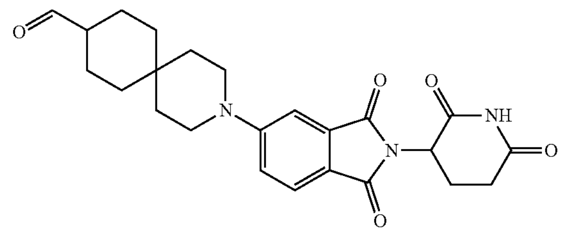 [SMILES: O=CC1CCC2(CC1)CCN(c1ccc3c(c1)C(=O)N(C1CCC(=O)NC1=O)C3=O)CC2]

Synthesized with reference to the method of intermediate 8.

LC-MS: (ESI, m/z): $[M+H]^+$=438.2.

Intermediate 20:2-(2-((2-(2, 6-dioxopiperidin-3-yl)-1, 3-dioxoisoindolin-5-yl) oxy) ethoxy) acetaldehyde Step 1: Preparation of 2-(2, 6-dioxopiperidin-3-yl)-5-(2-(2-hydroxyethoxy) ethoxy) isoindoline-1, 3-dione

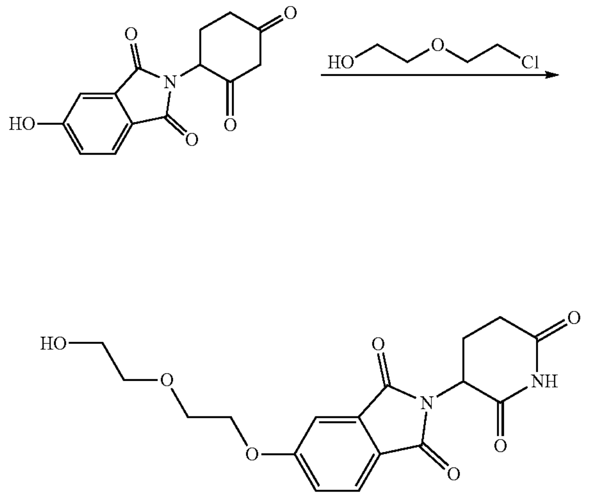

DIEA (706.2 mg, 0.0055 mol) and potassium iodide (30 mg, 0.0002 mol) were added dropwise to a mixture of 2-(2,6-dioxopiperidin-3-yl)-5-hydroxyisoindoline-1,3-dione (500 mg, 0.0018 mol) and 2-(2-chloroethoxy)ethan-1-ol (227 mg, 0.0018 mol) in dimethylsulfoxide (20 mL). The reaction solution was stirred at 100° C. for 10 h. Water (30 ml) and ethyl acetate (100 ml) were added, and the water layer was separated, and extracted with ethyl acetate (100 ml×2). The organic phases were combined and washed with saline (100 mL×2), dried over anhydrous sodium sulfate, filtered and concentrated under reduced pressure. The concentrate was purified by silica gel column to obtain 612 mg of target product as a white solid.

LC-MS: (ES, m/z): $[M+H]^+$=363.0

Step 2: Preparation of 2-(2-((2-(2, 6-dioxopiperidin-3-yl)-1, 3-dioxoisoindolin-5-yl) oxy) ethoxy) acetaldehyde

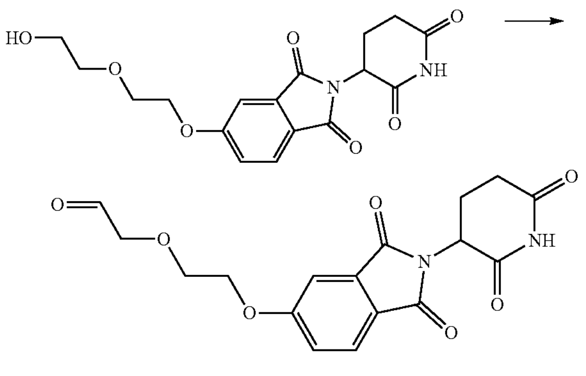

Dess-Martin (393 mg, 0.88 mmol) was added to a mixture of 2-(2, 6-dioxopiperidin-3-yl)-5-(2-(2-hydroxyethoxy) ethoxy) isoindoline-1, 3-dione (162 mg, 0.44 mmol) in THF (10 mL) at 0° C., and the obtained reaction solution was stirred for 16 hours at room temperature. The reaction solution was quenched with water (30 ml) and dichloromethane (50 ml). The water layer was separated and extracted with dichloromethane (50 ml×2). The organic phases were combined, washed with saturated saline (50 mL×2), dried over anhydrous sodium sulfate, filtered and concentrated under reduced pressure. The concentrate was purified by silica gel column to obtain 32 mg of target product as a white solid.

LC-MS: (ES, m/z): $[M+H]^+$=361.0

Intermediate 21: tert-butyl 9-(2-hydroxyethyl)-3-azaspiro[5.5] undecane-3-carboxylate Step 1: tert-butyl 9-(2-ethoxy-2-oxoethylidene)-3-azaspiro[5.5] undecane-3-carboxylate

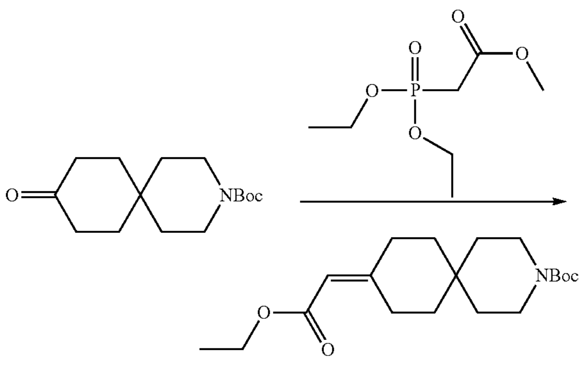

At 0° C., sodium hydride (60% mineral oil mixture, 224 mg, 5.6 mmol) was added to a solution of ethyl 2-(diethoxyphosphoryl) acetate (1.26 g, 5.63 mmol) in N,N-dimethylformamide (15 mL), and stirred at 0° C. for 0.5 h, then tert-butyl 9-oxo-3-azaspiro [5.5]undecane-3-carboxylate (1.0 g, 3.75 mmol) was added. The reaction mixture was stirred at 0° C. for 3 h. The reaction mixture was diluted with water (100 mL) and extracted with ethyl acetate (3×30 mL).

The organic layer was collected and washed with water (2×20 mL) and saturated saline (20 mL), dried over anhydrous sodium sulfate, filtered and concentrated. 0.7 g of the target crude product was obtained. The crude product was used directly for the next step.

Step 2: tert-butyl 9-(2-ethoxy-2-oxoethyl)-3-azaspiro[5.5] undecane-3-carboxylate

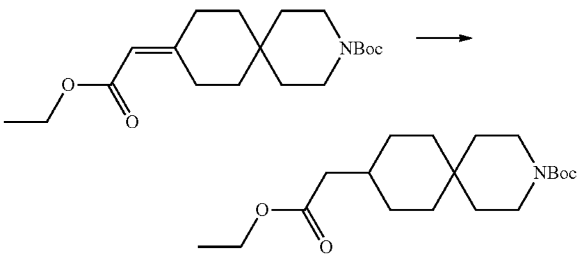

The reaction mixture of tert-butyl 9-(2-ethoxy-2-oxoethylidene)-3-azaspiro[5.5]undecane-3-carboxylate (0.7 g, 2.08 mmol) and palladium hydroxide (0.2 g, 1.43 mmol) in ethanol (10 mL) was stirred at room temperature for 16 h under hydrogen atmosphere. The reaction mixture was filtered and concentrated under reduced pressure to obtain 0.5 g of the crude target product. The crude product was used directly for the next step.

$^1$H NMR (400 MHz, $CDCl_3$) δ 4.12 (q, J=7.1 Hz, 2H), 3.35 (ddd, J=7.6, 6.8, 5.0 Hz, 4H), 2.20 (d, J=7.1 Hz, 2H), 1.70-1.63 (m, 2H), 1.58 (dd, J=12.7, 7.1 Hz, 2H), 1.45 (s, 9H), 1.27 (dt, J=14.3, 6.5 Hz, 6H), 1.18-1.10 (m, 4H), 0.86 (dd, J=13.4, 6.3 Hz, 2H).

Step 3: tert-butyl 9-(2-hydroxyethyl)-3-azaspiro[5.5] undecane-3-carboxylate

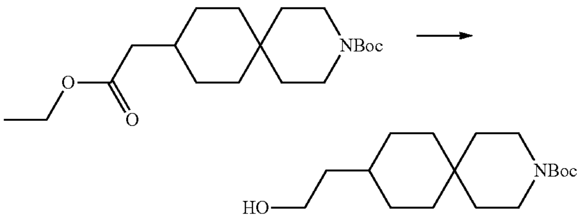

The reaction mixture of tert-butyl 9-(2-ethoxy-2-oxoethyl)-3-azaspiro[5.5]undecane-3-carboxylate (0.5 g, 1.47 mmol) and lithium borohydride (0.13 g, 5.9 mmol) in tetrahydrofuran (5 mL) was refluxed overnight. The reaction mixture was diluted with water (50 mL) and extracted with ethyl acetate (3×30 mL). The organic layer was collected and washed with water (2×20 mL) and saturated saline (20 mL), dried over anhydrous sodium sulfate, filtered and concentrated to obtain 0.4 g of the crude target product.

LC-MS: (ESI, m/z): $[M+H]^+$=298.2

$^1$H NMR (400 MHz, MeOD) δ 3.58 (t, J=6.6 Hz, 2H), 3.43-3.28 (m, 5H), 1.77-1.66 (m, 2H), 1.62-1.52 (m, 2H), 1.52-1.41 (m, 13H), 1.29 (t, J=5.6 Hz, 3H), 1.12 (dd, J=19.2, 11.5 Hz, 4H).

Example 1: N-(2-(1-(2-(1-(2-(2, 6-dioxopiperidin-3-yl)-1, 3-dioxoisoindolin-5-yl) piperidin-4-yl) ethyl) piperidin-4-yl)-6-methoxy-2H-indazol-5-yl)-6-(trifluoromethyl) pyridinecarboxamide

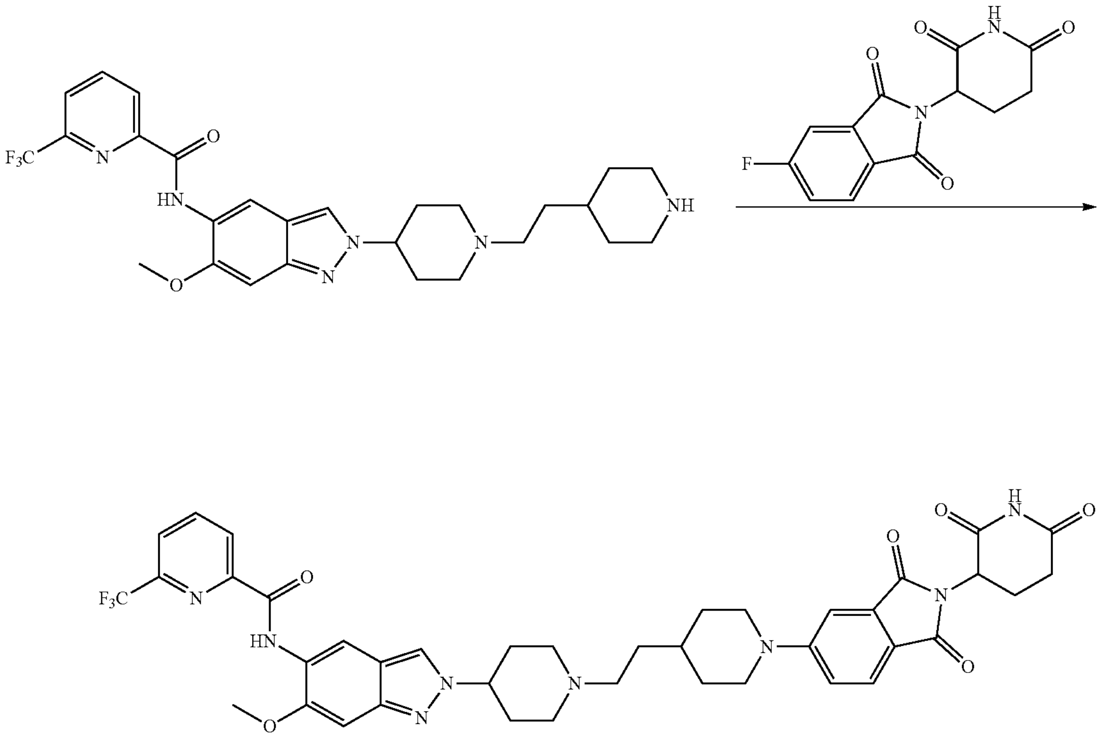

A mixture of N-(6-methoxy-2-(1-(2-(piperidin-4-yl) ethyl) piperidin-4-yl)-2H-indazol-5-yl)-6-(trifluoromethyl) pyridinecarboxamide (200 mg, 0.377 mmol), 2-(2, 6-dioxopiperidin-3-yl)-5-fluoroisoindoline-1, 3-dione (104 mg, 0.377 mmol) and DIEA (243 mg, 1.887 mmol) in NMP (100 mL) was reacted at 140° C. for 5 h in a microwave reactor. The resulting mixture was diluted with ethyl acetate and washed with water and brine. The organic phase was collected, dried over anhydrous sodium sulfate, concentrated under reduced pressure, and the concentrate was purified by preparative HPLC to obtain the desired product (14.52 mg).

LC-MS: (ESI, m/z): $[M+H]^+$=787.2.

1H NMR (400 MHz, DMSO-$d_6$) δ 11.07 (s, 1H), 10.50 (s, 1H), 8.69 (s, 1H), 8.54-8.31 (m, 3H), 8.22 (d, J=7.7 Hz, 1H), 7.65 (d, J=8.6 Hz, 1H), 7.31 (s, 1H), 7.24 (m, J=8.7, 2.1 Hz, 1H), 7.16 (s, 1H), 5.06 (m, 1H), 4.41-4.38 (m, 1H), 4.05 (d, J=13.2 Hz, 2H), 3.98 (s, 3H), 3.04-2.85 (m, 5H), 2.71-2.53 (m, 2H), 2.42-2.36 (m, 2H), 2.11-2.05 (m, 6H), 2.03-1.95 (m, 1H), 1.79 (d, J=11.5 Hz, 2H), 1.65-1.61 (m, 1H), 1.48-1.39 (m, 2H), 1.25-1.20 (m, 2H).

Example 2: N-(2-(1-((1-(2-(2, 6-dioxopiperidin-3-yl)-1, 3-dioxoisoindolin-5-yl) piperidin-4-yl) methyl) piperidin-4-yl)-6-methoxy-2H-indazol-5-yl)-6-(trifluoromethyl) pyridinecarboxamide

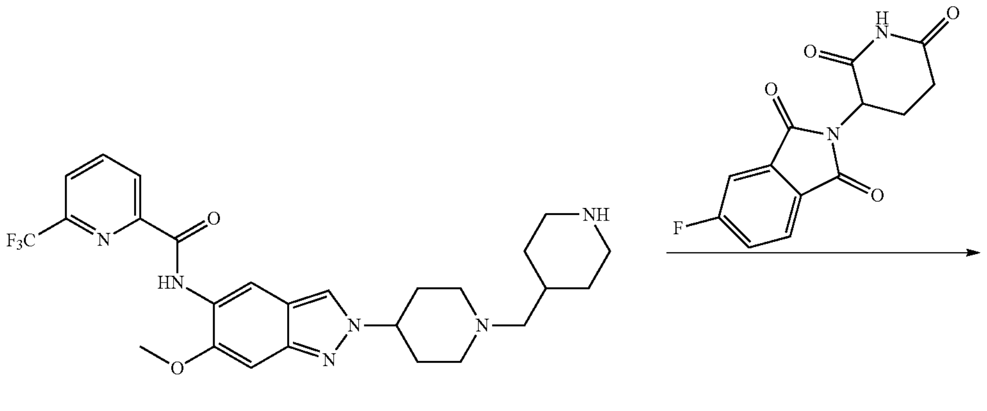

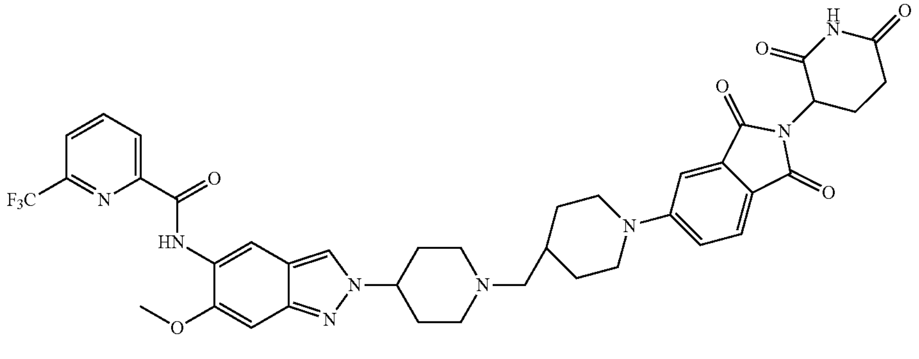

The target compound (27 mg) was obtained by referring to the preparation method of Example 1.

LC-MS: (ESI, m/z): $[M+H]^+$=773.4.

$^1$H NMR (400 MHz, DMSO-$d_6$) δ 11.08 (s, 1H), 10.51 (s, 1H), 8.69 (s, 1H), 8.49-8.36 (m, 3H), 8.33 (s, 0.3H), 8.25-8.17 (m, 1H), 7.66 (d, J=8.6 Hz, 1H), 7.32 (d, J=1.9 Hz, 1H), 7.24 (dd, J=8.7, 2.1 Hz, 1H), 7.17 (s, 1H), 5.07 (dd, J=12.9, 5.4 Hz, 1H), 4.41-4.37 (m, 1H), 4.06 (d, J=13.0 Hz, 2H), 3.99 (s, 3H), 3.03-2.83 (m, 5H), 2.65-2.53 (m, 2H), 2.22 (d, J=6.7 Hz, 2H), 2.17-1.98 (m, 7H), 1.85-1.80 (m, 3H), 1.24-1.11 (m, 2H).

Example 3: N-(2-(1-(2-(4-(2-(2, 6-dioxopiperidin-3-yl)-1, 3-dioxoisoindolin-5-yl) piperazin-1-yl) ethyl) piperidin-4-yl)-6-methoxy-2H-indazol-5-yl)-6-(trifluoromethyl) pyridinecarboxamide

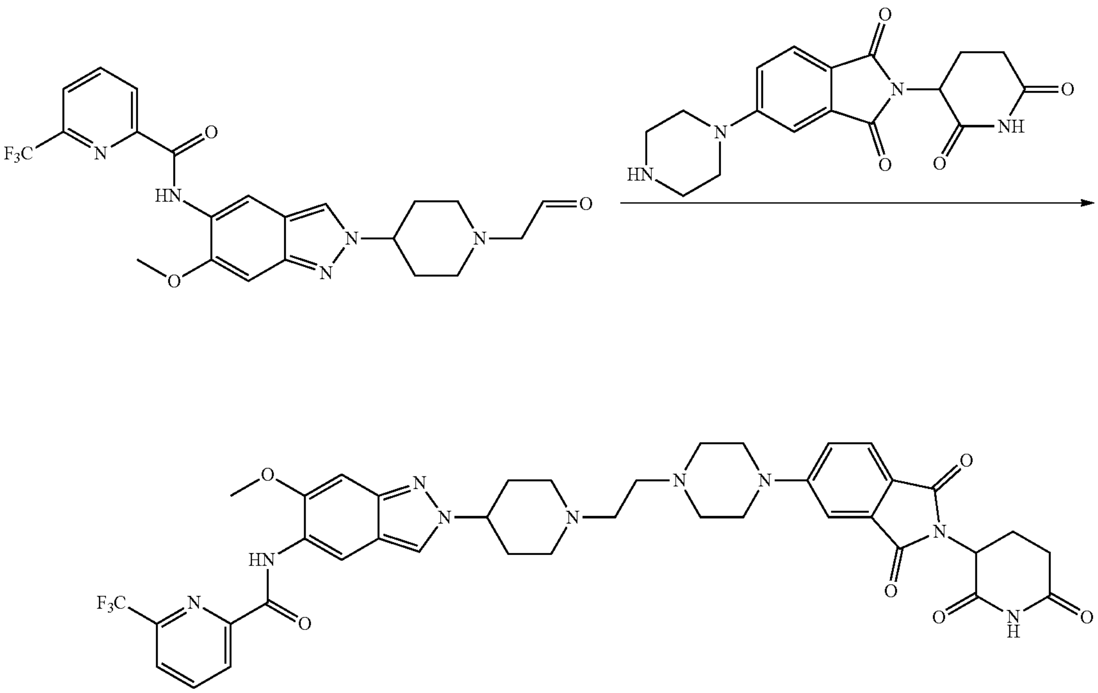

A mixture of N-(6-methoxy-2-(1-(2-oxoethyl) piperidin-4-yl)-2H-indazol-5-yl)-6-(trifluoromethyl) pyridinecarboxamide (80 mg, 0.174 mmol), 2-(2, 6-dioxopiperidin-3-yl)-5-(piperazin-1-yl) isoindoline-1, 3-dione (59 mg, 0.174 mmol) and STAB (110 mg, 0.521 mmol) in tetrahydrofuran (5 mL) was stirred for 3 h at room temperature. The resulting reaction mixture was diluted with ethyl acetate and washed with water and brine. The organic phase was collected, which was dried over anhydrous sodium sulfate and concentrated under reduced pressure. The concentrate was purified by preparative HPLC to obtain the product (4.5 mg).

LC-MS: (ESI, m/z): $[M+H]^+$=788.2.

1H NMR (400 MHz, DMSO-$d_6$) δ 11.08 (s, 1H), 10.51 (s, 1H), 8.69 (s, 1H), 8.53-8.33 (m, 3H), 8.22 (d, J=7.6 Hz, 1H), 7.68 (d, J=8.5 Hz, 1H), 7.39-7.22 (m, 2H), 7.17 (s, 1H), 5.12-5.04 (m, 1H), 4.46-4.32 (m, 1H), 3.98 (s, 3H), 3.52-3.44 (m, 6H), 3.10-3.02 (m, 3H), 2.94-2.84 (m, 1H), 2.62-2.53 (m, 6H), 2.15-1.95 (m, 8H).

Example 4: N-(2-(1-(2-(4-(2-(2, 6-dioxopiperidin-3-yl)-1, 3-dioxoisoindolin-5-yl) piperazin-1-yl) ethyl) piperidin-4-yl)-6-(2-hydroxyprop-2-yl)-2H-indazol-5-yl)-6-(trifluoromethyl) pyridinecarboxamide

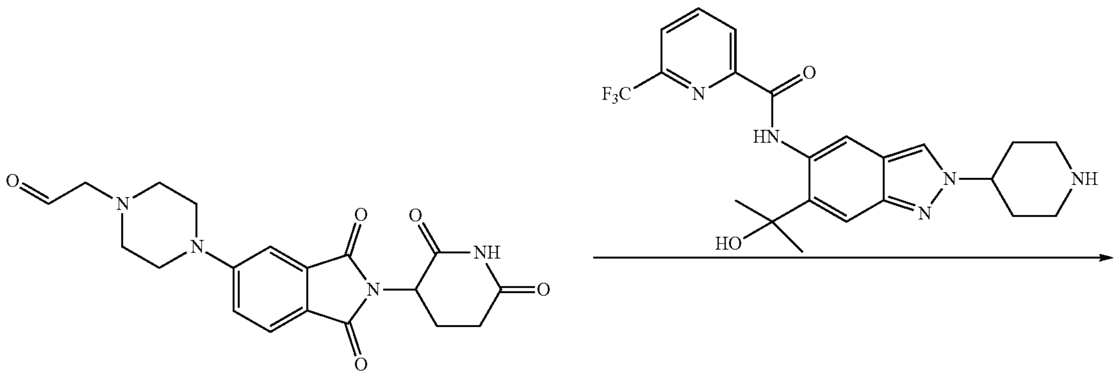

-continued

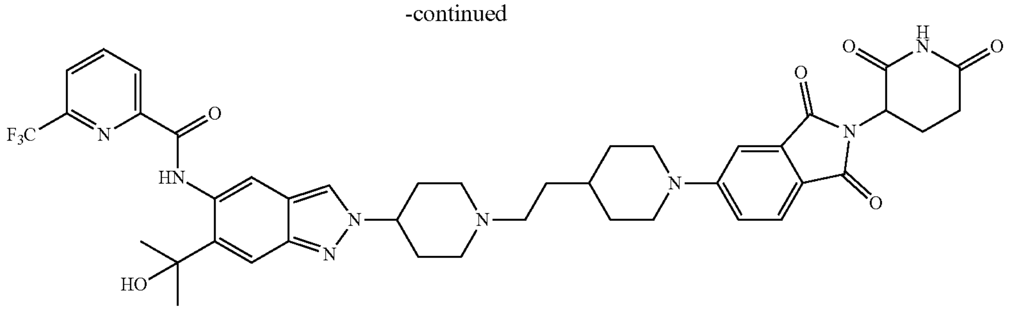

A mixture of N-(6-(2-hydroxyprop-2-yl)-2-(piperidin-4-yl)-2H-indazol-5-yl)-6-(trifluoromethyl) pyridinecarboxamide (285 mg, 0.64 mmol), 2-(4-(2-(2, 6-dioxopiperidin-3-yl)-1,3-dioxoisoindolin-5-yl) piperazin-1-yl) acetaldehyde (350 mg, 0.91 mmol) and STAB (407 mg, 1.92 mmol) in tetrahydrofuran (10 mL) was stirred overnight at room temperature. The reaction mixture was concentrated under reduced pressure, and the concentrate was purified by preparative HPLC to obtain the product (144.27 mg).

LC-MS: (ESI, m/z): $[M+H]^+$=816.2.

1H NMR (400 MHz, DMSO) δ 12.37 (s, 1H), 11.08 (s, 1H), 8.72 (s, 1H), 8.46-8.28 (m, 3H), 8.16 (d, J=7.8 Hz, 1H), 7.68 (d, J=8.5 Hz, 1H), 7.58 (s, 1H), 7.35 (d, J=1.9 Hz, 1H), 7.28-7.25 (m, 1H), 5.95 (s, 1H), 5.10-5.05 (m, 1H), 4.51-4.40 (m, 1H), 3.48-3.40 (m, 4H), 3.05 (d, J=10.5 Hz, 2H), 2.92-2.84 (m, 1H), 2.66-2.51 (m, 10H), 2.22-1.97 (m, 7H), 1.62 (s, 6H).

Example 5: N-(2-(1-(2-(1-(2-(2, 6-dioxopiperidin-3-yl)-1, 3-dioxoisoindolin-5-yl) piperidin-4-yl) ethyl) piperidin-4-yl)-6-(2-hydroxyprop-2-yl)-2H-indazol-5-yl)-6-(trifluoromethyl) pyridinecarboxamide A mixture of N-(6-(2-hydroxyprop-2-yl)-2-(piperidin-4-yl)-2H-indazol-5-yl)-6-(trifluoromethyl) pyridinecarboxamide (120 mg, 0.27 mmol), 2-(1-(2-(2, 6-dioxopiperidin-3-yl)-1, 3-dioxoisoindolin-5-yl) piperidin-4-yl) acetaldehyde (165 mg, 0.43 mmol) and STAB (172 mg, 0.81 mmol) in tetrahydrofuran (10 mL) was stirred overnight at room temperature. The reaction mixture was concentrated under reduced pressure to obtain a crude product. The crude product was purified by preparative HPLC to obtain the target product.

LC-MS: (ESI, m/z): $[M+H]^+$=815.3.

1H NMR (400 MHz, DMSO-$d_6$) δ 12.37 (s, 1H), 11.08 (s, 1H), 8.72 (s, 1H), 8.46-8.35 (m, 3H), 8.16 (d, J=7.8 Hz, 1H), 7.65 (d, J=8.5 Hz, 1H), 7.58 (s, 1H), 7.31 (d, J=1.8 Hz, 1H), 7.25-7.22 (m, 1H), 5.97-5.93 (m, 1H), 5.07 (dd, J=12.9, 5.4 Hz, 1H), 4.47-4.43 (m, 1H), 4.05 (d, J=13.0 Hz, 2H), 3.06-2.82 (m, 5H), 2.63-2.53 (m, 2H), 2.40 (t, J=7.1 Hz, 2H), 2.15-2.08 (m, 6H), 2.05-1.97 (m, 1H), 1.79 (d, J=10.9 Hz, 2H), 1.64 (d, J=13.1 Hz, 7H), 1.47-1.40 (m, 2H), 1.25-1.17 (m, 2H).

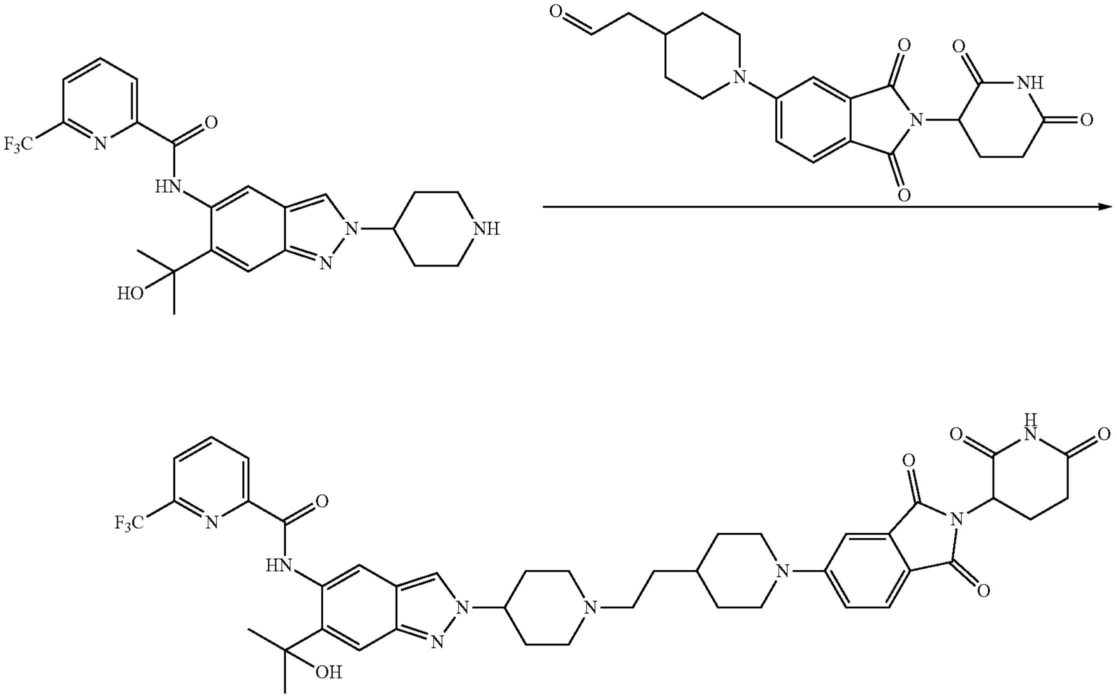

Example 6: N-(2-(1-(3-(1-(2-(2, 6-dioxopiperidin-3-yl)-1, 3-dioxoisoindolin-5-yl) piperidin-4-yl) propyl) piperidin-4-yl)-6-(2-hydroxyprop-2-yl)-2H-indazol-5-yl)-6-(trifluoromethyl) pyridinecarboxamide

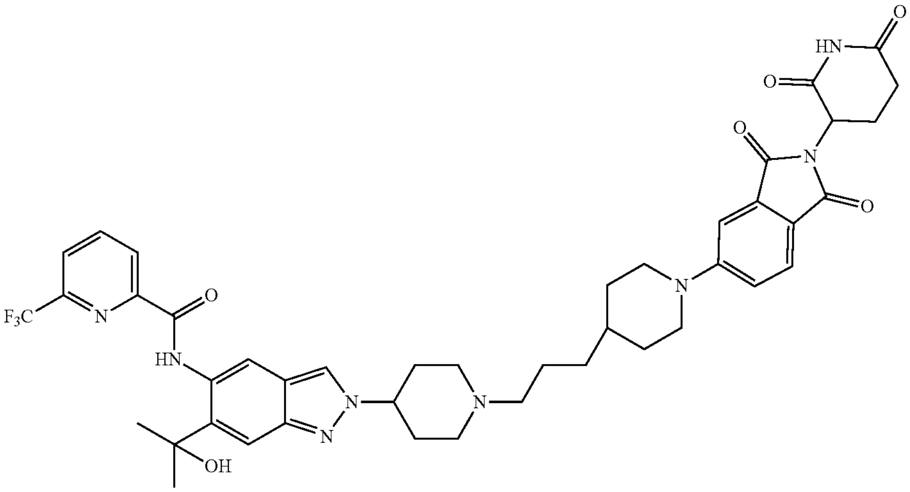 [SMILES: CC(C)(O)c1cc2nn(C3CCN(CCCC4CCN(c5ccc6c(c5)C(=O)N(C5CCC(=O)NC5=O)C6=O)CC4)CC3)cc2cc1NC(=O)c1cccc(C(F)(F)F)n1]

Synthesized with reference to the method of Example 5.

LC-MS: (ESI, m/z): $[M+H]^+$=829.4.

$^1$H NMR (400 MHz, DMSO-$d_6$) δ 12.37 (s, 1H), 11.07 (s, 1H), 8.72 (s, 1H), 8.45 (d, J=7.7 Hz, 1H), 8.40 (s, 1H), 8.37 (t, J=7.8 Hz, 1H), 8.16 (d, J=7.7 Hz, 1H), 7.65 (d, J=8.5 Hz, 1H), 7.58 (s, 1H), 7.31 (s, 1H), 7.24 (d, J=8.5 Hz, 1H), 5.95 (s, 1H), 5.06 (dd, J=12.8, 5.2 Hz, 1H), 4.49-4.37 (m, 1H), 4.06 (d, J=13.0 Hz, 2H), 3.08-2.81 (m, 5H), 2.64-2.52 (m, 2H), 2.37-2.27 (m, 2H), 2.19-1.95 (m, 7H), 1.77 (d, J=11.5 Hz, 2H), 1.67-1.45 (m, 9H), 1.30-1.10 (m, 4H).

Example 7: N-(2-(1-((1-(2-(2, 6-dioxopiperidin-3-yl)-1, 3-dioxoisoindolin-5-yl) piperidin-4-yl) methyl) piperidin-4-yl)-6-(2-hydroxyprop-2-yl)-2H-indazol-5-yl)-6-(trifluoromethyl) pyridinecarboxamide

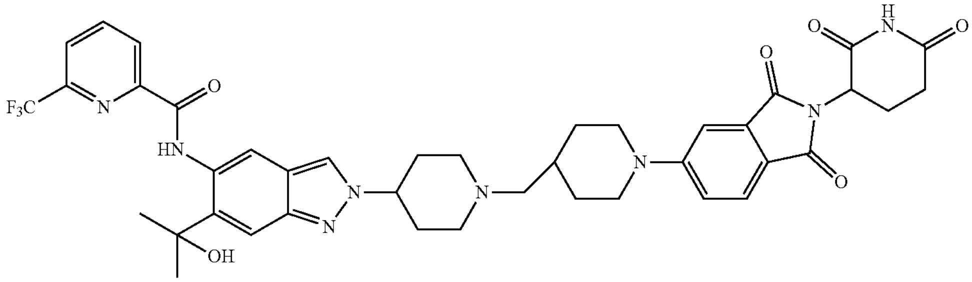 [SMILES: CC(C)(O)c1cc2nn(C3CCN(CC4CCN(c5ccc6c(c5)C(=O)N(C5CCC(=O)NC5=O)C6=O)CC4)CC3)cc2cc1NC(=O)c1cccc(C(F)(F)F)n1]

Synthesized with reference to the method of Example 5. LC-MS: (ESI, m/z): $[M+H]^+$=801.3.

$^1$H NMR (400 MHz, DMSO-$d_6$) δ 12.37 (s, 1H), 11.07 (s, 1H), 8.72 (s, 1H), 8.45 (d, J=7.7 Hz, 1H), 8.41 (s, 1H), 8.37 (t, J=7.8 Hz, 1H), 8.20-8.11 (m, 1H), 7.66 (d, J=8.6 Hz, 1H), 7.58 (s, 1H), 7.32 (s, 1H), 7.24 (dd, J=8.7, 2.0 Hz, 1H), 5.95 (s, 1H), 5.07 (dd, J=12.8, 5.4 Hz, 1H), 4.51-4.40 (m, 1H), 4.06 (d, J=13.2 Hz, 2H), 3.09-2.78 (m, 5H), 2.63-2.51 (m, 2H), 2.28-1.95 (m, 9H), 1.90-1.78 (m, 3H), 1.62 (s, 6H), 1.25-1.10 (m, 2H).

Example 8: N-(2-(1-(2-(1-(2-(2, 6-dioxopiperidin-3-yl)-1, 3-dioxoisoindolin-5-yl) piperidin-4-yl)$_2$-methylpropyl) piperidin-4-yl)-6-(2-hydroxyprop-2-yl)-2H-indazol-5-yl)-6-(trifluoromethyl) pyridinecarboxamide

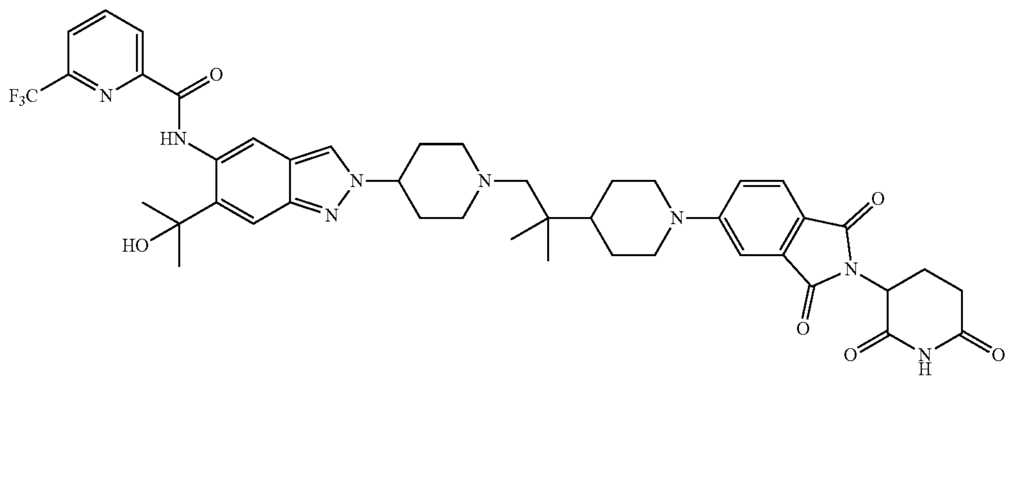 [SMILES: CC(C)(O)c1cc2nn(C3CCN(CC(C)(C)C4CCN(c5ccc6c(c5)C(=O)N(C5CCC(=O)NC5=O)C6=O)CC4)CC3)cc2cc1NC(=O)c1cccc(C(F)(F)F)n1]

Synthesized with reference to the method of Example 5. LC-MS: (ESI, m/z): $[M+H]^+$=843.1.

Example 9: N-(2-(1-(2-(4-(2-(2, 6-dioxopiperidin-3-yl)-1, 3-dioxoisoindolin-5-yl) piperidin-1-yl)$_2$-methylpropyl) piperidin-4-yl)-6-(2-hydroxyprop-2-yl)-2H-indazol-5-yl)-6-(trifluoromethyl) pyridinecarboxamide

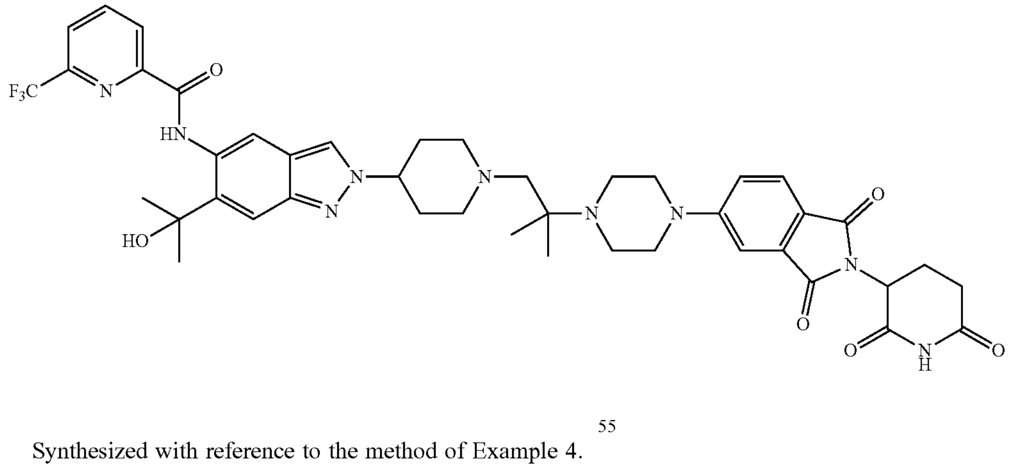

Synthesized with reference to the method of Example 4.

LC-MS: (ESI, m/z): $[M+H]^+$=844.1.

$^1$H NMR (400 MHz, DMSO-$d_6$) δ 12.36 (s, 1H), 11.07 (s, 1H), 8.71 (s, 1H), 8.45 (d, J=7.6 Hz, 1H), 8.40 (s, 1H), 8.37 (t, J=7.9 Hz, 1H), 8.16 (d, J=8.3 Hz, 1H), 7.68 (d, J=8.4 Hz, 1H), 7.58 (s, 1H), 7.33 (s, 1H), 7.25 (d, J=8.6 Hz, 1H), 5.94 (s, 1H), 5.07 (dd, J=12.9, 5.3 Hz, 1H), 4.50-4.35 (m, 1H), 3.45-3.35 (m, 4H), 3.15-3.02 (m, 2H), 2.95-2.85 (m, 1H), 2.77-2.70 (m, 4H), 2.68-2.53 (m, 2H), 2.45-2.30 (m, 4H), 2.20-2.07 (m, 2H), 2.05-1.97 (m, 3H), 1.62 (s, 6H), 1.06 (s, 6H).

Example 10: N-(2-(1-(3-(1-(2-(2, 6-dioxopiperidin-3-yl)-1, 3-dioxoisoindolin-5-yl) piperidin-4-yl)-3-methylbutyl) piperidin-4-yl)-6-(2-hydroxyprop-2-yl)-2H-indazol-5-yl)-6-(trifluoromethyl) pyridinecarboxamide

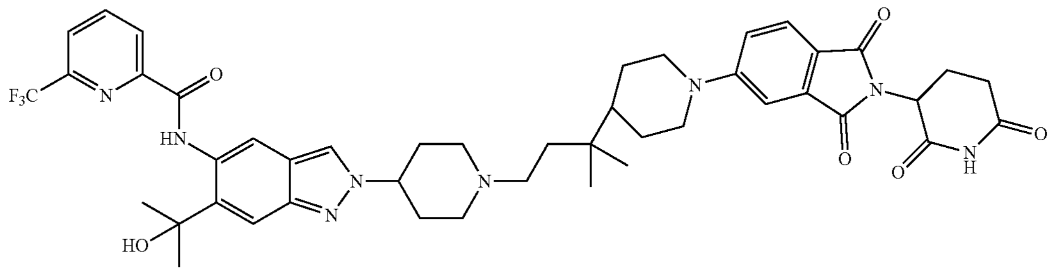

Synthesized with reference to the method of Example 5. LC-MS: (ESI, m/z): $[M+H]^+$=857.4.

Example 11: N-(2-(1-(3-(4-(2-(2, 6-dioxopiperidin-3-yl)-1, 3-dioxoisoindolin-5-yl) piperazin-1-yl)-3-methylbutyl) piperidin-4-yl)-6-(2-hydroxyprop-2-yl)-2H-indazol-5-yl)-6-(trifluoromethyl) pyridinecarboxamide

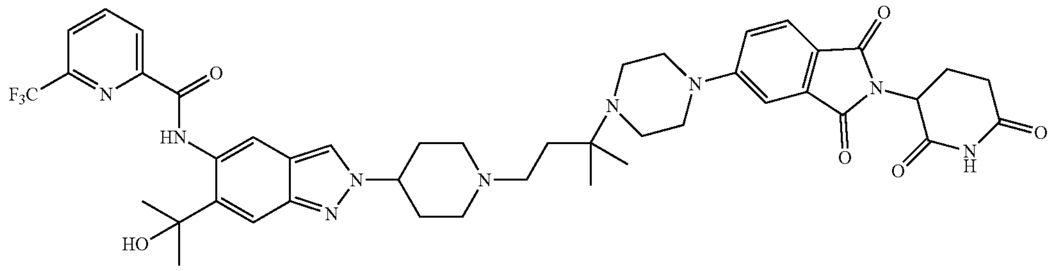 [SMILES: CC(C)(O)c1cc2nn(C3CCN(CCC(C)(C)C4CCN(c5ccc6c(c5)C(=O)N(C5CCC(=O)NC5=O)C6=O)CC4)CC3)cc2cc1NC(=O)c1cccc(C(F)(F)F)n1]

Synthesized with reference to the method of Example 4. LC-MS: (ESI, m/z): $[M+H]^+$=858.4.

Example 12: N-(2-(1-(2-(3-(2-(2, 6-dioxopiperidin-3-yl)-1, 3-dioxoisoindolin-5-yl)-3-azaspiro[5.5] undec-9-yl) ethyl) piperidin-4-yl)-6-(2-hydroxy-prop-2-yl)-2H-indazol-5-yl)-6-(trifluoromethyl) pyridinecarboxamide

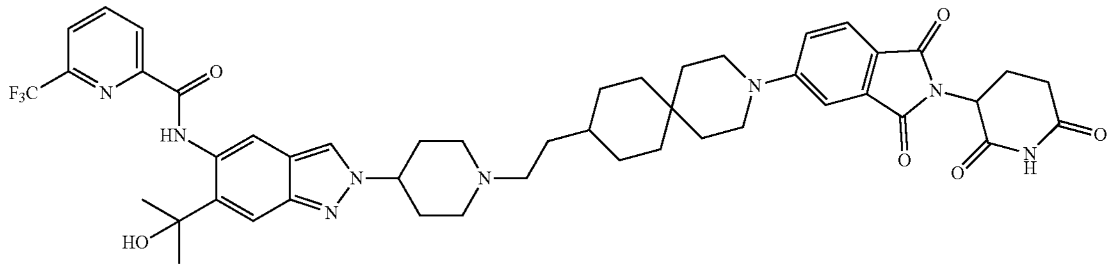 [SMILES: CC(C)(O)c1cc2nn(C3CCN(CCC4CCC5(CC4)CCN(c4ccc6c(c4)C(=O)N(C4CCC(=O)NC4=O)C6=O)CC5)CC3)cc2cc1NC(=O)c1cccc(C(F)(F)F)n1]

Synthesized with reference to the method of Example 5.

LC-MS: (ESI, m/z): $[M+H]^+$=883.4.

$^1$H NMR (400 MHz, DMSO-$d_6$) δ 12.37 (s, 1H), 11.03 (s, 1H), 8.72 (s, 1H), 8.45 (d, J=7.7 Hz, 1H), 8.40 (s, 1H), 8.37 (t, J=7.9 Hz, 1H), 8.16 (d, J=7.8 Hz, 1H), 7.65 (d, J=8.5 Hz, 1H), 7.58 (s, 1H), 7.29 (s, 1H), 7.21 (d, J=8.7 Hz, 1H), 5.95 (s, 1H), 5.06 (dd, J=12.9, 5.3 Hz, 1H), 4.46-4.37 (m, 1H), 3.50-3.40 (m, 4H), 3.05-2.95 (m, 2H), 2.94-2.80 (m, 1H), 2.63-2.51 (m, 2H), 2.36 (t, J=7.3 Hz, 2H), 2.16-1.93 (m, 7H), 1.73-1.49 (m, 12H), 1.45-1.35 (m, 4H), 1.34-1.25 (m, 1H), 1.19-1.05 (m, 4H).

Example 13: N-(2-(1-(9-(2-(2, 6-dioxopiperidin-3-yl)-1, 3-dioxoisoindolin-5-yl)-3, 9-diazaspiro [5.5] undec-3-yl) ethyl) piperidin-4-yl)-6-(2-hydroxy-prop-2-yl)-2H-indazol-5-yl)-6-(trifluoromethyl) pyridinecarboxamide

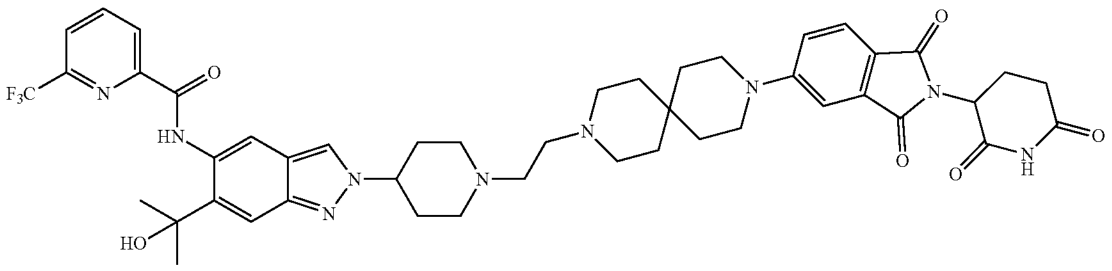 [SMILES: CC(C)(O)c1cc2nn(C3CCN(CCN4CCC5(CC4)CCN(c4ccc6c(c4)C(=O)N(C4CCC(=O)NC4=O)C6=O)CC5)CC3)cc2cc1NC(=O)c1cccc(C(F)(F)F)n1]

Synthesized with reference to the method of Example 4.

LC-MS: (ESI, m/z): $[M+H]^+$=884.4.

Example 14: N-(2-(1-(2-(3-(2-(2, 6-dioxopiperidin-3-yl)-1, 3-dioxoisoindolin-5-yl)-3-azaspiro[5.5] undec-9-yl)-2-methylpropyl) piperidin-4-yl)-6-(2-hydroxyprop-2-yl)-2H-indazol-5-yl)-6-(trifluoromethyl) pyridinecarboxamide

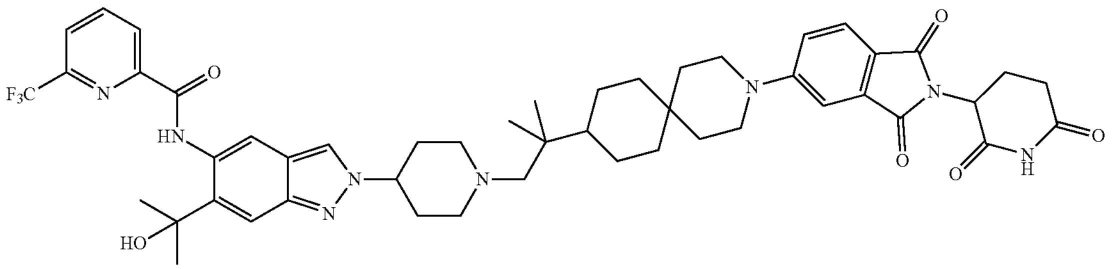 [SMILES: CC(C)(O)c1cc2nn(C3CCN(CC(C)(C)C4CCC5(CC4)CCN(c4ccc6c(c4)C(=O)N(C4CCC(=O)NC4=O)C6=O)CC5)CC3)cc2cc1NC(=O)c1cccc(C(F)(F)F)n1]

Synthesized with reference to the method of Example 5.

LC-MS: (ESI, m/z): $[M+H]^+$=911.4.

Example 15: N-(2-(1-(3-(2-(2, 6-dioxopiperidin-3-yl)-1, 3-dioxoisoindolin-5-yl)-3-azaspiro[5.5] undec-9-yl) methyl) piperidin-4-yl)-6-(2-hydroxy-prop-2-yl)-2H-indazol-5-yl)-6-(trifluoromethyl) pyridinecarboxamide

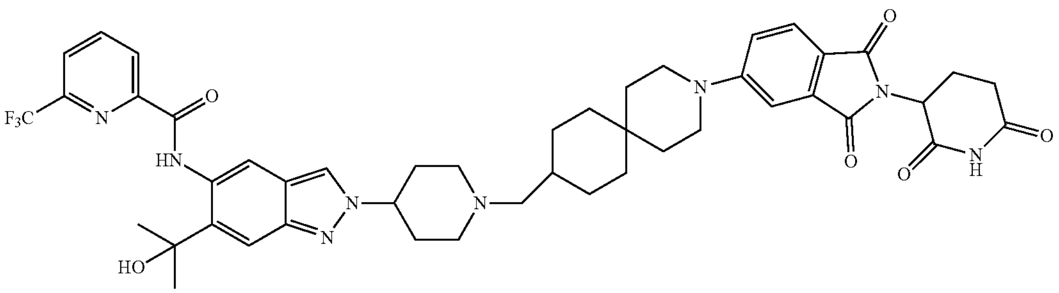 [SMILES: CC(C)(O)c1cc2nn(C3CCN(CC4CCC5(CC4)CCN(c4ccc6c(c4)C(=O)N(C4CCC(=O)NC4=O)C6=O)CC5)CC3)cc2cc1NC(=O)c1cccc(C(F)(F)F)n1]

Synthesized with reference to the method of Example 5. LC-MS: (ESI, m/z): $[M+H]^+$=869.4.

Example 16

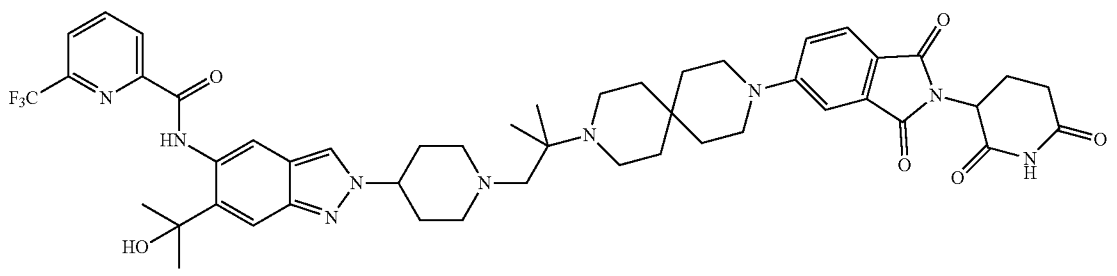

Synthesized with reference to the method of Example 4. LC-MS: (ESI, m/z): $[M+H]^+$=912.4.

Control Group 1: N-(2-(1-(2-(2-((2-(2, 6-dioxopiperidin-3-yl)-1, 3-dioxoisoindolin-5-yl) oxy) ethoxy) ethyl) piperidin-4-yl)-6-methoxy-2H-indazol-5-yl)-6-(trifluoromethyl) pyridinecarboxamide

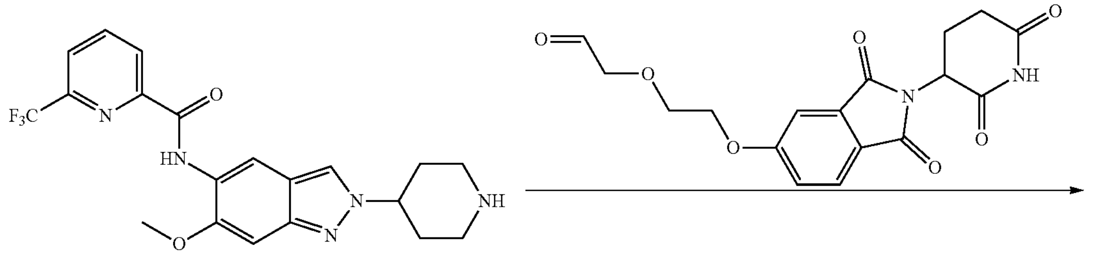

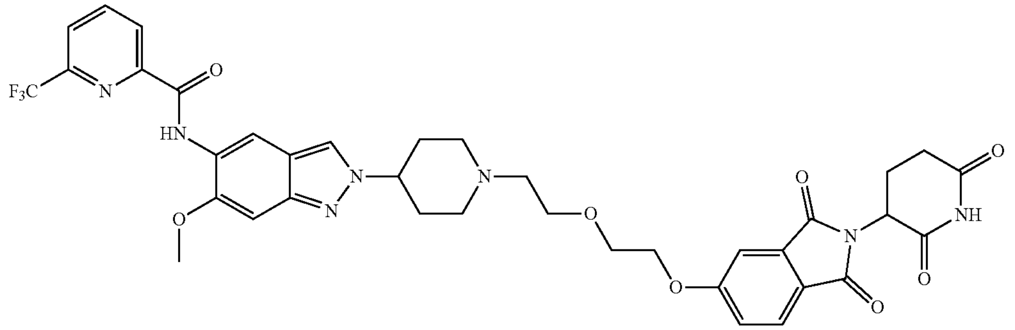

STAB (36 mg, 0.17 mmol) was added to a mixture of N-(6-methoxy-2-(piperidin-4-yl)-2H-indazol-5-yl)-6-(trifluoromethyl) pyridinecarboxamide (24 mg, 0.05 mmol) and 2-(2-((2-(2, 6-dioxopperidin-3-yl)-1, 3-dioxoisoindolin-5-yl) oxy) ethoxy) acetaldehyde (40 mg, 0.11 mmol) in 1, 2-dichloroethane (5 ml). The reaction solution was stirred at room temperature for 2 h. The solvent was removed by concentration under reduced pressure, and the concentrate was purified by HPLC to obtain 3.25 mg of target product as a white solid.

LC-MS: (ES, m/z): $[M+H]^+$=764.3.

$^1$H-NMR-LT-002-007: $^1$H NMR (400 MHz, $CD_3OD$_SPE) δ 8.77 (s, 1H), 8.47 (d, J=8.0 Hz, 3H), 8.31 (t, J=7.8 Hz, 1H), 8.18 (s, 1H), 8.05 (d, J=7.4 Hz, 1H), 7.81 (d, J=8.3 Hz, 1H), 7.47 (d, J=1.9 Hz, 1H), 7.35 (d, J=8.3 Hz, 1H), 7.07 (s, 1H), 5.12-5.07 (m, 1H), 4.51 (s, 1H), 4.37 (s, 2H), 4.05 (s, 3H), 3.91 (s, 2H), 3.82 (t, J=5.0 Hz, 2H), 3.37 (s, 2H), 2.96 (s, 2H), 2.90-2.77 (m, 1H), 2.77-2.60 (m, 4H), 2.26 (s, 4H), 2.08 (d, J=5.2 Hz, 1H).

Control Group 2: N-(2-(1-((1-(2-((2-(2, 6-dioxopiperidin-3-yl)-1, 3-dioxoisoindol-5-yl) oxy) ethyl) piperidin-4-yl) methyl) piperidin-4-yl)-6-methoxy-2H-indazol-5-yl)-6-(trifluoromethyl) pyridinecarboxamide Step 1: Preparation of 5-(allyloxy)-2-(2, 6-dioxopiperidin-3-yl) isoindoline-1, 3-dione

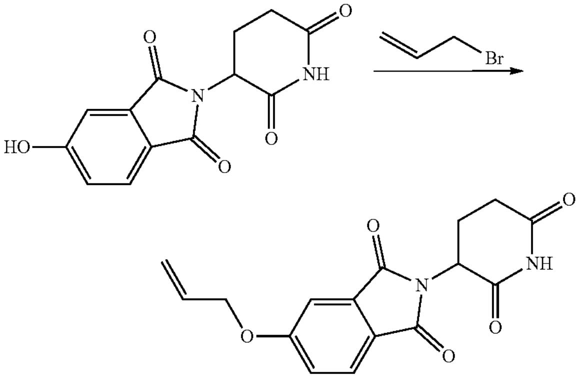

Under nitrogen protection, 3-bromoprop-1-ene mg, (470 mg, 3.89 mmol) was added to a mixture of 2-(2, 6-dioxopiperidin-3-yl)-5-hydroxyisoindoline-1, 3-dione (1 g, 3.65 mmol) and potassium carbonate (1.01 g, 7.29 mmol) in N,N-dimethylformamide (10 mL). The reaction mixture was stirred overnight at 50° C. At 0° C., the reaction was quenched with water (60 mL) and extracted with ethyl acetate (30 mL×3). The organic phase was collected and washed with saturated saline, dried over anhydrous sodium sulfate, filtered and concentrated under reduced pressure. The concentrate was purified by silica gel column to obtain 0.85 g of the target product.

LC-MS: (ES, m/z): $[M+H]^+$=315.1

Step 2:2-((2-(2,6-dioxopiperidin-3-yl)-1, 3-dioxoisoindolin-5-yl) oxy) acetaldehyde

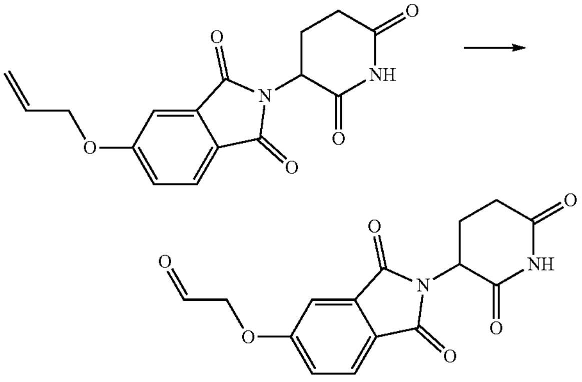

Ozone was introduced into a solution of 5-(allyloxy)-2-(2, 6-dioxopiperidin-3-yl) isoindoline-1, 3-dione (0.7 g, 2.23 mmol) in methylene chloride (200 ml) at −78° C. until the reaction solution turned to be blue. Then nitrogen was introduced until the reaction solution became colorless. Dimethyl sulfide (7.61 g, 123 mmol) was added at −78° C. under nitrogen protection, and the reaction mixture was stirred at room temperature overnight. The reaction solution was concentrated, and the concentrate was purified by silica gel column to obtain the target product.

LC-MS: (ES, m/z): $[M+H]^+$=317.1

Step 3: Preparation of N-(2-(1-((1-(2-((2-(2, 6-dioxopiperidin-3-yl)-1, 3-dioxoisoindol-5-yl) oxy) ethyl) piperidin-4-yl) methyl) piperidin-4-yl)-6-methoxy-2H-indazol-5-yl)-6-(trifluoromethyl) pyridinecarboxamide

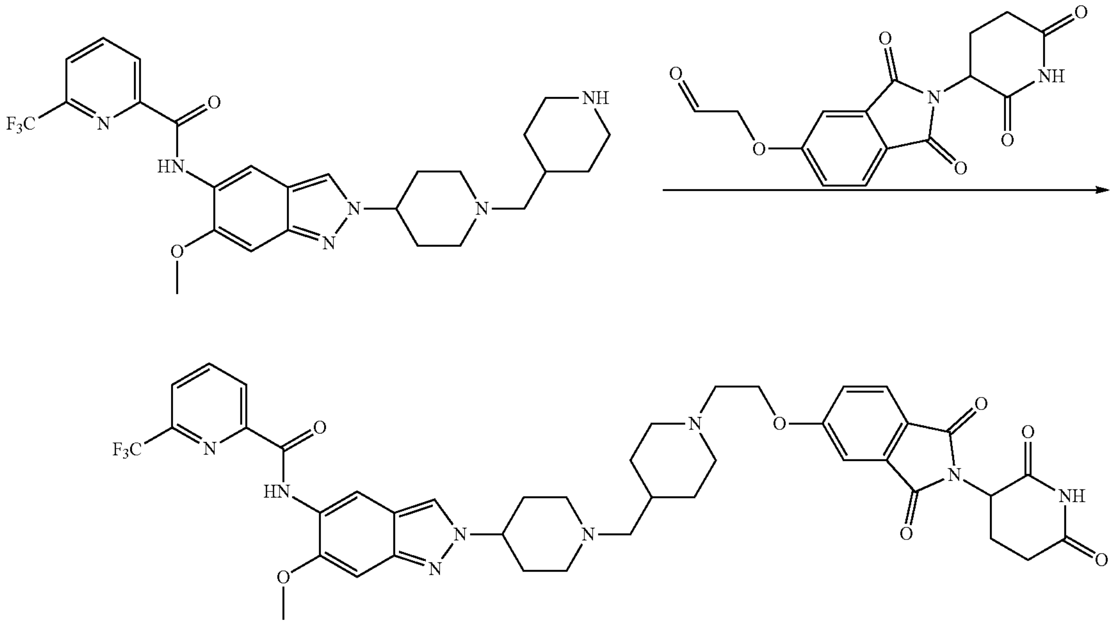

Synthesized with reference to the method of step 3 of control group 1.

LC-MS: (ESI, m/z): $[M+H]^+$=817.1.

$^1$H NMR (400 MHz, DMSO-$d_6$) δ 11.11 (s, 1H), 10.50 (s, 1H), 8.69 (s, 1H), 8.46 (d, J=7.6 Hz, 1H), 8.41 (t, J=7.8 Hz, 1H), 8.37 (s, 1H), 8.22 (d, J=8.6 Hz, 1H), 7.83 (d, J=8.3 Hz, 1H), 7.47 (d, J=2.2 Hz, 1H), 7.37 (dd, J=8.3, 2.3 Hz, 1H), 7.16 (s, 1H), 5.12 (dd, J=12.8, 5.3 Hz, 1H), 4.43-4.34 (m, 1H), 4.29 (t, J=5.5 Hz, 2H), 3.00-2.91 (m, 5H), 2.78-2.70 (m, 2H), 2.64-2.54 (m, 2H), 2.22-2.16 (m, 3H), 2.13-2.02 (m, 9H), 1.74-1.66 (m, 2H), 1.58-1.44 (m, 1H), 1.18-1.08 (m, 2H).

Control Group 3: N-(2-((1r,4r)-4-((((1-(2-(2, 6-dioxopiperidin-3-yl)-1, 3-dioxoisoindolin-4-yl) piperidin-4-yl) methyl)(methyl) amino) methyl) cyclohexyl)-6-(2-hydroxyprop-2-yl)-2H-indazol-5-yl)-6-(trifluoromethyl) pyridinecarboxamide

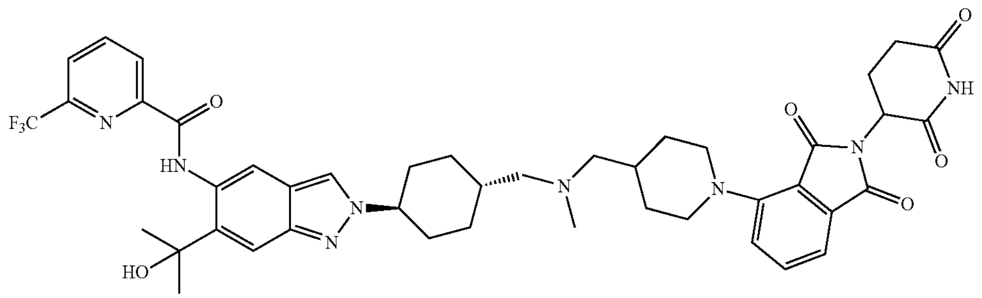 [SMILES: CN(CC1CCN(c2cccc3c2C(=O)N(C2CCC(=O)NC2=O)C3=O)CC1)C[C@H]1CC[C@H](n2cc3cc(NC(=O)c4cccc(C(F)(F)F)n4)c(C(C)(C)O)cc3n2)CC1]

Prepared with reference to the method of compound I-317 in WO2020113233.

LC-MS: (ESI, m/z): $[M+H]^+$=843.3

$^1$H NMR (400 MHz, DMSO-$d_6$) δ 12.36 (s, 1H), 11.08 (s, 1H), 8.71 (s, 1H), 8.45 (d, J=7.8 Hz, 1H), 8.41-8.32 (m, 2H), 8.16 (d, J=7.8 Hz, 1H), 7.74-7.62 (m, 1H), 7.57 (s, 1H), 7.42-7.17 (m, 2H), 5.94 (s, 1H), 5.09 (dd, J=12.8, 5.3 Hz, 1H), 4.47-4.36 (m, 1H), 3.70 (d, J=10.0 Hz, 2H), 2.90 (d, J=12.7 Hz, 3H), 2.65-2.52 (m, 2H), 2.25-2.10 (m, 9H), 2.05-1.81 (m, 7H), 1.74-1.55 (m, 8H), 1.32 (d, J=11.6 Hz, 2H), 1.11 (d, J=11.9 Hz, 2H)

II Biological Activity Test Example

Test Example 1: IRAK4 Kinase Activity Test

KinEASE-STK Si serine/threonine kinase kit (Cisbio) was used to detect the inhibitory effect of the compound on IRAK4 kinase activity. The specific method was: the compound was dissolved in dimethyl sulfoxide, and then it was diluted with the buffer solution of the kit by equal gradient to make the final concentration range of the tested compound in the reaction system 10000 nM-0.038 nM, then 2.5 nM kinase, 1 μM biotinylated polypeptide substrate and 7 μM adenosine triphosphate (ATP) were added in sequence and incubated at 37° C. for 120 min. Subsequently, anti-phosphorylated serine/threonine antibody coupled with europium element compound and modified XL665 streptavidin were added to the reaction system to terminate the reaction. After incubating at room temperature for 1 h, the fluorescence intensity of each well at the emission wavelength of 620 nm and 665 nm and the excitation wavelength of 337 nm was determined in HTRF mode on the microplate reader EnVision (PerkinElmer), the ratio value was calculated using the formula Ratio=(665 nm/620 nm)x$10^4$. By comparing with the fluorescence intensity ratio of the control group, the inhibition rate of the compound at each concentration was calculated, and then the $IC_{50}$ value of the compound was obtained by fitting the nonlinear curve with the logarithmic concentration-inhibition rate by GraphPad Prism 7.

Test Example 2: Degradation of IRAK4 in THP-1 Cells by Compounds

Each well of the 24-well cell culture plate was inoculated with 0.95 mL THP-1 cells (stem cell bank of Chinese academy of sciences) with a cell density of 5×$10^5$ cells/well. The cell plate was placed in a 5% carbon dioxide incubator and cultured overnight at 37° C., then 50 μL compound in dimethyl sulfoxide was added. The final concentration of the compound was in the range of 1-3000 nM. After continuous cultivation for 24 hours, the cells were collected into a 1.5 mL centrifuge tube, centrifuged at 1000 rpm and 4° C. for 5 minutes. Cell precipitation was washed twice with 1×DPBS, resuspended cells were lysed with 200 μL lysate (cell lysate was Western and IP cell lysate (Beyotime), supplemented with 1 mM mixture of phenylmethylsulfonyl fluoride and protease inhibitor (Beyotime)), left on ice for 30 minutes, then centrifuged at 14000 g at 4° C. for 10 minutes, and the supernatant was taken to detect IRAK4 protein level by Western blot.

The total protein concentration in the supernatant of cell lysis was determined by BCA protein quantitative kit (Tiangen). According to the concentration of total protein detected by BCA, the supernatant was adjusted to 0.2 μg/L with PBS and 5×SDS-PAGE protein loading buffer (Beyotime), bathed in water at 100° C. for 10 minutes, then placed in ice bath for 5 minutes, centrifuged at 14000 g and 4° C. for 5 minutes, and then collected as WB loading sample. Prefabricated glue (KeyGEN) was used for protein electrophoresis with a loading amount of 10 μL (total protein 2 μg). After Tris-MOPS-SDS electrophoresis solution (Adamas), 120V constant pressure electrophoresis was performed. After electrophoresis, the protein on the adhesive strip was transferred to PVDF membrane with a constant current of 250V for 50 minutes. After the membrane was transferred, the membrane was added in 1×QuickBlock blocking buffer (Beyotime) and incubated for 30 minutes at room temperature. After blocking, PVDF membranes were incubated with IRAK4 primary antibody (Abcam) overnight at 4°, the membranes were washed with TBST buffer (2.4 g Tris, 8.8 g NaCl, 1.5 mL Tween 20, pH adjusted to 7.4, constant volume to 1 L) for 30 minutes, incubated with secondary antibody (Abcam) for 2 hours at room temperature, finally incubated with Clarity Western ECL Substrate (BIO-RAD) for 5 minutes for luminescence development, chemiluminescence imaging system (Clinx, chemiScope 6200 Touch) was used for development and protein mapping photography. The protein map was analyzed by Clinx chemiluminescence analysis software for grayscale values. Using the formula: grayscale correction value=(target protein grayscale value/corresponding internal reference grayscale value)×103, the grayscale correction value of each sample was calculated. The degradation rate was calculated by comparing with the grayscale correction value of the control group. Furthermore, $DC_{50}$ and $D_{max}$ values of the compound were obtained by the nonlinear curve fitting with the logarithmic concentration-inhibition rate by GraphPad Prism 7.

TABLE 1

| | | WB | | WB | |
|---|---|---|---|---|---|
| Example | $IC_{50}$ (nM) | D(%) (1000 nM) | D(%) (300 nM) | $DC_{50}$ (nM) | $D_{max}$ (%) |
| Control group 1 | 44.2 | 65.1 | 73.9 | 38.1 | 73.9 |
| Control group 2 | 15.2 | 85.7 | 79.7 | 40.6 | 85.1 |
| Example 1 | 48.6 | 99.8 | 99.4 | 25.1 | 98.8 |
| Example 2 | 92.7 | 86.5 | 90.5 | 15.7 | 90.5 |
| Example 3 | 56.7 | 96.4 | 96.7 | 9.3 | 97.7 |
| Example 4 | 17.8 | 99.9 | 99.5 | 1.7 | 99.9 |
| Example 5 | 41.15 | 89.5 | 91.3 | 12.1 | 92.4 |
| Example 6 | 55.7 | 87.3 | 89.5 | 11.9 | 90.9 |
| Example 7 | 48.0 | 79.6 | 82.9 | 10.6 | 80.2 |
| Example 9 | 32.7 | 74.4 | 81.1 | 12.50 | 79.1 |
| Example 12 | 60.9 | 97.9 | 97.4 | 18.3 | 99.8 |

Note:
WB refers to the Western Blot method, D(%) refers to the degradation percentage of IRAK4 kinase protein in THP-1 cells by the compound of the present invention detected by Western Blot method, D(%)(1000 nM) is the degradation percentage of IRAK4 when the compound concentration is 1000 nM, and D(%)(300 nM) is the degradation percentage of IRAK4 when the compound concentration is 300 nM.

Experimental results: The compound of the present invention can effectively bind to the IRAK4 target protein; the compound of the present invention can significantly degrade the IRAK4 kinase protein in the cell.

Test Example 3: Pharmacokinetic Study

The following experimental scheme was used to study the pharmacokinetic behavior of the compound of the present invention in mice and evaluate its pharmacokinetic characteristics.

Experimental scheme: 3 healthy SD mice, male, weighing 18-25 mg, were given 100 mg/kg compound by gavage with a volume of 10 mL/kg, prepared with 500 DMSO/15% solutol % 80% PBS (w/v). Before the test, they were fasted for 12 hours and freely drank water. Food was uniformly consumed 4 h after administration.

Three healthy SD mice, male, weighing 18-25 mg, were given 1 mg/kg compound intravenously with a volume of 5 mL/kg, prepared with 5% DMSO/15% solutol %80% PBS (w/v). Before the test, they were fasted for 12 hours and freely drank water. Food was uniformly consumed 4 h after administration.

0.1 mL of venous blood was taken through the submaxillary venous plexus of mice at 0.08 h, 0.25 h, 0.5 h, 1 h, 2 h, 4 h, 8 h, 24 h after gavage administration and 0.08 h, 0.25 h, 0.5 h, 1 h, 2 h, 4 h, 8 h, 24 h after intravenous administration, placed in a heparin test tube, centrifuged at 11000 rpm for 5 min, and plasma was separated, the concentration of compounds in plasma was determined by liquid chromatography-tandem mass spectrometry.

TABLE 2

| | Intravenous injection (1 mg/kg) | | | gavage administration (100 mg/kg) | | |
|---|---|---|---|---|---|---|
| | $AUC_{last}$ (hr * ng/mL) | CL_pred (L/hr/kg) | $V_{ss}$_pred (L/kg) | $AUC_{last}$ (hr * ng/mL) | $C_{max}$ (ng/mL) | F % |
| Control group 2 | 122.4 | 5.5 | 109.4 | 1718.1 | 149.9 | 14.0 |
| Example 2 | 1918.3 | 0.5 | 3.3 | 22370.6 | 1233.3 | 22.3 |
| Example 6 | 2151.0 | 0.4 | 4.6 | 30466.8 | 1862.0 | 14.2 |
| Example 7 | 3113.2 | 0.3 | 2.2 | 41567.5 | 3262.2 | 13.4 |

The experimental results show that the compound of the present invention has low clearance rate, high plasma exposure, good oral bioavailability, good pharmacokinetic properties, and is beneficial to prepare a medicament.

Test Example 4: Degradation of IKZF1 and IKZF3 in L363 Cells by Compound

The 24-well cell culture plate was inoculated with 0.95 mL L363 cells (Nanjing Co-bioer) per well with a cell density of $6\times10^5$ cells/well. The cell plate was placed in a 5% carbon dioxide incubator and cultured at 37° C. for 8 hours, then 50 μL of compound solution was added. The final concentration of the compound was 1000 nM. After continuing to culture for 16 hours, the cells were collected into a 1.5 mL centrifuge tube and centrifuged at 3000 rpm and 4° C. for 5 minutes. Cell precipitation was washed twice with 1×DPBS, resuspended cells were lysed with 100 μL lysate (cell lysate was Western and IP cell lysate (Beyotime), supplemented with 1 mM mixture of phenylmethylsulfonyl fluoride and protease inhibitor (Beyotime)), left on ice for 30 minutes, then centrifuged at 14000 g at 4° C. for 10 minutes, and the supernatant was taken to detect IKZF1 and IKZF3 protein level by Western blot.

The total protein concentration in the supernatant of cell lysis was determined by BCA protein quantitative kit (Tiangen). According to the concentration of total protein detected by BCA, the supernatant was adjusted to 0.2 μg/L with PBS and 5×SDS-PAGE protein loading buffer (Beyotime), bathed in water at 100° C. for 10 minutes, then placed in ice bath for 5 minutes, centrifuged at 14000 g and 4° C. for 5 minutes, and then collected as WB loading sample. Prefabricated glue (KeyGEN) was used for protein electrophoresis with a loading amount of 10 μL (total protein 2 μg). After Tris-MOPS-SDS electrophoresis solution (Adamas), 120V constant pressure electrophoresis was performed. After electrophoresis, the protein on the adhesive strip was transferred to PVDF membrane with a constant current of 250V for 50 minutes. After the membrane was transferred, the membrane was incubated in 5% bovine serum albumin solution for 2 hours at room temperature. After blocking, PVDF membranes were incubated with IKZF1 primary antibody (CST) and IKZF3 primary antibody (Abcam) overnight at 4°, the membranes were washed with TBST buffer (2.4 g Tris, 8.8 g NaCl, 1.5 mL Tween 20, pH adjusted to 7.4, constant volume to 1 L) for 30 minutes, incubated with secondary antibody (Abcam) for 2 hours at room temperature, finally incubated with Clarity Western ECL Substrate (BIO-RAD) for 5 minutes for luminescence development, chemiluminescence imaging system (Clinx, chemiScope 6200 Touch) was used for development and protein mapping photography. The protein map was analyzed by Clinx chemiluminescence analysis software for grayscale values. Using the formula: grayscale correction value=(target protein grayscale value/corresponding internal reference grayscale value)x$10^3$, the grayscale correction value of each sample was calculated. The degradation rate was calculated by comparing with the grayscale correction value of the control group.

TABLE 4

| Compound | Concentration (nM) | IKZF1 degradation rate (%) | IKZF3 degradation rate (%) |
|---|---|---|---|
| Control group 2 | 1000 | 47.5 ± 9.7 | 71.2 ± 5.7 |
| Control group 3 | 1000 | 97.2 ± 2.6 | 92.8 ± 5.0 |
| Example 4 | 1000 | 4.3 ± 0.8 | −4.5 ± 2.9 |
| Example 5 | 1000 | 18.8 ± 2.7 | 22.4 ± 6.6 |
| Example 6 | 1000 | 26.7 ± 2.4 | 8.4 ± 6.0 |
| Pomalidomide | 1000 | 99.7 ± 0.2 | 98.6 ± 0.6 |

Note:
In Table 4, "—" refers to no degradation of IKZF1 and IKZF3.

The experimental results show that the compound of the present invention has good selectivity, no or a small amount of degradation to IKZF1 and IKZF3, and has small toxic and side effects, which is beneficial to prepare a medicament.

The invention claimed is:

1. A compound of formula I, or a stereoisomer, an enantiomer, a diastereomer, a deuterate, a hydrate, a solvate, or a pharmaceutically acceptable salt thereof,

I

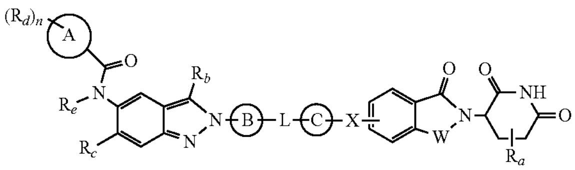

wherein:

$R_a$ is hydrogen;

ring A is 5-10 membered heteroaryl;

$R_d$ is each independently halogen, or C1-C6 alkyl, wherein the alkyl is optionally substituted by one or more halogen;

n is 1;

$R_e$ is hydrogen or C1-C6 alkyl;

$R_c$ is —O—(C1-C6 alkyl), C1-C6 alkyl, C2-C6 alkenyl, or C2-C6 alkynyl, wherein the alkyl groups are optionally substituted by one or more hydroxyl;

$R_b$ is hydrogen, C1-C6 alkyl, C2-C6 alkenyl, or C2-C6 alkynyl;

ring B is 3-12 membered heterocycloalkyl containing 1-2 heteroatoms selected from N, O or S;

ring C is 3-12 membered heterocycloalkyl containing 1-2 heteroatoms selected from N, O or S;

X is bond;

W is C(O);

L is $-(CH_2)_j-$, and one or more $CH_2$ in the $-(CH_2)_j-$ are optionally replaced by a group selected from $CR^{1'}R^{2'}$;

$R^{1'}$ and $R^{2'}$ are each independently C1-C4 alkyl, and j is 1, 2, 3, 4, 5 or 6.

2. The compound of formula I according to claim 1, or the stereoisomer, the enantiomer, the diastereomer, the deuterate, the hydrate, the solvate, or the pharmaceutically acceptable salt thereof, wherein, ring B is 3-8-membered monocyclic heterocycloalkyl containing 1-2 N heteroatoms.

3. The compound of formula I according to claim 2, or the stereoisomer, the enantiomer, the diastereomer, the deuterate, the hydrate, the solvate, or the pharmaceutically acceptable salt thereof, wherein ring B is piperidinyl or piperazinyl.

4. The compound of formula I according to claim 1, or the stereoisomer, the enantiomer, the diastereomer, the deuterate, the hydrate, the solvate, or the pharmaceutically acceptable salt thereof, wherein, ring C is 3-8-membered monocyclic heterocycloalkyl containing 1-2 N heteroatoms, or 7-12-membered spiro heterocycloalkyl containing 1-2 N heteroatoms.

5. The compound of formula I according to claim 4, or the stereoisomer, the enantiomer, the diastereomer, the deuterate, the hydrate, the solvate, or the pharmaceutically acceptable salt thereof, wherein ring C is, piperidinyl, piperazinyl,

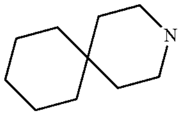

or

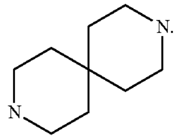

6. The compound of formula I according to claim 1, or the stereoisomer, the enantiomer, the diastereomer, the deuterate, the hydrate, the solvate, or the pharmaceutically acceptable salt thereof, wherein ring A is pyridyl.

7. The compound of formula I according to claim 6, or the stereoisomer, the enantiomer, the diastereomer, the deuterate, the hydrate, the solvate, or the pharmaceutically acceptable salt thereof, wherein, $R_d$ is each independently halogen or C1-C6 alkyl optionally substituted by one or more F.

8. The compound of formula I according to claim 7, or the stereoisomer, the enantiomer, the diastereomer, the deuterate, the hydrate, the solvate, or the pharmaceutically acceptable salt thereof, wherein $R_d$ is hydrogen, F, methyl, difluoromethyl, trifluoromethyl or 2-hydroxypropyl.

9. The compound of formula I according to claim 1, or the stereoisomer, the enantiomer, the diastereomer, the deuterate, the hydrate, the solvate, or the pharmaceutically acceptable salt thereof, wherein, $R_c$ is C1-C6 alkyl optionally substituted by one or more hydroxyl, or $R_c$ is —O(C1-C6 alkyl) optionally substituted by one or more hydroxyl.

10. The compound of formula I according to claim 9, or the stereoisomer, the enantiomer, the diastereomer, the deuterate, the hydrate, the solvate, or the pharmaceutically acceptable salt thereof, wherein, $R_c$ is 2-hydroxypropyl, methoxy, ethoxy or isopropoxy.

11. The compound of formula I according to claim 1, or the stereoisomer, the enantiomer, the diastereomer, the deuterate, the hydrate, the solvate, or the pharmaceutically acceptable salt thereof, wherein $R_b$ is hydrogen or methyl.

12. The compound of formula I according to claim 1, or the stereoisomer, the enantiomer, the diastereomer, the deuterate, the hydrate, the solvate, or the pharmaceutically acceptable salt thereof, wherein L is $-(CH_2)_j-$, and one or more $CH_2$ in the $-(CH_2)_j-$ are optionally replaced by a group selected from $-CR^{1'}R^{2'}$; wherein $R^{1'}$ and $R^{2'}$ are each independently C1-C4 alkyl, j is 1, 2 or 3.

13. The compound of formula I according to claim 12, or the stereoisomer, the enantiomer, the diastereomer, the deuterate, the hydrate, the solvate, or the pharmaceutically acceptable salt thereof, wherein L is

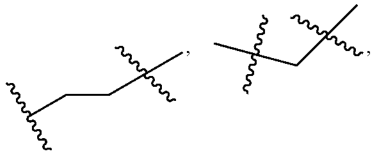

-continued

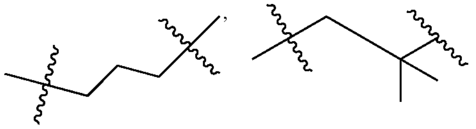

or

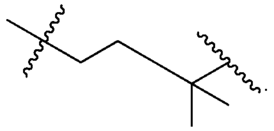

14. The compound of formula I according to claim 1, or the stereoisomer, the enantiomer, the diastereomer, the deuterate, the hydrate, the solvate, the or the pharmaceutically acceptable salt thereof, wherein the compound is the following specific compounds

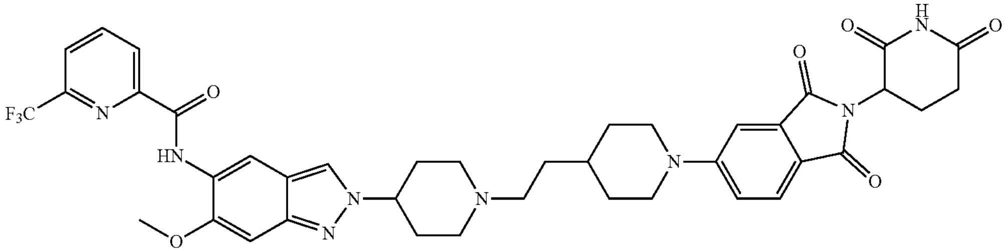

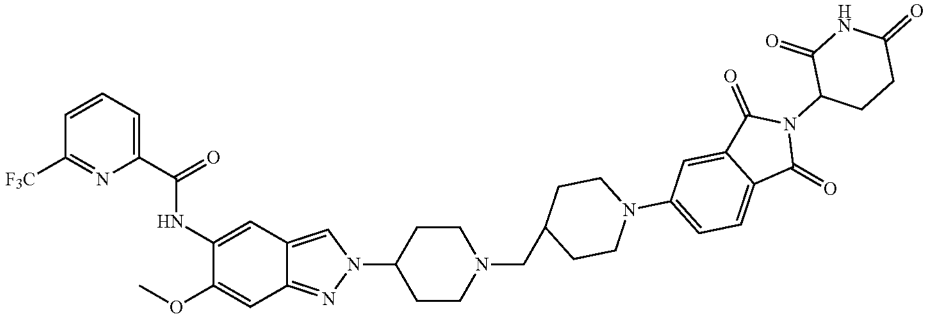

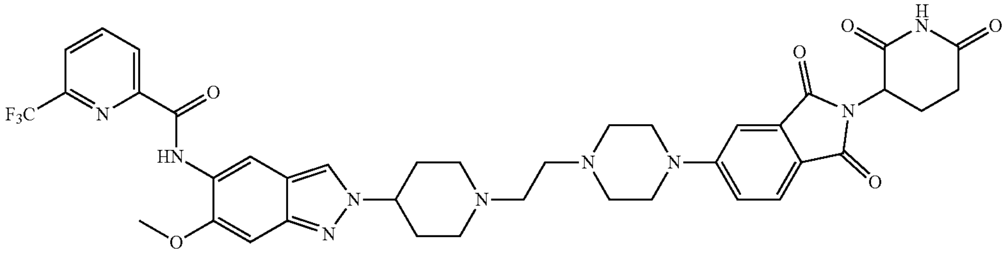

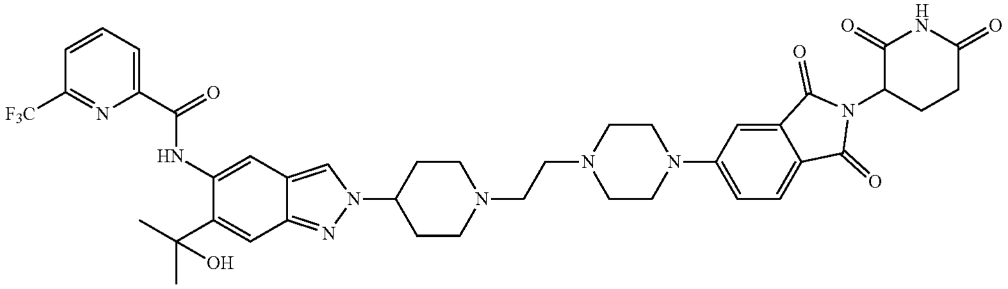

-continued
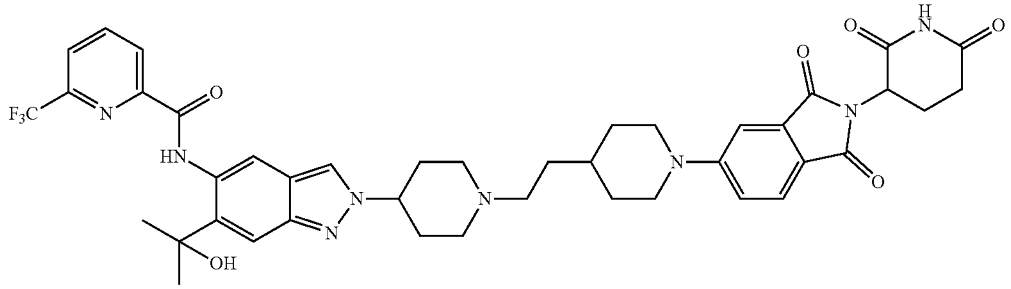
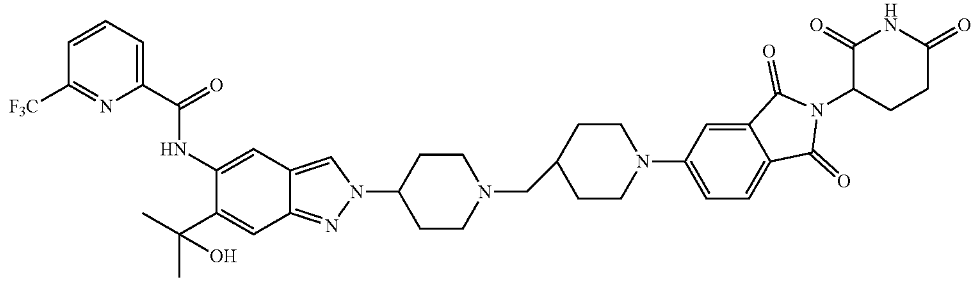
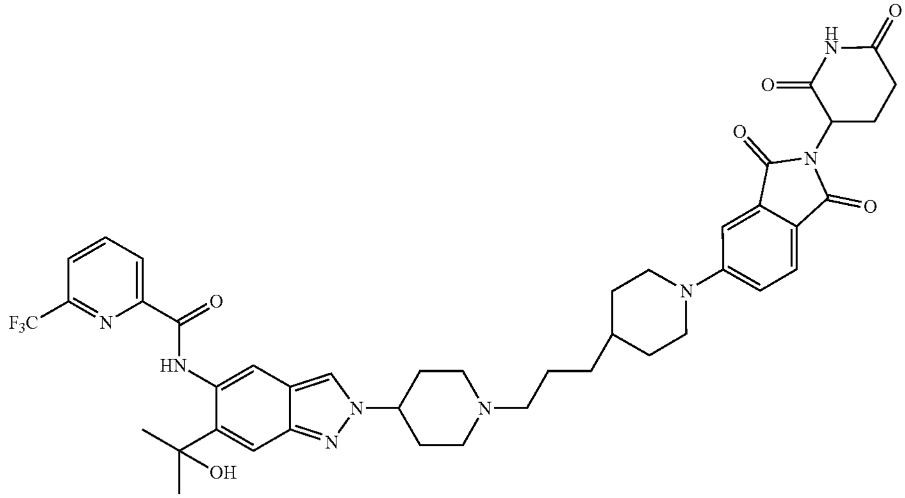
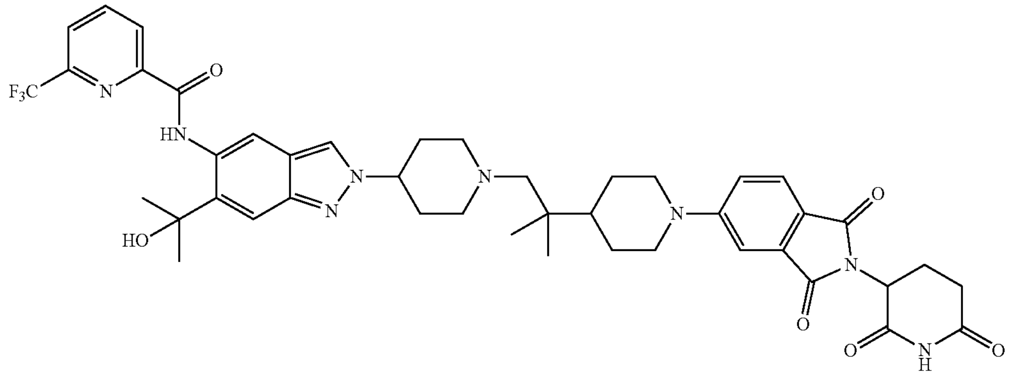

-continued
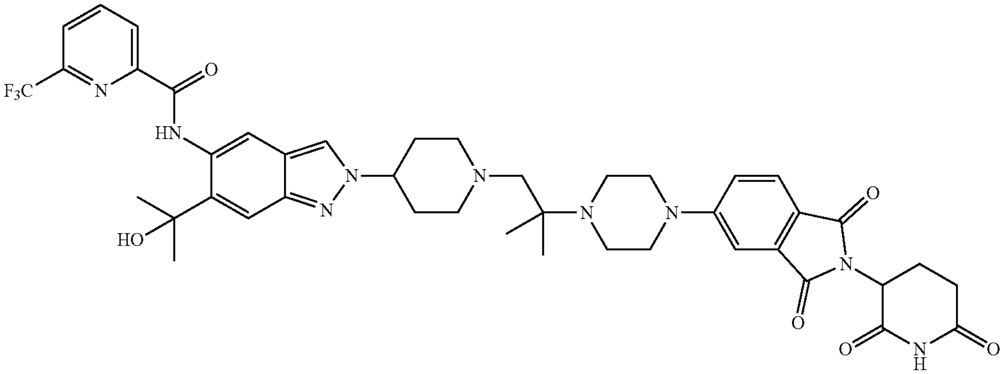
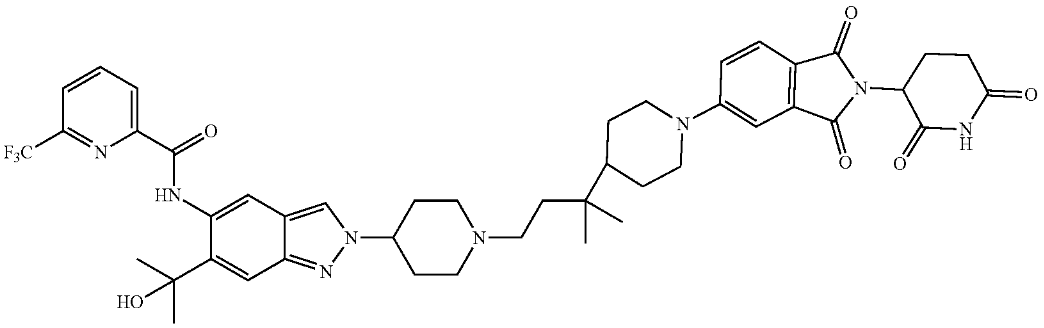
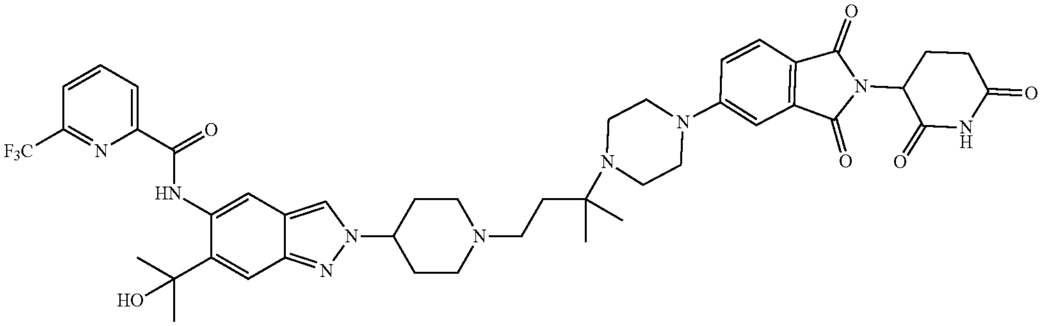
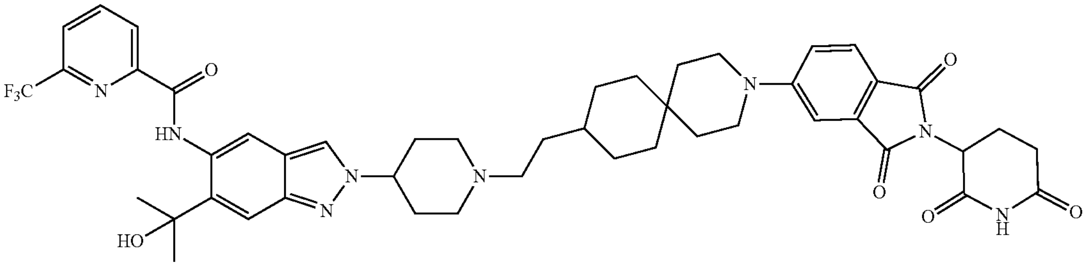
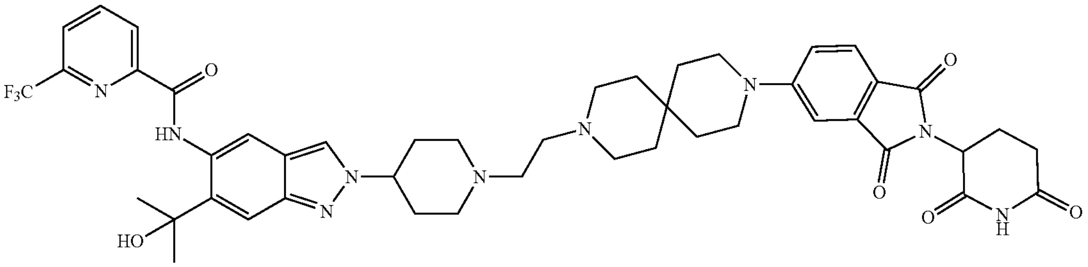

-continued

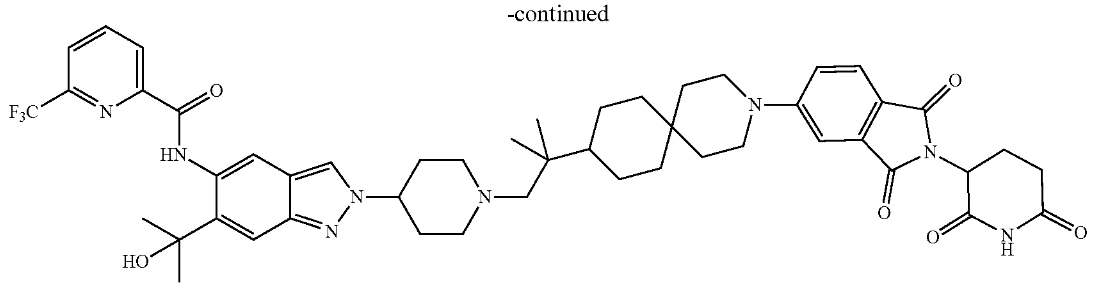

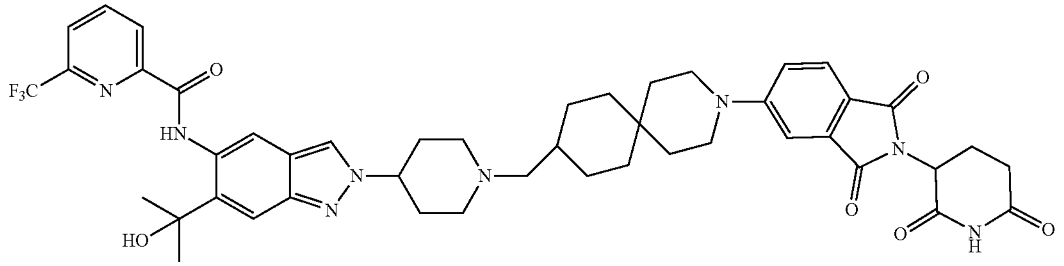

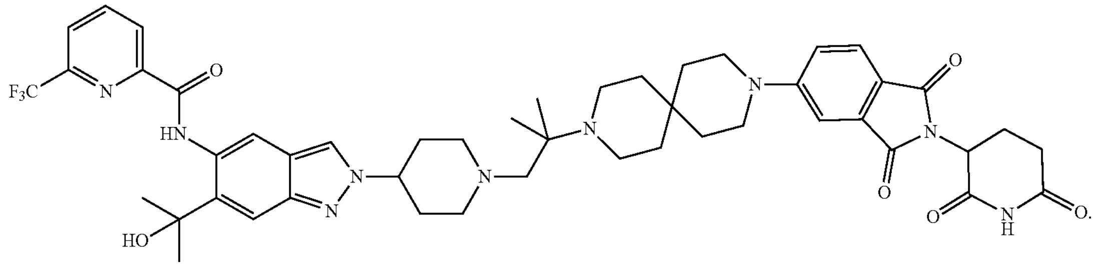

15. A pharmaceutical composition comprising the compound according to claim 1, or the stereoisomer, the enantiomer, the diastereomer, the deuterate, the hydrate, the solvate, or the pharmaceutically acceptable salt thereof, and a pharmaceutically acceptable carrier, diluent or excipient.

16. A method for the treatment or prevention of IRAK4-mediated diseases or conditions, or TLR (other than TLR3R) or IL-1β receptor family mediated diseases or conditions comprising the step of administrating the compound of claim 1, or the stereoisomer, the enantiomer, the diastereomer, the deuterate, the hydrate, the solvate, the and/or the pharmaceutically acceptable salt thereof to a subject in need thereof.

17. A method for the treatment or prevention of cancer, neurodegenerative diseases, viral diseases, autoimmune diseases, inflammatory diseases, hereditary diseases, hormone-related diseases, metabolic diseases, organ transplantation-related diseases, immunodeficiency diseases, destructive bone diseases, proliferative disorders, infectious diseases, conditions related to cell death, thrombin-induced platelet aggregation, liver diseases, pathological immune conditions involving T cell activation, cardiovascular diseases or CNS diseases comprising the step of administrating the compound of claim 1, or the stereoisomer, the enantiomer, the diastereomer, the deuterate, the hydrate, the solvate, or the pharmaceutically acceptable salt thereof to a subject in need thereof.

18. A method for the treatment or prevention of brain cancer, kidney cancer, liver cancer, adrenal cancer, bladder cancer, breast cancer, gastric cancer, ovarian cancer, colon cancer, rectal cancer, prostate cancer, pancreatic cancer, lung cancer, vaginal cancer, cervical cancer, testicular cancer, genitourinary cancer, esophageal cancer, Laryngeal cancer, skin cancer, bone cancer, thyroid cancer, sarcoma, glioblastoma, neuroblastoma, multiple myeloma, gastrointestinal cancer, neck or head tumor, epidermal hyperhyperplasia, psoriasis, prostate hyperplasia, Adenoma, adenocarcinoma, keratoacanthoma, epidermoid cancer, large cell carcinoma, non-small cell lung cancer, lymphoma, Hodgkin's and non-Hodgkin's, breast cancer, follicular cancer, undifferentiated tumor, papillary tumor, seminoma, melanoma, ABC DLBCL, Hodgkin's lymphoma, primary cutaneous T-cell lymphoma, chronic lymphocytic leukemia, smoldering indolent multiple myeloma, leukemia, diffuse large B-cell lymphoma (DLBCL), chronic lymphocytic leukemia (CLL), chronic lymphocytic lymphoma, primary exudative lymphoma, Burkitt lymphoma/leukemia, acute lymphocytic leukemia, pre-B cell lymphocytic leukemia, lymphoplasmic lymphoma, Waldenstroms's macroglobulinemia (WM), splenic marginal zone lymphoma, multiple myeloma, or plasmacytoma or intravascular large B-cell lymphoma, Alzheimer's disease, Parkinson's disease, amyotrophic lateral sclerosis, Huntington's disease, cerebral ischemia or traumatic injury, glutamate neurotoxicity, hypoxia, epilepsy, diabetes treatment, metabolic syndrome, obesity, neurodegenerative diseases caused by organ transplantation or graft-versus-host disease, eye disease, such as eye allergy, conjunctivitis, dry eye or spring conjunctivitis, diseases affecting the nose, including allergic rhinitis; autoimmune hematological diseases, such as hemolytic anemia, aplastic anemia, pure red blood cell anemia and idiopathic thrombocytopenia, systemic lupus erythematosus, rheumatoid arthritis, polychondritis, scleroderma, dermatomyositis, chronic active hepatitis, myasthenia gravis, Stephen-Johnson syndrome, idiopathic stomatitis diarrhea, autoimmune inflammatory bowel disease, bowel syndrome, celiac disease, root periostitis, lung hyaline membrane disease, nephropathy, glomerular disease, Alcoholic liver disease, multiple sclerosis, endocrine ophthalmopathy, Grave's disease, Sarcomatosis, dry eye, spring conjunctival keratitis, interstitial pulmonary fibrosis, psoriatic arthritis, systemic juvenile idiopathic arthritis, nephritis, vasculitis, interstitial cystitis, diverticulitis, Glomerulonephritis, chronic granulomatous disease, endometriosis, leptospirosis nephropathy, glaucoma, retinal disease, aging, headache, pain, complex regional pain syndrome, cardiac hypertrophy, muscle atrophy, catabolismobesity, slow fetal growth, hypercholesterolemia, heart disease, chronic heart failure, mesothelioma, anhidromic ectodermal dysplasia, Behcet's disease, pigment incontinence, Paget's disease, pancreatitis, hereditary periodic fever syndrome, asthma, acute lung injury, acute respiratory distress syndrome, eosinophilia, allergic reaction, systemic allergic reaction, sinusitis, eye allergy, silica-induced diseases, COPD, lung disease, cystic fibrosis, acid-induced lung injury, pulmonary hypertension, polyneuropathy, Cataract, muscle inflammation combined with systemic sclerosis, inclusion body myositis, myasthenia gravis, thyroiditis, Addison's disease, lichen planus, type 1 diabetes, type 2 diabetes, appendicitis, atopic dermatitis, asthma, allergies, bronchiolitis, bronchitis, bursitis, cervicitis, cholangitis, cholecystitis, chronic transplant rejection, colitis, conjunctivitis, cystitis, lacrimal gland inflammation, dermatitis, dermatomyositis, encephalitis, endocarditis, Endometritis, enteritis, enterocolitis, upper ankle inflammation, epididymitis, fasciitis, fibrous tissue inflammation, gastritis, gastroenteritis, Henoch-Schonlein purpura, hepatitis, suppurative sweat Inflammation, immunoglobulin A nephropathy, interstitial lung disease, laryngitis, mastitis, meningitis, myelitis, myocarditis, myositis, nephritis, liver fibrosis, renal fibrosis, alcoholic fatty liver, non-alcoholic fatty liver, heart fibrosis, psoriasis, Crohn's disease, inflammatory bowel disease, oophoritis, orchitis, osteitis, otitis, pancreatitis, mumps, pericarditis, peritonitis, pharyngitis, pleurisy, phlebitis, local pneumonia, pneumonia, polymyositis, proctitis, prostatitis, pyelonephritis, rhinitis, salpingitis, sinusitis, stomatitis, articular inflammation, tendinitis, tonsillitis, ulcerative colitis, uveitis, vaginitis, vasculitis, vulvitis, alopecia areata, erythema multiforme, dermatitis herpetiformis, sclerosis, vitiligo, hypersensitivity vasculitis, urticaria, bullous pemphigoid, pemphigus vulgaris, deciduous pemphigus, paraneoplastic pemphigus, acquired bullous epidermal laxity, acute and chronic gout, chronic gouty arthritis, bovine skin moss, bovine skin arthritis, rheumatoid arthritis, juvenile rheumatoid arthritis, cryopyrin-associated periodic syndrome or osteoarthritis diseases comprising the step of administrating the compound of claim 1, or the stereoisomer, the enantiomer, the diastereomer, the deuterate, the hydrate, the solvate, or the pharmaceutically acceptable salt thereof into a subject in need thereof.

* * * * *